United States Patent
Pratt, II

(10) Patent No.: US 12,116,605 B2
(45) Date of Patent: Oct. 15, 2024

(54) MUTANT AND GENETICALLY MODIFIED FILAMENTOUS FUNGAL STRAINS COMPRISING ENHANCED PROTEIN PRODUCTIVITY PHENOTYPES AND METHODS THEREOF

(71) Applicant: DANISCO US INC, Palo Alto, CA (US)

(72) Inventor: Robert James Pratt, II, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 933 days.

(21) Appl. No.: 17/264,061

(22) PCT Filed: Jul. 25, 2019

(86) PCT No.: PCT/US2019/043348
§ 371 (c)(1),
(2) Date: Jan. 28, 2021

(87) PCT Pub. No.: WO2020/028126
PCT Pub. Date: Feb. 6, 2020

(65) Prior Publication Data
US 2021/0301276 A1    Sep. 30, 2021

Related U.S. Application Data

(60) Provisional application No. 62/711,846, filed on Jul. 30, 2018.

(51) Int. Cl.
*C12N 9/34*    (2006.01)
(52) U.S. Cl.
CPC .... *C12N 9/2428* (2013.01); *C12Y 302/01003* (2013.01)
(58) Field of Classification Search
None
See application file for complete search history.

(56) References Cited

PUBLICATIONS

Berner et al., Protein Quality Control of the Endoplasmic Reticulum and Ubiquitin-Proteasome-Triggered Degradation of Aberrant Proteins: Yeast Pioneers the Path. Annu. Rev. Biochem. (2018), 87: 751-782 (Year: 2018).*
Cornish et al., Southern Hybridization Revisited; Probe/Target DNA Interaction is Affected by the Choice of Hybridization Buffer. BioTechniques (1998) 25: 948-954 (Year: 1998).*
Chapter 24, Biology 2e, OpenStax, https://openstax.org/details/books/biology-2e (Year: 2018).*
NCBI Reference Sequence: XP_006967324.1, glycosyltransferase [Trichoderma reesei QM6a], https://www.ncbi.nlm.nih.gov/protein/XP_006967324.1/ [retrieved Jan. 18, 2024] (Year: 2015).*
Lokhandwala et al., A Native Threonine Coordinates Ordered Water to Tune Light-Oxygen-Voltage (LOV) Domain Photocycle Kinetics andOsmotic Stress Signaling in Trichoderma reesei ENVOY. Journal of Biological Chemistry (2016), 291(28): 14839-14850 (Year: 2016).*
GlycosylTransferase Family 2, http://www.cazy.org/GT2.html, [retrieved Jan. 19, 2024] (Year: 2024).*
PF13632 https://www.ebi.ac.uk/interpro/entry/pfam/PF13632/, [retrieved Jan. 19, 2024] (Year: 2024).*
InterPro Pfam 13632 https://www.ebi.ac.uk/interpro/entry/pfam/PF13632/taxonomy/uniprot/#sunburst [retrieved May 21, 2024] (Year: 2024).*
International Search Report from PCT App. No. PCT/US2019/043348 dated Sep. 6, 2019, 8 pages.
King et al., "A conserved fungal glycosyltransferase facilitates pathogenesis of plants by enabling hyphal growth on solid surfaces", PLoS Pathology, 13(10), 2017, pp. 1-26.
Schmoll et al., "Envoy, a PAS/LOV Domain Protein of Hypocrea jecorina (Anamorph Trichoderma reesei), Modulates Cellulase Gene Transcription in Response to Light", Eularyotic Cell, vol. 4, No. 12, Dec. 1, 2005, pp. 1998-2007.
Zhang et al., "Improvement of cellulase production in Trichoderma reesei Rut-C30 by overexpression of a novel regulatory gene Trvib-1", Bioresource Technology, vol. 247, Sep. 20, 2017, pp. 676-683.

* cited by examiner

*Primary Examiner* — Celine X Qian
*Assistant Examiner* — Catherine Konopka

(57) ABSTRACT

The present strains and methods of the disclosure relate to genetic modifications in filamentous fungi that give rise to variant strains of filamentous fungi comprising enhanced protein productivity phenotypes. More specifically, as presented, described and exemplified herein, such variant strains of filamentous fungi comprising enhanced protein productivity phenotypes are well-suited for growth in submerged cultures, such as in large-scale production of proteins of interest for commercial applications.

8 Claims, 19 Drawing Sheets

Specification includes a Sequence Listing.

SEQ ID NO: 2 (*Trichoderma sp.*)
MGIGSYFKASTKNAEQAPPAPPPAKLAPPPRLQLEGRQSVMSEKPPSSTSGNDVDLQPPTPRFHSRPQSSSGRSTPSTQSSMFLDD
IKHEVMVNYLYQQQCSQLWVSDGSGEIEGVLLRKARGHYMACPPQLASSPFALACAALNVQCAMTVNSRVIKTFLQWSPDAVDVPL
MNGLRVQILPTIDDLPRARKYQFAAFVASEGLLVVWDDDALHLVARAKAIESELMELVWKAGNVDEEGGDEKGGQPVTEVEIDEES
GEIKPEKRPIHLQNTVLVSLTLALVTVSLGAAWRQLAIEVSVDSNYIRLALVALAPVQVFFTLFFAQVIIGCLAQIFGPIRQLTIN
SKFYSARPPPRLQSAVLPHVTIQCPVYKEGLQGVIMPTVKSIKQAMSTYELQGGSANMFINDDGLQLISEEDRLARIEFYADNSIG
WVARPKHGENGFTRKGKFKKASNMNFALMISCKVEEKLQAIERHPGWSQNDEALAYEEALKEVLEADGRAWADGNIRMGDYILLID
SDTRVPADCLLDAVSEMEQSPDVGIMQFSSGVMQVVHTYFENGITFFTNLIYSAIRYTVSNGDVAPFVGHNAILRWSAIQQVAYQD
EDGYDKFWSESHVSEDFDMSLRLQCNGYIIRLAAWAGEGFKEGVSLTVYDELARWEKYAYGCNELLFHPIRTWLWRGPFTPLFRRF
LFSNIRFTSKVTVISYIGTYYAIGAAWILTAVNYFVMGWFNGYLDKYYVDSWQVWFSIIIVFNGLGNIALAVMRYRVGERGLLYAL
FENFMWTLMLAIFLGGLSLHVSQALLAHMFEINMTWGATSKEAEFSNFFIEVPKVLKKFKFSMLFSLIFIAGMIILAQAPFVPFDW
RIKDFVAILPMATVAASHFLLPLALNPALMTFSW

SEQ ID NO: 11 (*Aspergillus sp.*)
MTMLSPTSDHPQGASMKDIENPGNDSPALEGSTQAEKTVDNPSRSPTPQLQTAELAQVLSPLAVRQTQSISTRSQHNRLEYLCLPN
ATNRGKLSRSLARRATLLGWFDQAATQSGQESQSSVCVAVKLPDDGYSFSPSNITPALSKAITRLNEMAVVALSSRVVDKGLSGIL
PGQKSFLVESTSTRIPIVATLDDVEPTLAHYSRACIVMEQKIVLVWSHDTAGILNVAYDVETQLGGQSPKISNATTPRISGRSTPM
DPYRTDDLQKPANVLQPVRGALDEKQAIYSKAVALEEGEDNEVPDLERNAAPRPVLLVHTVKISLAIMLVIVTQSLGVARLLNEFQ
WDGQYTRFALVVTIPPLALFSLFFFIVLVTSVFQLFLPASFCLKNSKFHSGDTEDSSAVKPNPKAHGEYELPHITIQMPVYKEGLK
GVIVPTMISVLAAVQYYEEQGGTASVFVNDDGMQVIQSDLAEARKQYYRENGIGFTARPPNKKSPVQKGGWGSWFRKSKPATTEPA
DSEEPEGPYTPQALANKIGFERKGKFKKASNMNYGLAFSLRVEDELARLTQIETERRGCTVDDLTAEDDDRLYQQALDNMLAADEE
RTWAEGNIRIGELILLIDCDTRVPVDCLLYGALEMHESPEVAILQHGSGVMQVVHNVFENGITYFTNVVYTAIKYGVGSGDVSPFV
GHNAFLRWRALQSIEFVDPSDGQTKWWSDTHVSEDFDISLRLQMQGMVVRLATYHNGEFKEGVSLTLYDELTRWEKYAYGCNELVF
HPFYQWVYKGPVTRLFLRFLWSNMPVTSKVTIIAYIFTYYAIGSGMLLATVNYVILGLFDSDIDHLYLPSWGIWCSLVVVFNGFSS
IAFSMVRHQLKEETFWRALLDAIKWLPFLIIYFGGISLNCAKAILCHAFSINLEWASTAKEMGPTGFYIGMDKMVRRFKWTWAICL
VLAGVMIYFAVGAPWGWTITPGPYSTANVAIAPLAIQICSASFLPFFLGLN

SEQ ID NO: 12 (*Penicillium sp.*)
MEEWPRNADEPYGSQRYQEDVQDLVSLPSRSSTPHLDRAEIGRVLSPSVQPGRNSRSRRSNPSIAHSFTSPSISESGEGEDPSSTA
RYLARRATLLGWFDEVDVEDGRNSWSSTCISLRRADNEYTFFPYNVNPSLIDAITRLGETAAMAMSSRFTSMLIDSILPGQKSLVV
ESTSARIPVVHSLNDVSSNLVHFARACIVVQEKLVLIWSHNAGTILHVAHDVERQLGKKSPRISTATTPRASGRSSPFDVDADVAP
STQISIKAKIDSFPVRGALDEKHEVYSKAVALEEGTVEDDTPVDLEGNLPPRPAHRIHAVKISLAIMLVILTQSLGVSRLVNEFAW
DGSFTRFALVVTIPPLALFSLFFFIVLVTSAFQLFLPASFCLKNSKFHSAIKPNPRFHRDYELPHITVQMPVYKEGLKGVIVPTMM
SVLAAVQYYEEQGGTASVFINDDGMQCIQPELAEARKQYYRENGIGYTARLPNRKTASKKKRGFGWFRKAKSAEGDAETEAEEDTS
SPQAIANKIGFERKGKFKKASNMNYGLAFSNRVEDELARLADLECQQRGCSNDDLTFEDDDRLYQQALSNMLAEDEGRTWAEGNVR
IGEIILIIDCDTRVPVDCLLYGALEMHESPEVAIVQHGSGVMQVVHNMFENGITYFTDVVYTAIKYGVGSGDVSPFVGHNAFLRWK
ALQSIQFVDPADGQTKWWSDAHVSEDFDISLRLQMQGMTVRLATYHNGGFKEGVSLTLYDELTRWEKYAYGCNELVFNPFYQWPYK
GPVTRLFLRFLWSNMPVTSKVTIIAYIFTYYAIASGMMLSVVNYVIVGLFNSEVDHIYLRSWGIWISLVVVFNGVASVAFSMARHQ
LKEMVFWKALLKSALWLPFLVVFFGGISLNCAKAILCHAFSINIEWASTAKEPGPSGFFIGLDKMVKQFKYTWAICLFLAAVMIFM
ALGTPWGWQIKPGEYSTASIAIGPLAIQICNAAILPLILGLN

SEQ ID NO: 13 (*Talaromyces sp.*)
MSSLFPTRWSFRGHKTPKGDGTPTETASQRDSLPVSESGRSSRGQGYFDRRHVNNSIDDASKYKAMIKFFHVRLTAYQWLPPPTHP
QHSSTGVFLRRSRGIYMSEPEDINPLLLAAIQRINATIAFTMMTETTSIITSQLAPGQTELILPNGYQVQIIESYADIVGSHSNMV
KKYQYAALIREEQLLLVWNDDLNAILNHAADVEGKLLSLIWGSPIPTFNLQAVPMMTPGESVVASPNDSLYHLALEPRESPAAAED
SGTSRDASPRRMINEEVKRPKESLERPLAVTSAIFVGMAGMLLVILLLGFGISNLLLEYSVDGGAMRFALTATIPFFLLFSIFFMI
VIFTDIFQAVGPVKTLKSNSRFYSPIAPDLKTAYSLGFTPPRVTIQMPIYTESLEGVIKPTISSLKTAISHYESHGGTANIFINDD
GFALLSEEQQHERINFYHDNNIGWVARPKNNEDGYIRKGKFKKASNMNFALNVSNKVEMELIQRMAPTLEKSDMVDPMEEELVYRE
AFDHVIQSDPRIRGAGGDIRVGEFILIVDSDTRIPADCLLYGAAEMFLSPEVAIIQHSTSVMQVSQDYFENGITYFTNLIYSAIRF
AVGSGETAPFVGHNAFLRWQAVQSVGRPDDGYVSFWSESHVSEDFDIALRLQIQGNIIRLASYHNDEFKEGVSLTIYDELSRWEKY
AYGCNELVFNPVHTWFYRGPLTKLFMTFLWSNLQLSSKITILGYISSYYALASGFPLTVLNYFLVGWFEGYLDKFYMESWKVFLSL
LVVFSAAGNVCLAIIRYRLGEKPLLASLVENFMWMPMFAIFFGGLSFHLSLAILSHMFGINMSWGTTAKEKDDSNFFKEIPKIFKS
FKWMYAVVLPFFPAMIYLACFAPNGWTITEVGAIVPMSVTLASHALLPLLLNPSLMVFNY

FIG. 7A

SEQ ID NO: 14 (*Fusarium sp.*)
MGIGSYFKADIPPQTPIGPPPRRPSHRPSMSLHAPIIEEKIPPAAVVELHSAAGPKFTAGPPSIAPSSKSGNSNLLDDIKHEVMVN
YLYQQQCSQLWVGDGSGEIEGVLLRKSRGQYMACPPQLGQSPFAIACTALNVQCAMTVNSRVIKTFLQWSPDAVDVPLMNGLRVQI
LPTVNDLPRARKHQFAAFIASDGLLVVWDDDALNLMARAKIIESELMELVWNSGQSVDEDERDSTIAAEYEIDEESGEIKPEARPV
HLQNAVLVSLTLLLVMASLGAAWRQLAVEIAIDGDYKRLGLVALFPIQIFFSLFFAQVIVGCLAQIFGPIRQLTINSKFYSARPPR
RLQGATLPHITIQCPVYKEGLNAVILPTVKSIKQAMSTYELQGGSANMFINDDGLQLLSEEERDARIDFYADNSIGWVARPKHGED
GFIRKGKFKKASNMNFGLMISCKVEERLQLIKRPADWSQSDEALAYEQALKDVLEENGRAWADGNIRVGDYILLIDSDTRVPTDCL
LDSVSEMEQSPDVGIMQFSSGVMQVVHTYFENGITFFTDLIYTAIRFTVSNGDVAPFVGHNAILRWSAIQQVAYQDEDGYDKFWSE
SHVSEDFDMSLRLQCNGYIIRLAAWAGDGFKEGVSLTVYDELARWEKYAFGCNELLFNPIRTWLWRGPFTPLFRRFCFSNIRFTSK
ITVVSYIGTYYAIGAAWIMTTANYFLMGWFNGYLDKYYLDSWQVWFSIILVFNGLGNLALAIMRYRSGERTLGYAIYENFKWTLML
AVFLGGLSLHVSQALLAHMFEIDMSWGSTSKEAEFSNFFIEVPKVLKKFRVSMTLSLLAIVALIIMATADFIPHYWRINDFVAILP
MATVAGSHLLLPLALNPALMTFSW

SEQ ID NO: 15 (*Myceliophthora sp.*)
MGIGDYFKAEKLGSKPTPTPASPPREHGRHQQQPSASEDHPAPSVQPASELQPPTPRFSSRPQSISGRSVRSTGSSVLDEIKHEVM
VNYLYQQQCSHLWISDGSGEIEGVLLRKARGQYMACPPQLVNSPLAAACTALNVQCAMTVNSRVIKTFLQWSPDAVDVPLMNGMRV
QILATIDDLPRARKHQFAAFVASEGLLIVWDDDALHLVQRAKAIESELMELVWKVGAEDNEDEKGVAAVEEPEVDEESGELKPEKR
PVHLLNAYLVSLSLILVTVSLGAAFRQLAIEVSVDGNYVRLALVALFPVQMFFTLFFAQVIVGCLAQIFGPIRQLTVNSKFYSARP
PPRLRSSVLPHVTVQCPVYKEGLNAVIAPTVKSIKQAMSTYELQGGSANMFINDDGLQLISEEDRRARIEFYADNSIGWVARPKHG
ENGFQRRGKFKKASNMNFALMISCKVEDKLAAIQRTPDWTQHDEALAYERALKEVLEEDGRAWADGNIRIGDYILLVDSDTRVPAD
CLLDAVSEMELSPDVGIMQFSSGVMQVVHTYFENGITFFTNLIYSAIRYTVSNGDVAPFVGHNAILRWSAIQQVSYEDEDGYEKFW
SESHVSEDFDMSLRLQCAGYIIRLAAWAGDGFKEGVSLTVYDELARWEKYAYGCNELLFHPIRKWIYKGPFTPLFRRFLFSNIRFT
SKVTVISYIGTYYAIAAAWIMTSINYFIMGWFNGYLDKYYVDSWQVWFSIILVFNGLGNIALAVMRYRVGERSILYALYENFKWTF
LLAVFLGGLSLHLSQALLAHMFEIDMTWGATAKEAEFSNFFIEVPKVLKKFKISMLFATIFIAGMIILAVAPFIPYSWHIKDFVAI
LPMATVAASHLLLPLVLNPALMTFS

SEQ ID NO: 16 (*Neurospora sp.*)
MGIGSYFKAKKPEPAGQQHAASTPSRGRQPSMGNTKAGQDDGDILAPPQIRYGSRSRSATRSMMSSTSSVILEDIKHEVMVNYLYQ
QQCSYLWVANGSGEIEGVLLRKSRGQYMACPPALGNSPFAMACAALNVQCAMTVNSRVIKTFLQWSPDAVDVPLLNGLRVQILPTI
EDLPRARKHQFAAFIASEGLLVVWDDDALHLIPRAKEIESELMQLVWKTGEPGEMDEKANPIVGATEIDEESGEPRPEARPVHLLN
TYLVSITMAVVTVSLGAAWRQLAIEVMVDGDYVRLALVALAPVQIFFTLFFAQVIIGCLAQIFGPIKQLSVNSRFYSAKPPPRLQT
AVLPHVTVQCPVYKEGLSGVIAPTVKSIKHAMSTYELQGGSANMFINDDGLQLLSEEDRQARIDFYADHSIGWVARPRHGENGFQR
RGKFKKASNMNYALMISCKVEEKLAQVPRHSEWSQHDEAQAYERALKDVLEENGRAWADGNIRMGDYILLIDSDTRVPSDCLLDAV
SEMEQSPDVGIMQFSSGVMQVVHTYFENGITFFTNLIYTAIRYTVSNGDVAPFVGHNAILRWSAIQQVSYEDEDGYEKFWSESHVS
EDFDMSLRLQCNDYIIRLAAWAGDGFKEGVSLTVYDELARWEKYAYGCNELLFYPIRKWIWKGPFTPLFRRFLFSNIRFTSKITII
SYIGTYYAIGAAWILTSVNYFLMGWYNGFLDKYYVDSWQVWFSIILVFNGLGNVALAVMRYRVGERSILGSILENFKWTLMLAIFL
GGLSLHVSQALLAHMFEIDMTWGATSKEAEFSNFFIEVPKVLKKFKFSMLFSIGFIIGMVILATAPFIPHSWHITDFVAILPMATV
AASHLLLPLALNPALMTFSW

SEQ ID NO: 17 (*Candida sp.*)
MGITDYFVSKGATEAKQGKNSTDIQQNETLTFPEMLAGPTGASPRAQFTIGETHLSSDIRTLQGHNEMISAGKSDFKDPQFIVVNY
LHDICLGNGWLKLVDPLEPCVVKMNSKKGNEIGYRYLPACDEIAPYSFVDCAARFLRSDVCVRVSFPVIHAILDILSSKGTVSLDA
DHNIQIIETVADLQWVRKSQNCAFIRNEKSLVCWADSVQEVTGFVRNLENKMVDYVWKKGNAVDVKGEDYVPRVTFASVFQSSSES
DVGSEGAVEIIGQNAVSQVSISEKSSDSSTHSDGNLNEKKNLDLEQQSSERPVIYIHATVSAFAITLVLAWAGLQFAQVTKEIRAE
GNYLILLSLLMVLPYFLFTSFFASSVMSTLLYVFGPISQMNKNSYSYSVHKAPRLKAAHGSLPHVTIQCPVYKEKLESVIKPTIKS
LQAAIRTYELQGGSANIFINDDGLQLIDRKEALERIEYYEECGLGYVARPGHGVNGFIRKGRFKKASNMNYCLHISKLVDTRFHER
LELIENPTPKEESGLYLKVLEEVVREEGKCWAGGDILLGDIILIIDSDTRVPEDCFVDSVSEMEQSPEVAIIQHASGVMMVVGNYW
EKMIAWFTNMIYFSISCVSGNGLTMAAFVGHNAFLRWSAIQELAYIDEDDGRTKYWSESHVSEDFEMTLKLASLGYTIRIATYHDG
GFKEGVSLTVYDEITRWSKYAFGCAEIMFSPFKDWWKGKIFARLFFVFLNSHISLPCKFSILGYMGTYYAIATSLIMLVANYFIVG
YYDWGYSRVYIDAMKVFVSVMVVFGCATQVAYIIGRYRIYKHSIYTMVLEFRYSILFSVFLGGLSWHMIVSIGSYFFSLNLQWGAT
AKDIDDSNFFKELPKAIKNYKFMYILCIFLIAGMIVLAFFVPYAFQIRLLTCALPLGWSVASHFLSPIVLNPQLMTFAW

FIG. 7B

CLUSTAL W (1.83) Multiple Sequence Alignment
SEQ ID NO: 2, residues 1-894 (bold single letter AA residues)

```
11     ------------------------------------------------------------
12     MEEWPRNADEPYGSQRYQEDVQDLVSLPSRSSTPHLDRAEIGRVLSPSVQPGRNSRSRRS
13     ------------------------------------------------------------
15     ------------------------------------------------------------
16     MGIGSYFKA---------KKPEPAGQQHAASTPSRGRQPSMGNTKAGQDDGD--ILAPPQ
2   (1)MGIGSYFKASTKNAEQAPPAPPPAKLAPPPRLQLEGRQSVMSEKPPSSTSGNDVDLQPPT
14     MGIGSYFKADIP---PQTPIGPPPRRPSHRPSMSLH--APIIEEKIPPAAVVELHSAAGPK
17     MGITDYFVSKGATEAKQGKNSTDIQQNETLTFPEMLAGPTGASPRAQFTIGETHLSSDIR

11     ------------------------------------------------------------
12     NPSIAHSFTSPSISESGEGEDPSSTARYLARRAT--LLGWFDEVDVEDGRNSWSSTCISL
13     ------------------------------------------------------------
15     ------------------------------------------------------------
16     IRYGSRSRSAT-RSMMSSTSSVILEDIKHEVMVN--YLYQQQCSYLWVANGSGEIEGVLL
2      PRFHSRPQSSSGRSTPSTQSSMFLDDIKHEVMVN--YLYQQQCSQLWVSDGSGEIEGVLL
14     FTAGPPSIAPSSKSGNSN----LLDDIKHEVMVN--YLYQQQCSQLWVGDGSGEIEGVLL
17     TLQGHNEMISAGKSDFKDPQFIVVNYLHDICLGNGWLKLVDPLEPCVVKMNSKKGNEIGY

11     ------------------------------------------------------------
12     RRADNEYTFFPYNVNPS-LIDAITRLGETAAMAMSSRFTSMLIDSILPGQKSLVVESTSA
13     ------------------------------------------------------------
15     ------------------------------------------------------------
16     RKSRGQYMACPPALGNSPFAMACAALNVQCAMTVNSRVIKTFLQWSPDAVDVPLLN--GL
2      RKARGHYMACPPQLASSPFALACAALNVQCAMTVNSRVIKTFLQWSPDAVDVPLMN--GL
14     RKSRGQYMACPPQLGQSPFAIACTALNVQCAMTVNSRVIKTFLQWSPDAVDVPLMN--GL
17     RYLPACDEIAPYSFVDCAARFLRSDVCVRVSFPVIHAILDILSSKGTVSLDA------DH

11     ------------------------------------------------------------
12     RIPVVHSLNDVSSNLVHFARACIVVQEKLVLIWSHNAGTILHVAHDVERQLGKKSPRIST
13     ------------------------------------------------------------
15     ------------------------------------------------------------
16     RVQILPTIEDLPR-ARKHQFAAFIASEGLLVVWDDDALHLIPRAKEIESELMQLVWKTGE
2      RVQILPTIDDLPR-ARKYQFAAFVASEGLLVVWDDDALHLVARAKAIESELMELVWKAGN
14     RVQILPTVNDLPR-ARKHQFAAFIASDGLLVVWDDDALNLMARAKIIESELMELVWNSGQ
17     NIQIIETVADLQW-VRKSQNCAFIRNEKSLVCWADSVQEVTGFVRNLENKMVDYVWKKGN

11     ------------------------------------------------------------
12     ATTPRASGRSSPFDVDADVAPSTQISIKAKIDSFPVRG---ALDEKHEVYSKAVALEEGT
13     ------------------------------------------------------------
15     ------------------------------------------------------------
16     PGEM--DEKANPIVGATEIDE---------------------------------------
2      VDEEGGDEKGGQPVTEVEIDE---------------------------------------
14     SVDE--DERDSTIAAEYEIDE---------------------------------------
17     AVDVKGEDYVPRVTFASVFQSSSESDVGSEGAVEIIGQNAVSQVSISEKSSDSSTHSDGN
```

FIG. 7C

CLUSTAL W (1.83) Multiple Sequence Alignment
SEQ ID NO: 2, residues 1-894 (bold single letter AA residues)—*Continued*

```
11      ----------------------------------------------------------
12      VEDDTPVDLEGNLPPRPAHRIHAVKISLAIMLVILTQSLGVSRLVNEFAWDGSFTRFALV
13      ----------------------------------------------------------
15      ----------------------------------------------------------
16      ------ESGEPRPEARPVHLLNTYLVSITMAVVTVSLGAAWRQLAIEVMVDGDYVRLALV
2       ------ESGEIKPEKRPIHLQNTVLVSLTLALVTVSLGAAWRQLAIEVSVDSNYIRLALV
14      ------ESGEIKPEARPVHLQNAVLVSLTLLLVMASLGAAWRQLAVEIAIDGDYKRLGLV
17      LNEKKNLDLEQQSSERPVIYIHATVSAFAITLVLAWAGLQFAQVTKEIRAEGNYLILLSL

11      ----------------------------------------------------------
12      VTIPPLALFSLFFFIVLVTSAFQLFLPASFCLKNSKFHSAIKPNPRFHRDYELPHITVQM
13      ----------------------------------------------------------
15      ----------------------------------------------------------
16      ALAPVQIFFTLFFAQVIIGCLAQIFGPIKQLSVNSRFYSAKPPPRLQT--AVLPHVTVQC
2       ALAPVQVFFTLFFAQVIIGCLAQIFGPIRQLTINSKFYSARPPPRLQS--AVLPHVTIQC
14      ALFPIQIFFSLFFAQVIVGCLAQIFGPIRQLTINSKFYSARPPRRLQG--ATLPHITIQC
17      LMVLPYFLFTSFFASSVMSTLLYVFGPISQMNKNSYSYSVHKAPRLKAAHGSLPHVTIQC

11      ----------------------------------------------------------
12      PVYKEGLKGVIVPTMMSVLAAVQYYEEQGGTASVFINDDGMQCIQPELAEARKQYYRENG
13      ----------------------------------------------------------
14      ----------------------------------------------------------
15      PVYKEGLSGVIAPTVKSIKHAMSTYELQGGSANMFINDDGLQLLSEEDRQARIDFYADHS
2       PVYKEGLQGVIMPTVKSIKQAMSTYELQGGSANMFINDDGLQLISEEDRLARIEFYADNS
16      PVYKEGLNAVILPTVKSIKQAMSTYELQGGSANMFINDDGLQLLSEEERDARIDFYADNS
17      PVYKEKLESVIKPTIKSLQAAIRTYELQGGSANIFINDDGLQLIDRKEALERIEYYEECG

11      ----------KPATTEP---------------ADSEEPEGPYTPQALANKIGFERKGKFK
12      IGYTARLPNRKTASKKKRGFGWFRKAKSAEGDAETEAEEDTSSPQAIANKIGFERKGKFK
13      ----------------------------------------------------------
15      ----------------------------------------------------------
16      IG-------------------------------------WVARPRHGENGFQRRGKFK
2       IG-------------------------------------WVARPKHGENGFTRKGKFK
14      IG-------------------------------------WVARPKHGEDGFIRKGKFK
17      LG-------------------------------------YVARPGHGVNGFIRKGRFK

11      KASNMNYGLAFSLRVEDELARLTQIETERRGCTVDDLTAEDDDRLYQQALDNMLAADEER
12      KASNMNYGLAFSNRVEDELARLADLECQQRGCSNDDLTFEDDDRLYQQALSNMLAEDEGR
13      ----------------------------------EEELVYREAFDHVIQSDPRI
15      ----------------------------------------------------------
16      KASNMNYALMISCKVEEKLAQVPRHS---------EWSQHDEAQAYERALKDVLEEN-GR
2       KASNMNFALMISCKVEEKLQAIERHP---------GWSQNDEALAYEEALKEVLEAD-GR
14      KASNMNFGLMISCKVEERLQLIKRPA---------DWSQSDEALAYEQALKDVLEEN-GR
17      KASNMNYCLHISKLVDTRFHERLELIEN--------PTPKEESGLYLKVLEEVVREE-GK
```

FIG. 7D

CLUSTAL W (1.83) Multiple Sequence Alignment
SEQ ID NO: 2, residues 1-894 (bold single letter AA residues)—*Continued*

```
11      TWAEGNIRIGELILLIDCDTRVPVDCLLYGALEMHESPEVAILQHGSGVMQVVHNVFENG
12      TWAEGNVRIGEIILIIDCDTRVPVDCLLYGALEMHESPEVAIVQHGSGVMQVVHNMFENG
13      RGAGGDIRVGEFILIVDSDTRIPADCLLYGAAEMFLSPEVAIIQHSTSVMQVSQDYFENG
15      -----------------SDTRVPADCLLDAVSEMELSPDVGIMQFSSGVMQVVHTYFENG
16      AWADGNIRMGDYILLIDSDTRVPSDCLLDAVSEMEQSPDVGIMQFSSGVMQVVHTYFENG
 2      AWADGNIRMGDYILLIDSDTRVPADCLLDAVSEMEQSPDVGIMQFSSGVMQVVHTYFENG
14      AWADGNIRVGDYILLIDSDTRVPTDCLLDSVSEMEQSPDVGIMQFSSGVMQVVHTYFENG
17      CWAGGDILLGDIILIIDSDTRVPEDCFVDSVSEMEQSPEVAIIQHASGVMMVVGNYWEKM
                .***:* **::  ..  **   **:*.*:*..:.** *      :*:

11      ITYFTNVVYTAIKYGVGSG-DVSPFVGHNAFLRWRALQSIEFVDPSDGQTKWWSDTHVSE
12      ITYFTDVVYTAIKYGVGSG-DVSPFVGHNAFLRWKALQSIQFVDPADGQTKWWSDAHVSE
13      ITYFTNLIYSAIRFAVGSG-ETAPFVGHNAFLRWQAVQSVG--RPDDGYVSFWSESHVSE
15      ITFFTNLIYSAIRYTVSNG-DVAPFVGHNAILRWSAIQQVSY-EDEDGYEKFWSESHVSE
16      ITFFTNLIYTAIRYTVSNG-DVAPFVGHNAILRWSAIQQVSY-EDEDGYEKFWSESHVSE
 2      ITFFTNLIYSAIRYTVSNG-DVAPFVGHNAILRWSAIQQVAY-QDEDGYDKFWSESHVSE
14      ITFFTDLIYTAIRFTVSNG-DVAPFVGHNAILRWSAIQQVAY-QDEDGYDKFWSESHVSE
17      IAWFTNMIYFSISCVSGNGLTMAAFVGHNAFLRWSAIQELAYIDEDDGRTKYWSESHVSE
                *::**:::* :*    ..*   :.******:*** *:*.:       **   .:**::****

11      DFDISLRLQMQGMVVRLATYHNGEFKEGVSLTLYDELTRWEKYAYGCNELVFHPFYQWVY
12      DFDISLRLQMQGMTVRLATYHNGGFKEGVSLTLYDELTRWEKYAYGCNELVFNPFYQWPY
13      DFDIALRLQIQGNIIRLASYHNDEFKEGVSLTIYDELSRWEKYAYGCNELVFNPVHTWFY
15      DFDMSLRLQCAGYIIRLAAWAGDGFKEGVSLTVYDELARWEKYAYGCNELLFHPIRKWIY
16      DFDMSLRLQCNDYIIRLAAWAGDGFKEGVSLTVYDELARWEKYAYGCNELLFYPIRKWIW
 2      DFDMSLRLQCNGYIIRLAAWAGEGFKEGVSLTVYDELARWEKYAYGCNELLFHPIRTWLW
14      DFDMSLRLQCNGYIIRLAAWAGDGFKEGVSLTVYDELARWEKYAFGCNELLFNPIRTWLW
17      DFEMTLKLASLGYTIRIATYHDGGFKEGVSLTVYDEITRWSKYAFGCAEIMFSPFKDWWK
                **::::*:*   . :*:*::  .  ********:***::**.***:** *:* *.  *

11      KGPVTRLFLRFLWSNMPVTSKVTIIAYIFTYYAIGSGMLLATVNYVILGLFDSDIDHLYL
12      KGPVTRLFLRFLWSNMPVTSKVTIIAYIFTYYAIASGMMLSVVNYVIVGLFNSEVDHIYL
13      RGPLTKLFMTFLWSNLQLSSKITILGYISSYYALASGFPLTVLNYFLVGWFEGYLDKFYM
15      KGPFTPLFRRFLFSNIRFTSKVTVISYIGTYYAIAAAWIMTSINYFIMGWFNGYLDKYYV
16      KGPFTPLFRRFLFSNIRFTSKITIISYIGTYYAIGAAWILTSVNYFLMGWYNGFLDKYYV
 2      RGPFTPLFRRFLFSNIRFTSKVTVISYIGTYYAIGAAWILTAVNYFVMGWFNGYLDKYYV
14      RGPFTPLFRRFCFSNIRFTSKITVVSYIGTYYAIGAAWIMTTANYFLMGWFNGYLDKYYL
17      GKIFARLFFVFLNSHISLPCKFSILGYMGTYYAIATSLIMLVANYFIVGYYDWGYSRVYI
                .:  **    *   *::   ...*.:::.*: :***:.:.    :   **.::* ::     .: *:

11      PSWGIWCSLVVVFNGFSSIAFSMVRHQLKEETFWRALLDAIKWLPFLIIYFGGISLNCAK
12      RSWGIWISLVVVFNGVASVAFSMARHQLKEMVFWKALLKSALWLPFLVVFFGGISLNCAK
13      ESWKVFLSLLVVFSAAGNVCLAIIRYRLGEKPLLASLVENFMWMPMFAIFFGGLSFHLSL
15      DSWQVWFSIILVFNGLGNIALAVMRYRVGERSILYALYENFKWTFLLAVFLGGLSLHLSQ
16      DSWQVWFSIILVFNGLGNVALAVMRYRVGERSILGSILENFKWTLMLAIFLGGLSLHVSQ
 2      DSWQVWFSIIIVFNGLGNIALAVMRYRVGERGLLYALFENFMWTLMLAIFLGGLSLHVSQ
14      DSWQVWFSIILVFNGLGNLALAIMRYRSGERTLGYAIYENFKWTLMLAVFLGGLSLHVSQ
17      DAMKVFVSVMVVFGCATQVAYIIGRYRIYKHSIYTMVLE-FRYSILFSVFLGGLSWHMIV
                :  ::  *:::**.   ...   :   *::    :   :.    :    ::  :::*:*.  :
```

FIG. 7E

CLUSTAL W (1.83) Multiple Sequence Alignment
SEQ ID NO: 2, residues 1-894 (bold single letter AA residues)—*Continued*

```
11    AILCHAFSINLEWAST̲AKEMGPTGFYIGMDKMVRRFKWTWAICLVLAGVMIYFAVG--AP
12    AILCHAFSINIEWAST̲AKEPGPSGFFIGLDKMVQFKYTWAICLFLAAVMIFMALG---TP
13    AILSHMFGINMSWGTT̲AKEKDDSNFFKEIPKIFKSFKWMYAVVLPFFPAMIYLACF--AP
15    ALLAHMFEIDMTWGAT̲AKEAEFSNFFIEVPKVLKKFKISMLFATIFIAGMIILAVAPFIP
16    ALLAHMFEIDMTWGAT̲SKEAEFSNFFIEVPKVLKKFKFSMLFSIGFIIGMVILATAPFIP
 2    ALLAHMFEINMTWGAT̲SKEAEFSNFFIEVPKVLKKFKFSMLFSLIFIAGMIILAQAPFVP
14    ALLAHMFEIDMSWGST̲SKEAEFSNFFIEVPKVLKKFRVSMTLSLLAIVALIIMATADFIP
17    SIGSYFFSLNLQWGAT̲AKDIDDSNFFKELPKAIKNYKFMYILCIFLIAGMIVLAFF--VP
      ::  .: *  ::: *.:*:*:    :.*:  : * .: ::    .    ::  :*     *

11    WGWTITPGPYSTANVAIAPLAIQICSASFLPFFLGLN------
12    WGWQIKPGEYSTASIAIGPLAIQICNAAILPLILGLN------
13    NGWTIT-------EVGAIVPMSVTLASHALLPLLLNPSLMVFNY
15    YSWHIK------DFVAILPMATVAASHLLLPLVLNPALMTFS-
16    HSWHIT------DFVAILPMATVAASHLLLPLALNPALMTFSW
 2    FDWRIK------DFVAILPMATVAASHFLLPLALNPALMTFSW(894)
14    HYWRIN------DFVAILPMATVAGSHLLLPLALNPALMTFSW
17    YAFQIR------LLTCALPLGWSVASHFLSPIVLNPQLMTFAW
       .*         .  *..  . : *.*.
```

FIG. 7F

SEQ ID NO: 18 (*Trichoderma sp.* LOV protein C-terminal residue positions 500-894)
AWADGNIRMGDYILLIDSDTRVPADCLLDAVSEMEQSPDVGIMQFSSGVMQVVHTYFENGITFFTNLIYSAIRYTVS
NGDVAPFVGHNAILRWSAIQQVAYQDEDGYDKFWSESHVSEDFDMSLRLQCNGYIIRLAAWAGEGFKEGVSLTVYDE
LARWEKYAYGCNELLFHPIRTWLWRGPFTPLFRRFLFSNIRFTSKVTVISYIGTYYAIGAAWILTAVNYFVMGWFNG
YLDKYYVDSWQVWFSIIIVFNGLGNIALAVMRYRVGERGLLYALFENFMWTLMLAIFLGGLSLHVSQALLAHMFEIN
MTWGATSKEAEFSNFFIEVPKVLKKFKFSMLFSLIFIAGMIILAQAPFVPFDWRIKDFVAILPMATVAASHFLLPLA
LNPALMTFSW SEQ ID NO: 11 (*Aspergillus* sp. LOV protein orthologue)
MTMLSPTSDHPQGASMKDIENPGNDSPALEGSTQAEKTVDNPSRSPTPQLQTAELAQVLSPLAVRQTQSISTRSQHN
RLEYLCLPNATNRGKLSRSLARRATLLGWFDQAATQSGQESQSSVCVAVKLPDDGYSFSPSNITPALSKAITRLNEM
AVVALSSRVVDKGLSGILPGQKSFLVESTSTRIPIVATLDDVEPTLAHYSRACIVMEQKIVLVWSHDTAGILNVAYD
VETQLGGQSPKISNATTPRISGRSTPMDPYRTDDLQKPANVLQPVRGALDEKQAIYSKAVALEEGEDNEVPDLERNA
APRPVLLVHTVKISLAIMLVIVTQSLGVARLLNEFQWDGQYTRFALVVTIPPLALFSLFFFIVLVTSVFQLFLPASF
CLKNSKFHSGDTEDSSAVKPNPKAHGEYELPHITIQMPVYKEGLKGVIVPTMISVLAAVQYYEEQGGTASVFNDDG
MQVIQSDLAEARKQYYRENGIGFTARPPNKKSPVQKGGWGSWFRKSKPATTEPADSEEPEGPYTPQALANKIGFERK
GKFKKASNMNYGLAFSLRVEDELARLTQIETERRGCTVDDLTAEDDDRLYQQALDNMLAADEERTWAEGNIRIGELI
LLIDCDTRVPVDCLLYGALEMHESPEVAILQHGSGVMQVVHNVFENGITYFTNVVYTAIKYGVSGDVSPFVGHNAF
LRWRALQSIEFVDPSDGQTKWWSDTHVSEDFDISLRLQMQGMVVRLATYHNGEFKEGVSLTLYDELTRWEKYAYGCN
ELVFHPFYQWVYKGPVTRLFLRFLWSNMPVTSKVTIIAYIFTYYAIGSGMLLATVNYVILGLFDSDIDHLYLPSWGI
WCSLVVVFNGFSSIAFSMVRHQLKEETFWRALLDAIKWLPFLIIYFGGISLNCAKAILCHAFSINLEWASTAKEMGP
TGFYIGMDKMVRRFKWTWAICLVLAGVMIYFAVGAPWGWTITPGPYSTANVAIAPLAIQICSASFLPFFLGLN

| Score | Expect | Method | Identities | Positives | Gaps |
|---|---|---|---|---|---|
| 409 bits(1052) | 9e-139 | Compositional matrix | 201/395(51%) | 273/395(69%) | 11/395(2%) |

```
Query  501  WADGNIRMGDYILLIDSDTRVPADCLLDAVSEMEQSPDVGIMQFSSGVMQVVHTYFENGI  560
            WA+GNIR+G+ ILLID DTRVP DCLL   EM +SP+V I+Q SGVMQVVH  FENGI
Sbjct  605  WAEGNIRIGELILLIDCDTRVPVDCLLYGALEMHESPEVAILQHGSGVMQVVHNVFENGI  664

Query  561  TFFFTNLIYSAIRYTVSNGDVAPFVGHNAILRWSAIQQVAYQD-EDGYDKFWSESHVSEDF  619
            T+FTN++Y+AI+Y V +GDV+PFVGHNA LRW A+Q + + D  DG K+WS++HVSEDF
Sbjct  665  TYFTNVVYTAIKYGVSGDVSPFVGHNAFLRWRALQSIEFVDPSDGQTKWWSDTHVSEDF  724

Query  620  DMSLRLQCNGYIIRLAAWAGEGFKEGVSLTVYDELARWEKYAYGCNELLFHPIRTWLWRG  679
            D+SLRLQ  G ++RLA +    FKEGVSLT+YDEL RWEKYAYGCNEL+FHP   W+++G
Sbjct  725  DISLRLQMQGMVVRLATYHNGEFKEGVSLTLYDELTRWEKYAYGCNELVFHPFYQWVYKG  784

Query  680  PFTPLFRRFLFSNIRFTSKVTVISYIGTYYAIGAAWILTAVNYFVMGWFNGYLDKYYVDS  739
            P T LF RFL+SN+  TSKVT+I+YI TYYAIG+ +L VNY ++G F+  +D Y+ S
Sbjct  785  PVTRLFLRFLWSNMPVTSKVTIIAYIFTYYAIGSGMLLATVNYVILGLFDSDIDHLYLPS  844

Query  740  WQVWFSIIIVFNGLGNIALAVMRYRVGERGLLYALFENFMWTLMLAIFLGGLSLHVSQAL  799
            W +W S+++VFNG +IA +++R+++  E   AL +   W  L I+ GG+SL+ ++A+
Sbjct  845  WGIWCSLVVVFNGFSSIAFSMVRHQLKEETFWRALLDAIKWLPFLIIYFGGISLNCAKAI  904

Query  800  LAHMFEINMTWGATSKEAEFSNFFIEVPKVLKKFKFSMLFSLIFIAGMIILAQAPFVPFD  859
            L H F  IN+ W +T+KE   + F+I + K++++FK++   L+   MI A    P+
Sbjct  905  LCHAFSINLEWASTAKEMGPTGFYIGMDKMVRRFKWTWAICLVLAGVMIYFAVG--APWG  962

Query  860  WRIKD------FVAILPMATVAASHFLLP--LALN  886
            W I         VAI P+A  S   LP  L LN
Sbjct  963  WTITPGPYSTANVAIAPLAIQICSASFLPFFLGLN  997
```

FIG. 8A

SEQ ID NO: 18 (*Trichoderma sp.* LOV protein C-terminal residue positions 500-894)
```
AWADGNIRMGDYILLIDSDTRVPADCLLDAVSEMEQSPDVGIMQFSSGVMQVVHTYFENGITFFTNLIYSAIRYTVS
NGDVAPFVGHNAILRWSAIQQVAYQDEDGYDKFWSESHVSEDFDMSLRLQCNGYIIRLAAWAGEGFKEGVSLTVYDE
LARWEKYAYGCNELLFHPIRTWLWRGPFTPLFRRFLFSNIRFTSKVTVISYIGTYYAIGAAWILTAVNYFVMGWFNG
YLDKYYVDSWQVWFSIIIVFNGLGNIALAVMRYRVGERGLLYALFENFMWTLMLAIFLGGLSLHVSQALLAHMFEIN
MTWGATSKEAEFSNFFIEVPKVLKKFKFSMLFSLIFIAGMIILAQAPFVPFDWRIKDFVAILPMATVAASHFLLPLA
LNPALMTFSW
```

SEQ ID NO: 12 (*Penicillium sp.* LOV protein orthologue)
```
MEEWPRNADEPYGSQRYQEDVQDLVSLPSRSSTPHLDRAEIGRVLSPSVQPGRNSRSRRSNPSIAHSFTSPSISESG
EGEDPSSTARYLARRATLLGWFDEVDVEDGRNSWSSTCISLRRADNEYTFFPYNVNPSLIDAITRLGETAAMAMSSR
FTSMLIDSILPGQKSLVVESTSARIPVVHSLNDVSSNLVHFARACIVVQEKLVLIWSHNAGTILHVAHDVERQLGKK
SPRISTATTPRASGRSSPFDVDADVAPSTQISIKAKIDSFPVRGALDEKHEVYSKAVALEEGTVEDDTPVDLEGNLP
PRPAHRIHAVKISLAIMLVILTQSLGVSRLVNEFAWDGSFTRFALVVTIPPLALFSLFFFIVLVTSAFQLFLPASFC
LKNSKFHSAIKPNPRFHRDYELPHITVQMPVYKEGLKGVIVPTMMSVLAAVQYYEEQGGTASVFINDDGMQCIQPEL
AEARKQYYRENGIGYTARLPNRKTASKKKRGFGWFRKAKSAEGDAETEAEEDTSSPQAIANKIGFERKGKFKKASNM
NYGLAFSNRVEDELARLADLECQQRGCSNDDLTFEDDDRLYQQALSNMLAEDEGRTWAEGNVRIGEIILIIDCDTRV
PVDCLLYGALEMHESPEVAIVQHGSGVMQVVHNMFENGITYFTDVVYTAIKYGVGSGDVSPFVGHNAFLRWKALQSI
QFVDPADGQTKWWSDAHVSEDFDISLRLQMQGMTVRLATYHNGGFKEGVSLTLYDELTRWEKYAYGCNELVFNPFYQ
WPYKGPVTRLFLRFLWSNMPVTSKVTIIAYIFTYYAIASGMMLSVVNYVIVGLFNSEVDHIYLRSWGIWISLVVVFN
GVASVAFSMARHQLKEMVFWKALLKSALWLPFLVVFFGGISLNCAKAILCHAFSINIEWASTAKEPGPSGFFIGLDK
MVKQFKYTWAICLFLAAVMIFMALGTPWGWQIKPGEYSTASIAIGPLAIQICNAAILPLILGLN
```

| Score | Expect | Method | Identities | Positives | Gaps |
|---|---|---|---|---|---|
| 411 bits(1057) | 1e-139 | Compositional | 199/392(51%) | 277/392(70%) | 9/392(2%) |

```
Query  501  WADGNIRMGDYILLIDSDTRVPADCLLDAVSEMEQSPDVGIMQFSSGVMQVVHTYFENGI  560
            WA+GN+R+G+ IL+ID DTRVP DCLL   EM +SP+V I+Q SGVMQVVH  FENGI
Sbjct  596  WAEGNVRIGEIILIIDCDTRVPVDCLLYGALEMHESPEVAIVQHGSGVMQVVHNMFENGI  655

Query  561  TFFTNLIYSAIRYTVSNGDVAPFVGHNAILRWSAIQQVAYQDE-DGYDKFWSESHVSEDF  619
            T+FT+++Y+AI+Y V +GDV PFVGHNA LRW A+Q  + + D  DG  K+WS++HVSEDF
Sbjct  656  TYFTDVVYTAIKYGVGSGDVSPFVGHNAFLRWKALQSIQFVDPADGQTKWWSDAHVSEDF  715

Query  620  DMSLRLQCNGYIIRLAAWAGEGFKEGVSLTVYDELARWEKYAYGCNELLFHPIRTWLWRG  679
            D+SLRLQ  G +RLA +   GFKEGVSLT+YDEL RWEKYAYGCNEL+F+P   W ++G
Sbjct  716  DISLRLQMQGMTVRLATYHNGGFKEGVSLTLYDELTRWEKYAYGCNELVFNPFYQWPYKG  775

Query  680  PFTPLFRRFLFSNIRFTSKVTVISYIGTYYAIGAAWILTAVNYFVMGWFNGYLDKYYVDS  739
            P T LF RFL+SN+  TSKVT+I+YI TYYAI +  +L+ VNY ++G FN  +D Y+ S
Sbjct  776  PVTRLFLRFLWSNMPVTSKVTIIAYIFTYYAIASGMMLSVVNYVIVGLFNSEVDHIYLRS  835

Query  740  WQVWFSIIIVFNGLGNIALAVMRYRVGERGLLYALFENFMWTLMLAIFLGGLSLHVSQAL  799
            W +W S+++VFNG+ ++A ++ R+++ E    AL ++ +W   L +F GG+SL+ ++A+
Sbjct  836  WGIWISLVVVFNGVASVAFSMARHQLKEMVFWKALLKSALWLPFLVVFFGGISLNCAKAI  895

Query  800  LAHMFEINMTWGATSKEAEFSNFFIEVPKVLKKFKFSMLFSLIFIAGMIILAQAPFVPFD  859
            L H F IN+ W +T+KE   S FFI + K+++K+FK++    L   A MI +A   P+
Sbjct  896  LCHAFSINIEWASTAKEPGPSGFFIGLDKMVQFKYTWAICLFLAAVMIFMALG--TPWG  953

Query  860  WRIKD------FVAILPMATVAASHFLLPLAL  885
            W+IK        +AI P+A   + +LPL L
Sbjct  954  WQIKPGEYSTASIAIGPLAIQICNAAILPLIL  985
```

FIG. 8B

SEQ ID NO: 18 (*Trichoderma sp.* LOV protein C-terminal residue positions 500-894)
AWADGNIRMGDYILLIDSDTRVPADCLLDAVSEMEQSPDVGIMQFSSGVMQVVHTYFENGITFFTNLIYSAIRYTVS
NGDVAPFVGHNAILRWSAIQQVAYQDEDGYDKFWSESHVSEDFDMSLRLQCNGYIIRLAAWAGEGFKEGVSLTVYDE
LARWEKYAYGCNELLFHPIRTWLWRGPFTPLFRRFLFSNIRFTSKVTVISYIGTYYAIGAAWILTAVNYFVMGWFNG
YLDKYYVDSWQVWFSIIIVFNGLGNIALAVMRYRVGERGLLYALFENFMWTLMLAIFLGGLSLHVSQALLAHMFEIN
MTWGATSKEAEFSNFFIEVPKVLKKFKFSMLFSLIFIAGMIILAQAPFVPFDWRIKDFVAILPMATVAASHFLLPLA
LNPALMTFSW SEQ ID NO: 13 (*Talaromyces sp.* LOV protein orthologue)
MSSLFPTRWSFRGHKTPKGDGTPTETASQRDSLPVSESGRSSRGQGYFDRRHVNNSIDDASKYKAMIKFFHVRLTAY
QWLPPPTHPQHSSTGVFLRRSRGIYMSEPEDINPLLLAAIQRINATIAFTMMTETTSIITSQLAPGQTELILPNGYQ
VQIIESYADIVGSHSNMVKKYQYAALIREEQLLLVWNDDLNAILNHAADVEGKLLSLIWGSPIPTFNLQAVPMMTPG
ESVVASPNDSLYHLALEPRESPAAAEDSGTSRDASPRRMINEEVKRPKESLERPLAVTSAIFVGMAGMLLVILLGF
GISNLLLEYSVDGGAMRFALTATIPFFLLFSIFFMIVIFTDIFQAVGPVKTLKSNSRFYSPIAPDLKTAYSLGFTPP
RVTIQMPIYTESLEGVIKPTISSLKTAISHYESHGGTANIFINDDGFALLSEEQQHERINFYHDNNIGWVARPKNNE
DGYIRKGKFKKASNMNFALNVSNKVEMELIQRMAPTLEKSDMVDPMEEELVYREAFDHVIQSDPRIRGAGGDIRVGE
FILIVDSDTRIPADCLLYGAAEMFLSPEVAIIQHSTSVMQVSQDYFENGITYFTNLIYSAIRFAVGSGETAPFVGHN
AFLRWQAVQSVGRPDDGYVSFWSESHVSEDFDIALRLQIQGNIIRLASYHNDEFKEGVSLTIYDELSRWEKYAYGCN
ELVFNPVHTWFYRGPLTKLFMTFLWSNLQLSSKITILGYISSYYALASGFPLTVLNYFLVGWFEGYLDKFYMESWKV
FLSLLVVFSAAGNVCLAIIRYRLGEKPLLASLVENFMWMPMFAIFFGGLSFHLSLAILSHMFGINMSWGTTAKEKDD
SNFFKEIPKIFKSFKWMYAVVLPFFPAMIYLACFAPNGWTITEVGAIVPMSVTLASHALLPLLLNPSLMVFNY

```
Score              Expect          Method              Identities       Positives       Gaps
477 bits(1227)     9e-166          Compositional       222/377(59%)     290/377(76%)    3/377(0%)

Query  502   ADGNIRMGDYILLIDSDTRVPADCLLDAVSEMEQSPDVGIMQFSSGVMQVVHTYFENGIT   561
             A G+IR+G++IL++DSDTR+PADCLL  +EM  SP+V I+Q S+ VMQV   YFENGIT
Sbjct  531   AGGDIRVGEFILIVDSDTRIPADCLLYGAAEMFLSPEVAIIQHSTSVMQVSQDYFENGIT   590

Query  562   FFTNLIYSAIRYTVSNGDVAPFVGHNAILRWSAIQQVAYQDEDGYDKFWSESHVSEDFDM   621
             +FTNLIYSAIR+ V +G+ APFVGHNA LRW A+Q V   D DGY  FWSESHVSEDFD+
Sbjct  591   YFTNLIYSAIRFAVGSGETAPFVGHNAFLRWQAVQSVGRPD-DGYVSFWSESHVSEDFDI   649

Query  622   SLRLQCNGYIIRLAAWAGEGFKEGVSLTVYDELARWEKYAYGCNELLFHPIRTWLWRGPF   681
             +LRLQ  G IIRLA++  + FKEGVSLT+YDEL+RWEKYAYGCNEL+F+P+ TW +RGP
Sbjct  650   ALRLQIQGNIIRLASYHNDEFKEGVSLTIYDELSRWEKYAYGCNELVFNPVHTWFYRGPL   709

Query  682   TPLFRRFLFSNIRFTSKVTVISYIGTYYAIGAAWILTAVNYFVMGWFNGYLDKYYVDSWQ   741
             T LF  FL+SN++ +SK+T++  YI +YYA+ + +  LT +NYF++GWF GYLDK+Y++SW+
Sbjct  710   TKLFMTFLWSNLQLSSKITILGYISSYYALASGFPLTVLNYFLVGWFEGYLDKFYMESWK   769

Query  742   VWFSIIIVFNGLGNIALAVMRYRVGERGLLYALFENFMWTLMLAIFLGGLSLHVSQALLA   801
             V+ S+++VF+  GN  LA++RYR+GE+ LL +L ENFMW  M AIF GGLS H+S A+L+
Sbjct  770   VFLSLLVVFSAAGNVCLAIIRYRLGEKPLLASLVENFMWMPMFAIFFGGLSFHLSLAILS   829

Query  802   HMFEINMTWGATSKEAEFSNFFIEVPKVLKKFKFSMLFSLIFIAGMIILAQAPFVPFDWR   861
             HMF INM+WG  T+KE + SNFF E+PK+ K FK+     L F   MI LA    F  W
Sbjct  830   HMFGINMSWGTTAKEKDDSNFFKEIPKIFKSFKWMYAVVLPFFPAMIYLAC--FAPNGWT   887

Query  862   IKDFVAILPMATVAASH   878
             I +  AI+PM+   ASH
Sbjct  888   ITEVGAIVPMSVTLASH   904
```

FIG. 8C

SEQ ID NO: 18 (*Trichoderma sp.* LOV protein C-terminal residue positions 500-894)
AWADGNIRMGDYILLIDSDTRVPADCLLDAVSEMEQSPDVGIMQFSSGVMQVVHTYFENGITFFTNLIYSAIRYTVS
NGDVAPFVGHNAILRWSAIQQVAYQDEDGYDKFWSESHVSEDFDMSLRLQCNGYIIRLAAWAGEGFKEGVSLTVYDE
LARWEKYAYGCNELLFHPIRTWLWRGPFTPLFRRFLFSNIRFTSKVTVISYIGTYYAIGAAWILTAVNYFVMGWFNG
YLDKYYVDSWQVWFSIIIVFNGLGNIALAVMRYRVGERGLLYALFENFMWTLMLAIFLGGLSLHVSQALLAHMFEIN
MTWGATSKEAEFSNFFIEVPKVLKKFKFSMLFSLIFIAGMIILAQAPFVPFDWRIKDFVAILPMATVAASHFLLPLA
LNPALMTFSW SEQ ID NO: 14 (*Fusarium sp.* LOV protein orthologue)
MGIGSYFKADIPPQTPIGPPPRRPSHRPSMSLHAPIIEEKIPPAAVVELHSAAGPKFTAGPPSIAPSSKSGNSNLLD
DIKHEVMVNYLYQQQCSQLWVGDGSGEIEGVLLRKSRGQYMACPPQLGQSPFAIACTALNVQCAMTVNSRVIKTFLQ
WSPDAVDVPLMNGLRVQILPTVNDLPRARKHQFAAFIASDGLLVVWDDDALNLMARAKIIESELMELVWNSGQSVDE
DERDSTIAAEYEIDEESGEIKPEARPVHLQNAVLVSLTLLLVMASLGAAWRQLAVEIAIDGDYKRLGLVALFPIQIF
FSLFFAQVIVGCLAQIFGPIRQLTINSKFYSARPPRRLQGATLPHITIQCPVYKEGLNAVILPTVKSIKQAMSTYEL
QGGSANMFINDDGLQLLSEEEERDARIDFYADNSIGWVARPKHGEDGFIRKGKFKKASNMNFGLMISCKVEERLQLIK
RPADWSQSDEALAYEQALKDVLEENGRAWADGNIRVGDYILLIDSDTRVPTDCLLDSVSEMEQSPDVGIMQFSSGVM
QVVHTYFENGITFFTDLIYTAIRFTVSNGDVAPFVGHNAILRWSAIQQVAYQDEDGYDKFWSESHVSEDFDMSLRLQ
CNGYIIRLAAWAGDGFKEGVSLTVYDELARWEKYAFGCNELLFNPIRTWLWRGPFTPLFRRFCFSNIRFTSKITVVS
YIGTYYAIGAAWIMTTANYFLMGWFNGYLDKYYLDSWQVWFSIILVFNGLGNLALAIMRYRSGERTLGYAIYENFKW
TLMLAVFLGGLSLHVSQALLAHMFEIDMSWGSTSKEAEFSNFFIEVPKVLKKFRVSMTLSLLAIVALIIMATADFIP
HYWRINDFVAILPMATVAGSHLLLPLALNPALMTFSW

```
Score          Expect     Method         Identities     Positives      Gaps
717 bits(1852) 0.0        Compositional  347/395(88%)   374/395(94%)   0/395(0%)

Query  500  AWADGNIRMGDYILLIDSDTRVPADCLLDAVSEMEQSPDVGIMQFSSGVMQVVHTYFENG  559
            AWADGNIR+GDYILLIDSDTRVP DCLLD+VSEMEQSPDVGIMQFSSGVMQVVHTYFENG
Sbjct  490  AWADGNIRVGDYILLIDSDTRVPTDCLLDSVSEMEQSPDVGIMQFSSGVMQVVHTYFENG  549

Query  560  ITFFTNLIYSAIRYTVSNGDVAPFVGHNAILRWSAIQQVAYQDEDGYDKFWSESHVSEDF  619
            ITFFT+LIY+AIR+TVSNGDVAPFVGHNAILRWSAIQQVAYQDEDGYDKFWSESHVSEDF
Sbjct  550  ITFFTDLIYTAIRFTVSNGDVAPFVGHNAILRWSAIQQVAYQDEDGYDKFWSESHVSEDF  609

Query  620  DMSLRLQCNGYIIRLAAWAGEGFKEGVSLTVYDELARWEKYAYGCNELLFHPIRTWLWRG  679
            DMSLRLQCNGYIIRLAAWAG+GFKEGVSLTVYDELARWEKYA+GCNELLF+PIRTWLWRG
Sbjct  610  DMSLRLQCNGYIIRLAAWAGDGFKEGVSLTVYDELARWEKYAFGCNELLFNPIRTWLWRG  669

Query  680  PFTPLFRRFLFSNIRFTSKVTVISYIGTYYAIGAAWILTAVNYFVMGWFNGYLDKYYVDS  739
            PFTPLFRRF FSNIRFTSK+TV+SYIGTYYAIGAAWI+T  NYF+MGWFNGYLDKYY+DS
Sbjct  670  PFTPLFRRFCFSNIRFTSKITVVSYIGTYYAIGAAWIMTTANYFLMGWFNGYLDKYYLDS  729

Query  740  WQVWFSIIIVFNGLGNIALAVMRYRVGERGLLYALFENFMWTLMLAIFLGGLSLHVSQAL  799
            WQVWFSII+VFNGLGN+ALA+MRYR GER L YA++ENF WTLMLA+FLGGLSLHVSQAL
Sbjct  730  WQVWFSIILVFNGLGNLALAIMRYRSGERTLGYAIYENFKWTLMLAVFLGGLSLHVSQAL  789

Query  800  LAHMFEINMTWGATSKEAEFSNFFIEVPKVLKKFKFSMLFSLIFIAGMIILAQAPFVPFD  859
            LAHMFEI+M+WG+TSKEAEFSNFFIEVPKVLKKF+ SM  SL+ I  +II+A A F+P
Sbjct  790  LAHMFEIDMSWGSTSKEAEFSNFFIEVPKVLKKFRVSMTLSLLAIVALIIMATADFIPHY  849

Query  860  WRIKDFVAILPMATVAASHFLLPLALNPALMTFSW  894
            WRI DFVAILPMATVA SH LLPLALNPALMTFSW
Sbjct  850  WRINDFVAILPMATVAGSHLLLPLALNPALMTFSW  884
```

FIG. 8D

SEQ ID NO: 18 (*Trichoderma sp.* LOV protein C-terminal residue positions 500-894)
AWADGNIRMGDYILLIDSDTRVPADCLLDAVSEMEQSPDVGIMQFSSGVMQVVHTYFENGITFFTNLIYSAIRYTVS
NGDVAPFVGHNAILRWSAIQQVAYQDEDGYDKFWSESHVSEDFDMSLRLQCNGYIIRLAAWAGEGFKEGVSLTVYDE
LARWEKYAYGCNELLFHPIRTWLWRGPFTPLFRRFLFSNIRFTSKVTVISYIGTYYAIGAAWILTAVNYFVMGWFNG
YLDKYYVDSWQVWFSIIIVFNGLGNIALAVMRYRVGERGLLYALFENFMWTLMLAIFLGGLSLHVSQALLAHMFEIN
MTWGATSKEAEFSNFFIEVPKVLKKFKFSMLFSLIFIAGMIILAQAPFVPFDWRIKDFVAILPMATVAASHFLLPLA
LNPALMTFSW SEQ ID NO: 15 (*Myceliophthora sp.* LOV protein orthologue)
MGIGDYFKAEKLGSKPTPTPASPPREHGRHQQQPSASEDHPAPSVQPASELQPPTPRFSSRPQSISGRSVRSTGSSV
LDEIKHEVMVNYLYQQQCSHLWISDGSGEIEGVLLRKARGQYMACPPQLVNSPLAAACTALNVQCAMTVNSRVIKTF
LQWSPDAVDVPLMNGMRVQILATIDDLPRARKHQFAAFVASEGLLIVWDDDALHLVQRAKAIESELMELVWKVGAED
NEDEKGVAAVEEPEVDEESGELKPEKRPVHLLNAYLVSLSLILVTVSLGAAFRQLAIEVSVDGNYVRLALVALFPVQ
MFFTLFFAQVIVGCLAQIFGPIRQLTVNSKFYSARPPPRLSSVLPHVTVQCPVYKEGLNAVIAPTVKSIKQAMSTY
ELQGGSANMFINDDGLQLISEEDRRARIEFYADNSIGWVARPKHGENGFQRRGKFKKASNMNFALMISCKVEDKLAA
IQRTPDWTQHDEALAYERALKEVLEEDGRAWADGNIRIGDYILLVDSDTRVPADCLLDAVSEMELSPDVGIMQFSSG
VMQVVHTYFENGITFFTNLIYSAIRYTVSNGDVAPFVGHNAILRWSAIQQVSYEDEDGYEKFWSESHVSEDFDMSLR
LQCAGYIIRLAAWAGDGFKEGVSLTVYDELARWEKYAYGCNELLFHPIRKWIYKGPFTPLFRRFLFSNIRFTSKVTV
ISYIGTYYAIAAAWIMTSINYFIMGWFNGYLDKYYVDSWQVWFSIILVFNGLGNIALAVMRYRVGERSILYALYENF
KWTFLLAVFLGGLSLHLSQALLAHMFEIDMTWGATAKEAEFSNFFIEVPKVLKKFKISMLFATIFIAGMIILAVAPF
IPYSWHIKDFVAILPMATVAASHLLLPLVLNPALMTFS

| Score | Expect | Method | Identities | Positives | Gaps |
|---|---|---|---|---|---|
| 759 bits(1961) | 0.0 | Compositional | 356/394(90%) | 380/394(96%) | 0/394(0%) |

```
Query  500  AWADGNIRMGDYILLIDSDTRVPADCLLDAVSEMEQSPDVGIMQFSSGVMQVVHTYFENG  559
            AWADGNIR+GDYILL+DSDTRVPADCLLDAVSEME SPDVGIMQFSSGVMQVVHTYFENG
Sbjct  492  AWADGNIRIGDYILLVDSDTRVPADCLLDAVSEMELSPDVGIMQFSSGVMQVVHTYFENG  551

Query  560  ITFFTNLIYSAIRYTVSNGDVAPFVGHNAILRWSAIQQVAYQDEDGYDKFWSESHVSEDF  619
            ITFFTNLIYSAIRYTVSNGDVAPFVGHNAILRWSAIQQV Y+DEDGY+KFWSESHVSEDF
Sbjct  552  ITFFTNLIYSAIRYTVSNGDVAPFVGHNAILRWSAIQQVSYEDEDGYEKFWSESHVSEDF  611

Query  620  DMSLRLQCNGYIIRLAAWAGEGFKEGVSLTVYDELARWEKYAYGCNELLFHPIRTWLWRG  679
            DMSLRLQC GYIIRLAAWAG+GFKEGVSLTVYDELARWEKYAYGCNELLFHPIR W+++G
Sbjct  612  DMSLRLQCAGYIIRLAAWAGDGFKEGVSLTVYDELARWEKYAYGCNELLFHPIRKWIYKG  671

Query  680  PFTPLFRRFLFSNIRFTSKVTVISYIGTYYAIGAAWILTAVNYFVMGWFNGYLDKYYVDS  739
            PFTPLFRRFLFSNIRFTSKVTVISYIGTYYAI AAWI+T++NYF+MGWFNGYLDKYYVDS
Sbjct  672  PFTPLFRRFLFSNIRFTSKVTVISYIGTYYAIAAAWIMTSINYFIMGWFNGYLDKYYVDS  731

Query  740  WQVWFSIIIVFNGLGNIALAVMRYRVGERGLLYALFENFMWTLMLAIFLGGLSLHVSQAL  799
            WQVWFSII+VFNGLGNIALAVMRYRVGER +LYAL+ENF WT +LA+FLGGLSLH+SQAL
Sbjct  732  WQVWFSIILVFNGLGNIALAVMRYRVGERSILYALYENFKWTFLLAVFLGGLSLHLSQAL  791

Query  800  LAHMFEINMTWGATSKEAEFSNFFIEVPKVLKKFKFSMLFSLIFIAGMIILAQAPFVPFD  859
            LAHMFEI+MTWGAT+KEAEFSNFFIEVPKVLKKFK SMLF+ IFIAGMIILA APF+P+
Sbjct  792  LAHMFEIDMTWGATAKEAEFSNFFIEVPKVLKKFKISMLFATIFIAGMIILAVAPFIPYS  851

Query  860  WRIKDFVAILPMATVAASHFLLPLALNPALMTFS  893
            W IKDFVAILPMATVAASH LLPL LNPALMTFS
Sbjct  852  WHIKDFVAILPMATVAASHLLLPLVLNPALMTFS  885
```

FIG. 8E

SEQ ID NO: 18 (*Trichoderma sp.* LOV protein C-terminal residue positions 500-894)
AWADGNIRMGDYILLIDSDTRVPADCLLDAVSEMEQSPDVGIMQFSSGVMQVVHTYFENGITFFTNLIYSAIRYTVS
NGDVAPFVGHNAILRWSAIQQVAYQDEDGYDKFWSESHVSEDFDMSLRLQCNGYIIRLAAWAGEGFKEGVSLTVYDE
LARWEKYAYGCNELLFHPIRTWLWRGPFTPLFRRFLFSNIRFTSKVTVISYIGTYYAIGAAWILTAVNYFVMGWFNG
YLDKYYVDSWQVWFSIIIVFNGLGNIALAVMRYRVGERGLLYALFENFMWTLMLAIFLGGLSLHVSQALLAHMFEIN
MTWGATSKEAEFSNFFIEVPKVLKKFKFSMLFSLIFIAGMIILAQAPFVPFDWRIKDFVAILPMATVAASHFLLPLA
LNPALMTFSW SEQ ID NO: 16 (*Neurospora sp.* LOV protein orthologue)
MGIGSYFKAKKPEPAGQQHAASTPSRGRQPSMGNTKAGQDDGDILAPPQIRYGSRSRSATRSMMSSTSSVILEDIKH
EVMVNYLYQQQCSYLWVANGSGEIEGVLLRKSRGQYMACPPALGNSPFAMACAALNVQCAMTVNSRVIKTFLQWSPD
AVDVPLLNGLRVQILPTIEDLPRARKHQFAAFIASEGLLVVWDDDALHLIPRAKEIESELMQLVWKTGEPGEMDEKA
NPIVGATEIDEESGEPRPEARPVHLLNTYLVSITMAVVTVSLGAAWRQLAIEVMVDGDYVRLALVALAPVQIFFTLF
FAQVIIGCLAQIFGPIKQLSVNSRFYSAKPPPRLQTAVLPHVTVQCPVYKEGLSGVIAPTVKSIKHAMSTYELQGGS
ANMFINDDGLQLLSEEDRQARIDFYADHSIGWVARPRHGENGFQRRGKFKKASNMNYALMISCKVEEKLAQVPRHSE
WSQHDEAQAYERALKDVLEENGRAWADGNIRMGDYILLIDSDTRVPSDCLLDAVSEMEQSPDVGIMQFSSGVMQVVH
TYFENGITFFTNLIYTAIRYTVSNGDVAPFVGHNAILRWSAIQQVSYEDEDGYEKFWSESHVSEDFDMSLRLQCNDY
IIRLAAWAGDGFKEGVSLTVYDELARWEKYAYGCNELLFYPIRKWIWKGPFTPLFRRFLFSNIRFTSKITIISYIGT
YYAIGAAWILTSVNYFLMGWYNGFLDKYYVDSWQVWFSIILVFNGLGNVALAVMRYRVGERSILGSILENFKWTLML
AIFLGGLSLHVSQALLAHMFEIDMTWGATSKEAEFSNFFIEVPKVLKKFKFSMLFSIGFIIGMVILATAPFIPHSWH
ITDFVAILPMATVAASHLLLPLALNPALMTFSW

```
Score         Expect     Method         Identities     Positives     Gaps
735 bits(1898) 0.0       Compositional  357/395(90%)   381/395(96%)  0/395(0%)

Query  500  AWADGNIRMGDYILLIDSDTRVPADCLLDAVSEMEQSPDVGIMQFSSGVMQVVHTYFENG  559
            AWADGNIRMGDYILLIDSDTRVP+DCLLDAVSEMEQSPDVGIMQFSSGVMQVVHTYFENG
Sbjct  486  AWADGNIRMGDYILLIDSDTRVPSDCLLDAVSEMEQSPDVGIMQFSSGVMQVVHTYFENG  545

Query  560  ITFFTNLIYSAIRYTVSNGDVAPFVGHNAILRWSAIQQVAYQDEDGYDKFWSESHVSEDF  619
            ITFFTNLIY+AIRYTVSNGDVAPFVGHNAILRWSAIQQV+Y+DEDGY+KFWSESHVSEDF
Sbjct  546  ITFFTNLIYTAIRYTVSNGDVAPFVGHNAILRWSAIQQVSYEDEDGYEKFWSESHVSEDF  605

Query  620  DMSLRLQCNGYIIRLAAWAGEGFKEGVSLTVYDELARWEKYAYGCNELLFHPIRTWLWRG  679
            DMSLRLQCN YIIRLAAWAG+GFKEGVSLTVYDELARWEKYAYGCNELLF+PIR W+W+G
Sbjct  606  DMSLRLQCNDYIIRLAAWAGDGFKEGVSLTVYDELARWEKYAYGCNELLFYPIRKWIWKG  665

Query  680  PFTPLFRRFLFSNIRFTSKVTVISYIGTYYAIGAAWILTAVNYFVMGWFNGYLDKYYVDS  739
            PFTPLFRRFLFSNIRFTSK+T+ISYIGTYYAIGAAWILT+VNYF+MGW+NG+LDKYYVDS
Sbjct  666  PFTPLFRRFLFSNIRFTSKITIISYIGTYYAIGAAWILTSVNYFLMGWYNGFLDKYYVDS  725

Query  740  WQVWFSIIIVFNGLGNIALAVMRYRVGERGLLYALFENFMWTLMLAIFLGGLSLHVSQAL  799
            WQVWFSII+VFNGLGN+ALAVMRYRVGER +L ++ ENF WTLMLAIFLGGLSLHVSQAL
Sbjct  726  WQVWFSIILVFNGLGNVALAVMRYRVGERSILGSILENFKWTLMLAIFLGGLSLHVSQAL  785

Query  800  LAHMFEINMTWGATSKEAEFSNFFIEVPKVLKKFKFSMLFSLIFIAGMIILAQAPFVPFD  859
            LAHMFEI+MTWGATSKEAEFSNFFIEVPKVLKKFKFSMLFS+ FI GM+ILA APF+P
Sbjct  786  LAHMFEIDMTWGATSKEAEFSNFFIEVPKVLKKFKFSMLFSIGFIIGMVILATAPFIPHS  845

Query  860  WRIKDFVAILPMATVAASHFLLPLALNPALMTFSW  894
            W I DFVAILPMATVAASH LLPLALNPALMTFSW
Sbjct  846  WHITDFVAILPMATVAASHLLLPLALNPALMTFSW  880
```

FIG. 8F

SEQ ID NO: 18 (*Trichoderma sp.* LOV protein C-terminal residue positions 500-894)
AWADGNIRMGDYILLIDSDTRVPADCLLDAVSEMEQSPDVGIMQFSSGVMQVVHTYFENGITFFTNLIYSAIRYTVS
NGDVAPFVGHNAILRWSAIQQVAYQDEDGYDKFWSESHVSEDFDMSLRLQCNGYIIRLAAWAGEGFKEGVSLTVYDE
LARWEKYAYGCNELLFHPIRTWLWRGPFTPLFRRFLFSNIRFTSKVTVISYIGTYYAIGAAWILTAVNYFVMGWFNG
YLDKYYVDSWQVWFSIIIVFNGLGNIALAVMRYRVGERGLLYALFENFMWTLMLAIFLGGLSLHVSQALLAHMFEIN
MTWGATSKEAEFSNFFIEVPKVLKKFKFSMLFSLIFIAGMIILAQAPFVPFDWRIKDFVAILPMATVAASHFLLPLA
LNPALMTFSW

SEQ ID NO: 17 (*Candida sp.* LOV protein orthologue)
MGITDYFVSKGATEAKQGKNSTDIQQNETLTFPEMLAGPTGASPRAQFTIGETHLSSDIRTLQGHNEMISAGKSDFKDPQFIVVNY
LHDICLGNGWLKLVDPLEPCVVKMNSKKGNEIGYRYLPACDEIAPYSFVDCAARFLRSDVCVRVSFPVIHAILDILSSKGTVSLDA
DHNIQIIETVADLQWVRKSQNCAFIRNEKSLVCWADSVQEVTGFVRNLENKMVDYVWKKGNAVDVKGEDYVPRVTFASVFQSSSES
DVGSEGAVEIIGQNAVSQVSISEKSSDSSTHSDGNLNEKKNLDLEQQSSERPVIYIHATVSAFAITLVLAWAGLQFAQVTKEIRAE
GNYLILLSLLMVLPYFLFTSFFASSVMSTLLYVFGPISQMNKNSYSYSVHKAPRLKAAHGSLPHVTIQCPVYKEKLESVIKPTIKS
LQAAIRTYELQGGSANIFINDDGLQLIDRKEALERIEYYEECGLGYVARPGHGVNGFIRKGRFKKASNMNYCLHISKLVDTRFHER
LELIENPTPKEESGLYLKVLEEVVREEGKCWAGGDILLGDIILIIDSDTRVPEDCFVDSVSEMEQSPEVAIIQHASGVMMVVGNYW
EKMIAWFTNMIYFSISCVSGNGLTMAAFVGHNAFLRWSAIQELAYIDEDDGRTKYWSESHVSEDFEMTLKLASLGYTIRIATYHDG
GFKEGVSLTVYDEITRWSKYAFGCAEIMFSPFKDWWKGKIFARLFFVFLNSHISLPCKFSILGYMGTYYAIATSLIMLVANYFIVG
YYDWGYSRVYIDAMKVFVSVMVVFGCATQVAYIIGRYRIYKHSIYTMVLEFRYSILFSVFLGGLSWHMIVSIGSYFFSLNLQWGAT
AKDIDDSNFFKELPKAIKNYKFMYILCIFLIAGMIVLAFFVPYAFQIRLLTCALPLGWSVASHFLSPIVLNPQLMTFAW

```
Score           Expect       Method         Identities     Positives     Gaps
369 bits(947)   6e-124       Compositional  185/381(49%)   264/381(69%)  7/381(1%)

Query  517  SDTRVPADCLLDAVSEMEQSPDVGIMQFSSGVMQVVHTYFENGITFFTNLIYSAIRYTVS  576
            SDTRVP DC +D+VSEMEQSP+V I+Q +SGVM VV  Y+E  I +FTN+IY +I
Sbjct  563  SDTRVPEDCFVDSVSEMEQSPEVAIIQHASGVMMVVGNYWEKMIAWFTNMIYFSISCVSG  622

Query  577  NG-DVAPFVGHNAILRWSAIQQVAYQDED-GYDKFWSESHVSEDFDMSLRLQCNGYIIRL  634
            NG  +A FVGHNA LRWSAIQ++AY DED G  K+WSESHVSEDF+M+L+L   GY IR+
Sbjct  623  NGLTMAAFVGHNAFLRWSAIQELAYIDEDDGRTKYWSESHVSEDFEMTLKLASLGYTIRI  682

Query  635  AAWAGEGFKEGVSLTVYDELARWEKYAYGCNELLFHPIRTWLWRGP-FTPLFRRFLFSNI  693
            A +   GFKEGVSLTVYDE+ RW KYA+GC E++F P + W W+G  F   LF  FL S+I
Sbjct  683  ATYHDGGFKEGVSLTVYDEITRWSKYAFGCAEIMFSPFKDW-WKGKIFARLFFVFLNSHI  741

Query  694  RFTSKVTVISYIGTYYAIGAAWILTAVNYFVMGWFNGYLDKYYVDSWQVWFSIIIVFNGL  753
            +   +++ Y+GTYYAI + I+    NYF++G+++    + Y+D+ +V+ S+++VF
Sbjct  742  SLPCKFSILGYMGTYYAIATSLIMLVANYFIVGYYDWGYSRVYIDAMKVFVSVMVVFGCA  801

Query  754  GNIALAVMRYRVGERGLLYALFENFMWTLMLAIFLGGLSLHVSQALLAHMFEINMTWGAT  813
            +A + RYR+  +   +Y +  F ++++ ++FLGGLS H+   ++   F +N+ WGAT
Sbjct  802  TQVAYIIGRYRIYKHS-IYTMVLEFRYSILFSVFLGGLSWHMIVSIGSYFFSLNLQWGAT  860

Query  814  SKEAEFSNFFIEVPKVLKKFKFSMLFSLIFIAGMIILAQAPFVPFDWRIKDFVAILPMAT  873
            +K+ + SNFF E+PK +K +KF  +  +  IAGMI+LA    FVP+ ++I+    LP+
Sbjct  861  AKDIDDSNFFKELPKAIKNYKFMYILCIFLIAGMIVLAF--FVPYAFQIRLLTCALPLGW  918

Query  874  VAASHFLLPLALNPALMTFSW  894
               ASHFL P+ LNP LMTF+W
Sbjct  919  SVASHFLSPIVLNPQLMTFAW  939
```

FIG. 8G

MUTANT AND GENETICALLY MODIFIED FILAMENTOUS FUNGAL STRAINS COMPRISING ENHANCED PROTEIN PRODUCTIVITY PHENOTYPES AND METHODS THEREOF

CROSS-REFERENCE TO RELATED APPLICATIONS

The present application is a U.S. National Stage Application under 35 U.S.C. § 371 of International Application No. PCT/US2019/043348, filed Jul. 25, 2019, which claims priority to U.S. Provisional Patent Application Ser. No. 62/711,846, filed Jul. 30, 2018, all of which are hereby incorporated by reference in their entirety.

TECHNICAL FIELD

The present disclosure is generally related to the fields of biology, genetics, molecular biology, filamentous fungi, industrial protein production and the like. More particularly, the present strains and methods of the disclosure relate to genetic modifications in filamentous fungi that give rise to variant strains of filamentous fungi comprising enhanced protein productivity phenotypes. More specifically, as presented, described and exemplified herein, such variant strains of filamentous fungi comprising enhanced protein productivity phenotypes are well-suited for growth in submerged cultures, such as in large-scale production of proteins of interest for commercial applications.

REFERENCE TO A SEQUENCE LISTING

The contents of the electronic submission of the text file Sequence Listing, named "NB41504-WO-PCTSequence-Listing.txt" was created on Jul. 24, 2019 and is 164357 bytes in size, which is hereby incorporated by reference in its entirety.

BACKGROUND

Filamentous fungi (e.g., *Aspergillus* sp., *Penicillium* sp., *Talaromyces* sp., *Fusarium* sp., *Myceliophthora* sp., *Neurospora* sp., *Trichoderma* sp. and the like) are capable of expressing native (endogenous) and heterologous proteins to high levels, making them well-suited for the large-scale production of proteins (e.g., enzymes) and/or metabolites for industrial and/or commercial applications such as pharmaceutical applications, animal health applications, food applications, beverage applications and the like. Filamentous fungi are typically grown in mycelial submerged cultures in bioreactors (fermentors), which bioreactors are adapted to introduce and distribute oxygen and nutrients into the culture medium (i.e., culture broth). For example, the filamentous fungus *Trichoderma reesei* (*T. reesei*; an anamorph of the fungus *Hypocrea jecorina*) is known to be an efficient producer of cellulase enzymes (e.g., see PCT International Publication Nos. WO1998/15619, WO2005/028636, WO2006/074005, WO 1992/06221, WO 1992/06209, WO1992/06183 and WO2002/12465).

As such, filamentous fungi have been utilized for their ability to produce proteins which are valuable in the production of commodities such as cellulosic (derived) ethanol, textile processing, grain processing, detergents, fibers, food additives, feed additives and the like. For example, recombinant gene expression in such fungal host strains is a common method for the production of proteins (i.e., for industrial and commercial purposes) and as such, protein productivity improvements of a fungal host strain are an important economic factor of protein production costs. Thus, as appreciated by one of skill in the art, such compositions and methods for enhancing protein production in filamentous fungal strains are of significant commercial interest.

As described herein, the instant disclosure, which is generally related to genetically modified filamentous fungal strains comprising enhanced/increased protein productivity phenotypes, addresses such ongoing and unmet needs in the art.

SUMMARY

Described herein are strains, cells, methods, constructs and the like relating to filamentous fungi having increased protein productivity phenotypes. Thus, certain embodiments of the disclosure are related to modified Ascomycota cells derived from parental cells, wherein the modified cells comprise a polynucleotide sequence encoding a variant LOV protein comprising at least 50% sequence identity to SEQ ID NO: 2, SEQ ID NO: 4, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 and comprising a lysine (K) residue at an amino acid sequence position corresponding to position 813 of SEQ ID NO: 4, wherein the modified cells comprises an enhanced protein productivity phenotype relative to the parental cells, for example, when fermented/cultivated under the same conditions. In certain embodiments, the parental cells comprise a wild-type polynucleotide sequence encoding a native LOV protein comprising at least 50% sequence identity to SEQ ID NO: 2, SEQ ID NO: 4, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 and comprise a threonine (T) residue at an amino acid sequence position corresponding to position 813 of SEQ ID NO: 2.

In related embodiments, the fungal cells further comprise a heterologous polynucleotide encoding a protein of interest (POI). In other embodiments, the cells further comprising a polynucleotide encoding a NIK1(M743T) protein of SEQ ID NO: 19. In certain other embodiments, the modified cells further comprising at least one genetic modification which deletes, disrupts or reduces the expression/production of a protein selected from the group consisting of MPG1 SFB3, SEB1, CRZ1, TSP2, SSB7 and GAS1.

In other embodiments, the Ascomycota cell is selected from a *Trichoderma* sp., *Aspergillus* sp., *Fusarium* sp., *Penicillium* sp., a *Candida* sp., *Chrysosporium* sp., *Cephalosporium* sp., *Talaromyces* sp., *Neurospora* sp. and *Myceliophthora* sp.

Thus, in certain embodiments, a parental *Aspergillus* sp. cell comprises a polynucleotide sequence encoding a native LOV protein comprising at least 50% sequence identity comprises SEQ ID NO: 11 or SEQ ID NO: 18 and comprises a threonine (T) residue at an amino acid sequence position corresponding to position 813 of SEQ ID NO: 2.

In another embodiment a parental *Penicillium* sp. cell comprises a polynucleotide sequence encoding a native LOV protein comprising at least 50% sequence identity comprises SEQ ID NO: 12 or SEQ ID NO: 18 and comprises a threonine (T) residue at an amino acid sequence position corresponding to position 813 of SEQ ID NO: 2. In other embodiments, a parental *Talaromyces* sp. cell comprises a polynucleotide sequence encoding a native LOV protein comprising at least 50% sequence identity comprises SEQ ID NO: 13 or SEQ ID NO: 18 and comprises a threonine (T)

residue at an amino acid sequence position corresponding to position 813 of SEQ ID NO: 2.

In yet another embodiment, a parental *Fusarium* sp. cell comprises a polynucleotide sequence encoding a native LOV protein comprising at least 50% sequence identity comprises SEQ ID NO: 14 or SEQ ID NO: 18 and comprises a threonine (T) residue at an amino acid sequence position corresponding to position 813 of SEQ ID NO: 2.

In certain other embodiments, a parental *Myceliophthora* sp. cell comprises a polynucleotide sequence encoding a native LOV protein comprising at least 50% sequence identity comprises SEQ ID NO: 15 or SEQ ID NO: 18 and comprises a threonine (T) residue at an amino acid sequence position corresponding to position 813 of SEQ ID NO: 2.

In other embodiments, a parental *Neurospora* sp. cell comprises a polynucleotide sequence encoding a native LOV protein comprising at least 50% sequence identity comprises SEQ ID NO: 16 or SEQ ID NO: 18 and comprises a threonine (T) residue at an amino acid sequence position corresponding to position 813 of SEQ ID NO: 2.

In another embodiment, a parental *Candida* sp. cell comprises a polynucleotide sequence encoding a native LOV protein comprising at least 50% sequence identity comprises SEQ ID NO: 17 or SEQ ID NO: 18 and comprises a threonine (T) residue at an amino acid sequence position corresponding to position 813 of SEQ ID NO: 2.

In certain other embodiments, a parental *Trichoderma* sp. cell comprises a polynucleotide sequence encoding a native LOV protein comprising at least 50% sequence identity comprises SEQ ID NO: 2 or SEQ ID NO: 18 and comprises a threonine (T) residue at an amino acid sequence position corresponding to position 813 of SEQ ID NO: 2.

In other embodiments, a protein of interest is produced by a modified cell of the disclosure and purified therefrom.

In yet other embodiments, the disclosure is related to modified Ascomycota cells derived from parental cells comprising a wild-type polynucleotide sequence which hybridizes under stringent hybridization conditions with a nucleic acid sequence encoding a native LOV protein of SEQ ID NO: 2, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 and comprising a threonine (T) residue at an amino acid sequence position corresponding to position 813 of SEQ ID NO: 2, wherein the modified cells comprise a modified polynucleotide sequence which hybridizes under stringent hybridization conditions with a nucleic acid sequence encoding a LOV protein of SEQ ID NO: 2, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 and comprising a lysine (K) residue at an amino acid sequence corresponding to position 813 of SEQ ID NO: 4. In certain embodiments, the cells further comprise a heterologous polynucleotide encoding a protein of interest. In another embodiment, the cells further comprise a polynucleotide construct encoding a NIK1(M743T) protein of SEQ ID NO: 19. In other embodiments, the cells further comprise at least one genetic modification which deletes, disrupts or reduces the expression/production of a protein selected from the group consisting of MPG1 SFB3, SEB1, CRZ1, TSP2, SSB7 and GAS1.

In certain other embodiments, the Ascomycota cell is selected from a *Trichoderma* sp., *Aspergillus* sp., *Fusarium* sp., *Penicillium* sp., *Candida* sp., *Chrysosporium* sp., *Cephalosporium* sp., *Talaromyces* sp., *Neurospora* sp. and *Myceliophthora* sp.

In certain embodiments, the parental *Aspergillus* sp. cells comprise a polynucleotide sequence encoding a native LOV protein comprising at least 50% sequence identity comprises SEQ ID NO: 11 or SEQ ID NO: 18 and comprise a threonine (T) residue at an amino acid sequence position corresponding to position 813 of SEQ ID NO: 2.

In other embodiments, the parental *Penicillium* sp. cells comprise a polynucleotide sequence encoding a native LOV protein comprising at least 50% sequence identity comprises SEQ ID NO: 12 or SEQ ID NO: 18 and comprise a threonine (T) residue at an amino acid sequence position corresponding to position 813 of SEQ ID NO: 2.

In another embodiment, the parental *Talaromyces* sp. cells comprise a polynucleotide sequence encoding a native LOV protein comprising at least 50% sequence identity comprises SEQ ID NO: 13 or SEQ ID NO: 18 and comprise a threonine (T) residue at an amino acid sequence position corresponding to position 813 of SEQ ID NO: 2.

In certain other embodiments, the parental *Fusarium* sp. cells comprise a polynucleotide sequence encoding a native LOV protein comprising at least 50% sequence identity comprise SEQ ID NO: 14 or SEQ ID NO: 18 and comprises a threonine (T) residue at an amino acid sequence position corresponding to position 813 of SEQ ID NO: 2.

In another embodiment, the parental *Myceliophthora* sp. cells comprise a polynucleotide sequence encoding a native LOV protein comprising at least 50% sequence identity comprises SEQ ID NO: 15 or SEQ ID NO: 18 and comprise a threonine (T) residue at an amino acid sequence position corresponding to position 813 of SEQ ID NO: 2.

In yet other embodiments, the parental *Neurospora* sp. cells comprise a polynucleotide sequence encoding a native LOV protein comprising at least 50% sequence identity comprises SEQ ID NO: 16 or SEQ ID NO: 18 and comprise a threonine (T) residue at an amino acid sequence position corresponding to position 813 of SEQ ID NO: 2.

In certain other embodiments, the parental *Candida* sp. cells comprise a polynucleotide sequence encoding a native LOV protein comprising at least 50% sequence identity comprises SEQ ID NO: 17 or SEQ ID NO: 18 and comprise a threonine (T) residue at an amino acid sequence position corresponding to position 813 of SEQ ID NO: 2.

In other embodiments, the parental *Trichoderma* sp. cells comprise a polynucleotide sequence encoding a native LOV protein comprising at least 50% sequence identity comprises SEQ ID NO: 2 or SEQ ID NO: 18 and comprise a threonine (T) residue at an amino acid sequence position corresponding to position 813 of SEQ ID NO: 2. Other embodiments are related to a protein of interest produced by a modified cell of the disclosure.

Certain other embodiments of the disclosure are related to a vector comprising a polynucleotide encoding a variant LOV protein comprising at least 50% sequence identity to SEQ ID NO: 2, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 and comprising a lysine (K) residue at an amino acid sequence position corresponding to position 813 of SEQ ID NO: 4.

In other embodiments, the disclosure is directed to a polynucleotide encoding a variant LOV protein comprising at least 50% sequence identity to SEQ ID NO: 2, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 and comprising a lysine (K) residue at an amino acid sequence position corresponding to position 813 of SEQ ID NO: 4.

In another embodiment, the disclosure is related to a polynucleotide encoding a variant LOV protein, wherein the polynucleotide encoding the variant protein hybridizes under stringent hybridization conditions with a nucleic acid sequence encoding a LOV protein of SEQ ID NO: 2, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18 and comprising a lysine (K) residue at an amino acid sequence position corresponding to position 813 of SEQ ID NO: 4.

In other embodiments, the disclosure is directed to a mutant *Trichoderma* strain derived from a parental strain, wherein the mutant strain comprises a gene encoding a LOV variant protein comprising at least 50% sequence identity to SEQ ID NO: 4 or SEQ ID NO: 18 and comprising a lysine (K) residue at a sequence position corresponding to position 813 of SEQ ID NO: 4. In certain embodiments, the mutant strain comprises an enhanced protein productivity phenotype relative to the parental strain. In other embodiments, the mutant strain further comprising a polynucleotide construct encoding a NIK1(M743T) protein of SEQ ID NO: 19. In other embodiments, the mutant strain further comprises a genetic modification which deletes, disrupts or reduces the expression/production of a gene encoding at least one protein selected from the group consisting of MPG1 SFB3, SEB1, CRZ1, TSP2, SSB7 and GAS1. Thus, certain related embodiments are directed to a protein of interest produced by the mutant strain.

Other embodiments of the disclosure are related to methods for constructing modified Ascomycota cells comprising enhanced protein productivity phenotypes, the method comprising (i) obtaining a parental cell comprising a wild-type lov gene which hybridizes under stringent hybridizations conditions with a nucleic acid sequence encoding a LOV protein of SEQ ID NO: 2, SEQ ID NO: 11, SEQ ID NO: 12, SEQ ID NO: 13, SEQ ID NO: 14, SEQ ID NO: 15, SEQ ID NO: 16, SEQ ID NO: 17 or SEQ ID NO: 18, (ii) modifying the parental cell of step (i) to produce a modified cell comprising a gene encoding a LOV (variant) protein comprising a lysine (K) residue at a sequence position corresponding to position 813 of SEQ ID NO: 2, and (iii) isolating the modified cell of step (ii), wherein the modified cell comprises an enhanced protein productivity phenotype relative to the parental cell.

In other embodiments, the disclosure is directed to a method for constructing modified Ascomycota cells comprising an enhanced protein productivity phenotype, the method comprising: (i) obtaining a parental Ascomycota cell and introducing into the cell a polynucleotide construct encoding a LOV variant protein comprising a lysine (K) residue at a sequence position corresponding to position 813 of SEQ ID NO: 4 and (ii) isolating the modified cell of step (i), wherein the modified cell comprises an enhanced protein productivity phenotype relative to the parental cell.

Thus, as set forth and described herein, the various embodiments of present disclosure are generally related to variant strains of filamentous fungi comprising enhanced protein productivity phenotypes which variant strains are well-suited for growth in submerged cultures, such as in large-scale production of proteins of interest for commercial applications.

BRIEF DESCRIPTION OF THE BIOLOGICAL SEQUENCES

SEQ ID NO: 1 is a nucleic acid sequence of a wild-type *Trichoderma* sp. lov gene encoding a (native) LOV protein of SEQ ID NO: 2.

SEQ ID NO: 2 is the amino acid sequence of the (native) LOV protein encoded by SEQ ID NO: 1.

SEQ ID NO: 3 is a nucleic acid sequence of a *Trichoderma* sp. mutant allele named "lov(T813K)" encoding a (variant) T813K (substituted) LOV protein of SEQ ID NO: 4.

SEQ ID NO: 4 is the amino acid sequence of the (variant) T813K (substituted) LOV protein encoded by SEQ ID NO: 3.

SEQ ID NO: 5 is the amino acid sequence of a *Trichoderma* sp. MPG1 protein.

SEQ ID NO: 6 is the amino acid sequence of a *Trichoderma* sp. SEB1 protein.

SEQ ID NO: 7 is the amino acid sequence of a *Trichoderma* sp. SFB3 protein.

SEQ ID NO: 8 is the amino acid sequence of a *Trichoderma* sp. CRZ1 protein.

SEQ ID NO: 9 is the amino acid sequence of a *Trichoderma* sp. GAS1 protein.

SEQ ID NO: 10 is the amino acid sequence of a *Trichoderma* sp. TPS2 protein.

SEQ ID NO: 11 is the amino acid sequence of an *Aspergillus* sp. LOV protein orthologue.

SEQ ID NO: 12 is the amino acid sequence of a *Penicillium* sp. LOV protein orthologue.

SEQ ID NO: 13 is the amino acid sequence of a *Talaromyces* sp. LOV protein orthologue.

SEQ ID NO: 14 is the amino acid sequence of a *Fusarium* sp. LOV protein orthologue.

SEQ ID NO: 15 is the amino acid sequence of a *Myceliophthora* sp. LOV protein orthologue.

SEQ ID NO: 16 is the amino acid sequence of a *Neurospora* sp. LOV protein orthologue.

SEQ ID NO: 17 is the amino acid sequence of a *Candida* sp. LOV protein orthologue.

SEQ ID NO: 18 comprises the C-terminal amino acid residue positions 500-894 of the *Trichoderma* sp. (native) LOV protein (SEQ ID NO: 2).

SEQ ID NO: 19 is the amino acid sequence of a variant *Trichoderma* histidine kinase (NIK1) comprising a methionine (M) to threonine (T) substitution at amino acid (residue) position 743 of SEQ ID NO: 19. The gene encoding the variant NIK1 histidine kinase of SEQ ID NO: 19 has been named "nik1(M743T)".

SEQ ID NO: 20 is the nucleic acid sequence of a wild-type *T. reesei* ssb7 gene encoding a native SSB7 protein of SEQ ID NO: 21.

SEQ ID NO: 21 is the amino acid sequence of the native *T. reesei* SSB7 protein encoded by SEQ ID NO: 20.

SEQ ID NO: 22 is the nucleic acid sequence of allele ssb7(fs), comprising a deletion of G (ΔG) in exon 2, resulting in a frame-shift (fs) mutation, and a premature stop codon prior to the last intron of the ssb7 gene.

SEQ ID NO: 23 is the amino acid sequence of the variant SSB7 protein encoded by allele ssb7(fs) of SEQ ID NO: 22.

SEQ ID NO: 23 is the amino acid sequence of a *Trichoderma harzianum* LOV protein orthologue.

BRIEF DESCRIPTION OF THE DRAWINGS

As shown in FIG. 1, the B7ms1-SF12 (daughter) strain (FIG. 1, black line; i.e., comprising the mutant lov(T813K) allele)) has an enhanced protein productivity phenotype relative to the B7ms1 (parental) strain (FIG. 1, grey line; i.e., comprising the wild-type lov gene). For example, as presented in FIG. 1, protein yield on fed sugars increased 44% when the lov(T813K) mutation was present.

FIG. 2 is a graphical representation of a Geneious multiple sequence alignment of six-hundred and ninety-one (691) Pezizomycotina homologs. At the bottom of FIG. 2 are boxes representing the amino acid sequence of the *Trichoderma* LOV protein, wherein amino acid (residues) are presented in black shaded boxes if conserved in greater than 99% of the aligned sequences (or are grey otherwise). LOV residue numbers (SEQ ID NO: 2) are presented above the sequence representation. As presented in FIG. 2, amino acid sequence gaps present in *Trichoderma* LOV or otherwise in >2% of sequences in the multiple sequence alignment, are presented as grey shaded lines. Annotations in the public GenBank sequence for LOV (XP_006967324.1), are shown below the sequence representation as grey boxes. Putative active site residues, as annotated in the GenBank entry for LOV, are shown below the sequence representation as black boxes. The threonine (T) 813 residue substituted for a lysine (K) in strain B7ms1-SF12 is annotated with alight grey box. The mean hydrophobicity and isoelectric point ($_pI$) are also plotted and presented in FIG. 2. The amino acid identity in the alignment is plotted just above the sequence. The lighter grey bars represent residues identical in at least 30% of sequences in the alignment and darker grey bars less than 30%.

FIG. 3 presents total protein yield on fed sugars for these strains under both lower cell density (LCD, dashed lines, circles) and higher cell density (HCD, solid lines, squares) fermentation conditions. The figure legend shows the fermentation condition (LCD vs. HCD) followed by strain name (see TABLE 1 for genotypes) and the lov allele present is shown in parenthesis. Thus, as presented in FIG. 3, the T4mls strain (FIG. 3, black lines; i.e., comprising the mutant lov(T813K) allele)) has an enhanced protein productivity phenotype relative to the T4ms strain (FIG. 3, grey lines; i.e., comprising the wild-type lov gene) under both LCD (dashed lines, circles) and HCD (solid lines, squares) fermentation conditions. For example, as presented in FIG. 3, protein yield on fed sugars increased 42% (LCD) and 32% (HCD) when the lov(T813K) mutation was present.

As shown in FIG. 6, the T4mlp strain (FIG. 6, black line; i.e., comprising the mutant lov(T813K) allele)) has an enhanced protein productivity phenotype relative to the T4mp (parental) strain (FIG. 6, grey line; i.e., comprising the wild-type lov gene). For example, as presented in FIG. 6, protein yield on fed sugars increased 28% when the lov(T813K) mutation was present.

FIG. 7 presents a Clustal W (1.83) multiple sequence alignment of the *Trichoderma* sp. (native) LOV protein (SEQ ID NO: 2), aligned with seven (7) different Ascomycota LOV orthologues. For example, the eight (8) protein sequences used in the Clustal alignment are shown in FIG. 7A-7B (SEQ ID NO: 2 and SEQ ID NOs: 11-17) and the Clustal alignment of the same is shown in FIG. 7C-7F. More particularly, as presented in FIG. 7C-7F, the *Trichoderma* sp. (native) LOV protein (SEQ ID NO: 2; labeled "2", shown in bold CAPITAL residues) is aligned with an *Aspergillus* sp. LOV protein orthologue (SEQ ID NO:11, labeled "11"), a *Penicillium* sp. LOV protein orthologue (SEQ ID NO:12, labeled "12"), a *Talaromyces* sp. LOV protein orthologue (SEQ ID NO:13, labeled "13"), a *Fusarium* sp. LOV protein orthologue (SEQ ID NO:14, labeled "14"), a *Myceliophthora* sp. LOV protein orthologue (SEQ ID NO:15, labeled "15"), a *Neurospora* sp. LOV protein orthologue (SEQ ID NO:16, labeled "16") and a *Candida* sp. LOV protein orthologue (SEQ ID NO:17, labeled "17"). As shown in FIG. 7C-7F (i.e., below the aligned amino residues), an asterisk "*" indicates positions which have a single, fully conserved residue; a colon ":" indicates conservation between groups of strongly similar properties (i.e., scoring>0.5 in the Gonnet PAM 250 matrix) and a period "." indicates conservation between groups of weakly similar properties (i.e., scoring<0.5 in the Gonnet PAM 250 matrix). The highly conserved threonine (T) amino acid is indicated in FIG. 7F, as a bold underlined T residue.

FIG. 8 presents amino acid sequence alignments performed via BLAST protein alignment (NCBI; Blastp suite), using the C-terminal residue positions 500-894 (SEQ ID NO: 18) of the (native) *Trichoderma* sp. LOV protein sequence (SEQ ID NO: 2). For example, as presented in FIG. 8A-8G, SEQ ID NO: 18 comprises a C-terminal amino acid sequence of the *Trichoderma* sp. (native) LOV protein (i.e., comprising 394 amino acid residue positions, which correspond to amino acid residue positions 500-894 of SEQ ID NO: 2), wherein the highly conserved threonine (T) amino acid at residue at position 813 ($T_{813}$) is indicated with a bold, underlined T. Thus, this 394 residue C-terminal amino acid sequence (SEQ ID NO: 18) was aligned with Ascomycota LOV protein orthologues (e.g., SEQ ID NOs: 11-17; FIG. 8A-8G). As shown in FIG. 8A, the *Aspergillus* sp. LOV protein orthologue (SEQ ID NO: 11) comprises about 50% amino acid sequence identity to SEQ ID NO: 18, wherein the highly conserved threonine (T) amino acid at a sequence position corresponding to position 813 of SEQ ID NO: 2 is bold and underlined (FIG. 8A), the *Penicillium* sp. LOV protein orthologue (SEQ ID NO: 12) comprises about 50% amino acid sequence identity to SEQ ID NO: 18, wherein the highly conserved threonine (T) amino acid at a sequence position corresponding to position 813 of SEQ ID NO: 2 is bold and underlined (FIG. 8B), the *Talaromyces* sp. LOV protein orthologue (SEQ ID NO: 13) comprises about 60% amino acid sequence identity to SEQ ID NO: 18, wherein the highly conserved threonine (T) amino acid at a sequence position corresponding to position 813 of SEQ ID NO: 2 is bold and underlined (FIG. 8C), the *Fusarium* sp. LOV protein orthologue (SEQ ID NO: 14) comprises about 88% amino acid sequence identity to SEQ ID NO: 18, wherein the highly conserved threonine (T) amino acid at a sequence position corresponding to position 813 of SEQ ID NO: 2 is bold and underlined (FIG. 8D), the *Myceliophthora* sp. LOV protein orthologue (SEQ ID NO: 15) comprises about 90% amino acid sequence identity to SEQ ID NO: 18, wherein the highly conserved threonine (T) amino acid at a sequence position corresponding to position 813 of SEQ ID NO: 2 is bold and underlined (FIG. 8E), the *Neurospora* sp. LOV protein orthologue (SEQ ID NO: 16) comprises about 90% amino acid sequence identity to SEQ ID NO: 18, wherein the highly conserved threonine (T) amino acid at a sequence position corresponding to position 813 of SEQ ID NO: 2 is bold and underlined (FIG. 8F) and the *Candida* sp. LOV protein orthologue (SEQ ID NO: 17) comprises about 50% amino acid sequence identity to SEQ ID NO: 18, wherein the highly conserved threonine (T) amino acid at a sequence position corresponding to position 813 of SEQ ID NO: 2 is bold and underlined (FIG. 8G).

DETAILED DESCRIPTION

Figure 1:
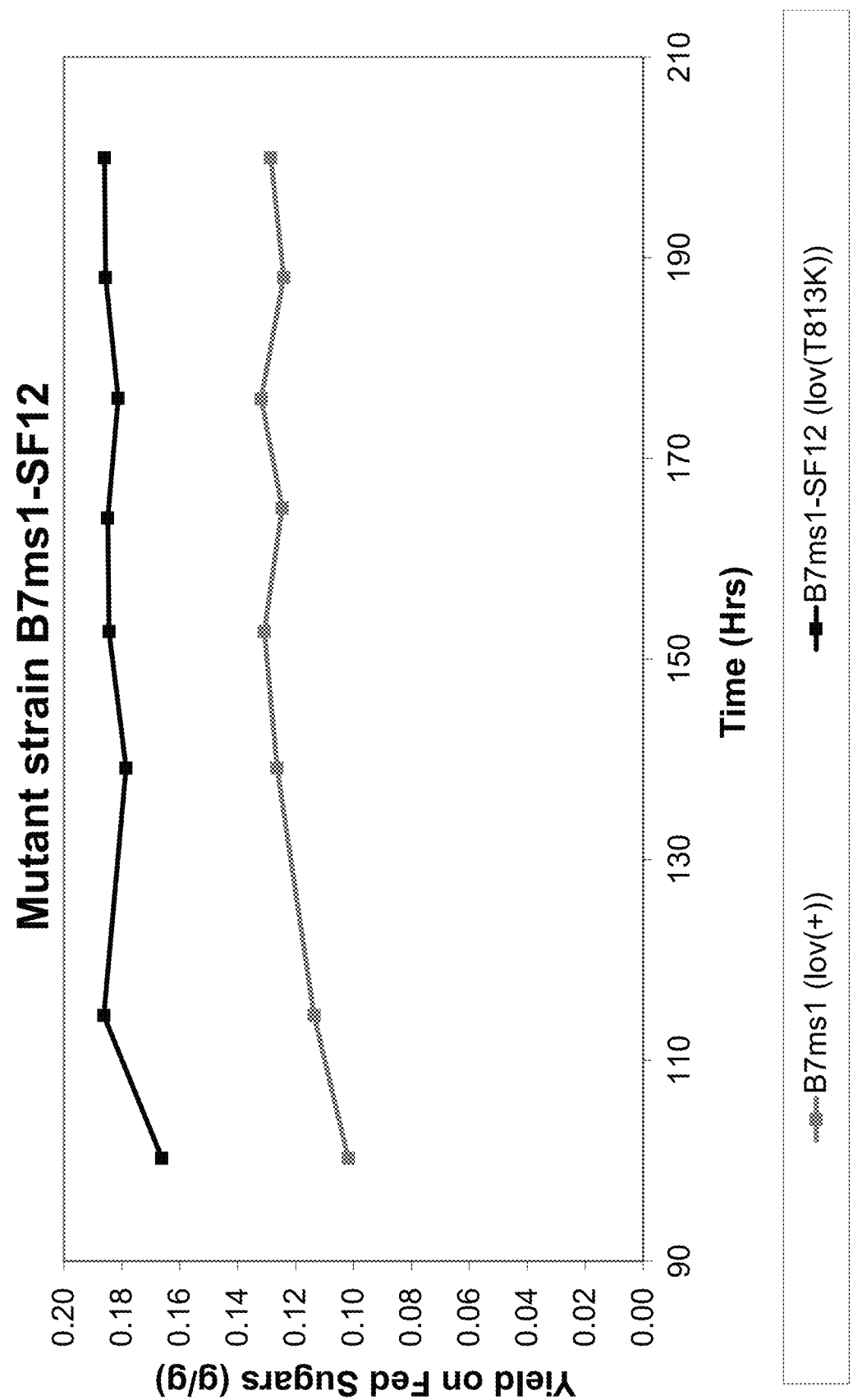
FIG. 1 shows a comparison of total protein yield on fed sugars for the glucoamylase expressing B7ms1 (parental) strain (FIG. 1, grey data points/grey line) and mutant derived (daughter) B7ms1-SF12 strain (FIG. 1, black data points/black line). Thus, these glucoamylase (GA) expressing strains (comprising the viscosity reducing mutations in the mpg1 and seb1 genes) were evaluated for protein productivity in fermentors. The figure legend shows the strain name (see TABLE 1 for genotypes) followed by the lov allele in that strain in parenthesis for each line type.

As set forth and described herein, the present disclosure addresses certain ongoing and unmet needs in the art of filamentous fungi protein production and methods thereof, including but not limited to genetic modifications in filamentous fungi that give rise to variant strains of filamentous fungi comprising enhanced protein productivity phenotypes. More specifically, as presented, described and exemplified herein, such variant strains of filamentous fungi comprising enhanced protein productivity phenotypes are well-suited for growth in submerged cultures, such as in large-scale production of proteins of interest for commercial applications.

I. Definitions

Prior to describing the present strains and methods in detail, the following terms are defined for clarity. Terms not defined should be accorded their ordinary meanings as used in the relevant art. Unless defined otherwise, all technical and scientific terms used herein have the same meaning as commonly understood by one of ordinary skill in the art to which the present compositions and methods apply.

Filamentous fungus cells for manipulation, construction and use as described herein are generally from the phylum Ascomycota, subphylum Pezizomycotina, particularly fungi that have a vegetative hyphae state. Such organisms include filamentous fungus cells used for the production of commercially important industrial and pharmaceutical proteins, including, but not limited to *Trichoderma* sp., *Aspergillus* sp., *Fusarium* sp., *Penicillium* sp., *Chrysosporium* sp., *Cephalosporium* sp., *Talaromyces* sp., *Geosmithia* sp., *Neurospora* sp., *Myceliophthora* sp. and the like. For example, in certain embodiments, filamentous fungus cells and strains thereof include, but are not limited to *Trichoderma reesei* (previously classified as *Trichoderma longibrachiatum* and *Hypocrea jecorina*), *Aspergillus niger*, *Aspergillus fumigatus, Aspergillus itaconicus, Aspergillus oryzae, Aspergillus nidulans, Aspergillus terreus, Aspergillus sojae, Aspergillus japonicus, Neurospora crassa, Penicillium funiculosum, Penicillium chrysogenum, Talaromyces (Geosmithia) emersonii, Fusarium venenatum, Myceliophthora thermophila, Chrysosporium lucknowense* (C1) and the like.

As used herein, terms and phrases such as "filamentous fungus strain(s)", "filamentous fungal strain(s)", "fungus strain(s)", "fungal strains(s)", "filamentous fungus cell(s)", "filamentous fungal cell(s)", "fungus cell(s)", "fungal cell (s)" and the like may be used interchangeably for convenience of description, and are not intend to limit the scope of the disclosure.

In certain embodiments, filamentous fungus cells for manipulation, construction and use as described herein are generally from the phylum Ascomycota, subphylum Pezizomycotina, particularly fungi that have a vegetative hyphae state and comprising a lov gene (or lov gene homologue(s)).

As used herein, phrases such as a "parental cell", a "parental fungal cell", a "parental strain", a "parental fungal strain", a "parental strain of filamentous fungus cells", "reference strain" and the like may be used interchangeably, and refer to "unmodified" parental filamentous fungal cells. For example, a "parental strain of filamentous fungus cells" refers to any cell or strain of filamentous fungi in which the genome of the "parental" cell is modified or modifiable (e.g., via only one genetic modification introduced into the parental cell) to generate a variant (daughter) strain of filamentous fungus cells such that "parental" and "daughter" cells differ by only one genetic modification.

As used herein, phrases such as a "variant cell", a "daughter cell", a "variant strain", a "daughter strain", a "variant or daughter fungal strain", a "variant or daughter strain of filamentous fungus cells" and the like may be used interchangeably, and refer to variant strains of filamentous fungus cells that are derived (i.e., obtained from or obtainable from) from a parental (or reference) strain of filamentous fungus cells, wherein the variant strain comprises only one genetic modification which is not present in the parental strain, such that, by comparison, phenotypic differences between the "parental" and "variant" strains can be attributed to the one genetic modification. In other terms, parental and variant strains are otherwise isogenic except for the single genetic modification "introduced" to the variant strain. Thus, in the present disclosure, parental and variant strains can be described as having certain characteristics, such as genetic modifications, expression phenotypes, morphology phenotypes and the like; however, the skilled person will appreciate that it is technically the cells of the parental or variant strain that have such characteristics, and the "strains" are referred to for convenience.

In certain embodiments, unmodified (parental) cells may be referred to as "control cells" or "reference cells", particularly when being compared (vis-à-vis) with genetically modified (variant/daughter) cells derived therefrom.

As used herein, the terms "wild-type" and "native" are used interchangeably and refer to genes, proteins, protein mixes or strains, as found in nature.

As used herein, certain *Trichoderma reesei* strains/cells of the disclosure have been named/abbreviated as set forth below in Table 1.

TABLE 1

*T. reesei* Strains and Genetic Modifications

| Strain Name | Genetic Modification(s) | Marker Integration Site |
|---|---|---|
| B7ms1 | Δmpg1; Δseb1; GA construct; lov(+) | seb1 |
| B7ms1-SF12 | Δmpg1; Δseb1; GA construct; lov(T813K) | seb1 |
| T4 | nik1(M743T); lov(+) | pyr2 |
| T4_pyr2 | nik1(M743T); lov(+); pyr2 | None |
| T4m | nik1(M743T); Δmpg1; lov(+) | mpg1 |
| T4m_pyr2 | nik1(M743T); Δmpg1; lov(+); pyr2 | None |
| T4ml+ | nik1(M743T); Δmpg1; lov(dis) | lov |
| T4ml | nik1(M743T); Δmpg1; lov(T813K); pyr2 | None |
| T4mls | nik1(M743T); Δmpg1; Δseb1; lov(T813K) | seb1 |
| T4ms | nik1(M743T); Δmpg1; Δseb1; lov(+) | seb1 |
| T4s | nik1(M743T); Δseb1; lov(+) | seb1 |
| T4s_pyr2 | nik1(M743T); Δseb1; lov(+); pyr2 | None |
| T4sl+ | nik1(M743T); Δseb1; lov(dis) | lov |
| T4sl | nik1(M743T); Δseb1; lov(T813K); pyr2 | None |
| T4l+ | nik1(M743T); lov(dis) | lov |
| 41G | nik1(M743T); lov(+) | pyr4 |
| 41G_pyr4 | nik1(M743T); lov(+); pyr4 | None |
| 41G1+ | nik1(M743T); lov(dis) | lov |
| T4mc | nik1(M743T); Δmpg1; lov(+) | site C |
| T4mlc | nik1(M743T); Δmpg1; lov(T813K) | site C |
| T4md | nik1(M743T); Δmpg1; lov(+) | site B |
| T4mld | nik1(M743T); Δmpg1; lov(T813K) | site B |
| T4mp | nik1(M743T); Δmpg1; lov(+) | site A |
| T4mlp | nik1(M743T); Δmpg1; lov(T813K) | site A |
| T4sp | nik1(M743T); Δseb1; lov(+) | site A |
| T4slp | nik1(M743T); Δseb1; lov(T813K) | site A |

As used herein, a reduced viscosity *Trichoderma* strain "B7ms1" is a glucoamylase expressing strain referred to as "Morph TrGA 771B7Δmpg1Δseb1" in International PCT Publication No. WO2012/145584 (incorporated herein by reference in its entirety).

As used herein, genomic coordinates (e.g., 425393 on Scaffold 16) and Protein Identification numbers (PID, e.g., PID 50212) reference Version 2 of the *Trichoderma reesei* QM6a genome sequence assembly generated by the Department of Energy Joint Genome Institute (QGI). (The Genome Portal of the Department of Energy Joint Genome Institute, Grigoriev et al., *Nucleic Acids Res* 2012 January; 40 (Database issue):D26-32. doi: 10.1093/nar/gkr947). The JGI assembled Scaffold sequences have also been deposited in GenBank (The National Center for Biotechnology) under the nucleotide accession numbers GL985056.1 through GL985132.1.

As used herein, a mutant (variant) *Trichoderma* strain named "B7ms1-SF12" (derived from the B7ms1 parental strain) comprises an increased protein productivity phenotype (i.e., relative to B7ms1 (parental) strain). More particularly, the identified mutation in *Trichoderma* B7 ms1-SF12 strain alters the coding sequence of a protein named LOV (i.e., predicted protein PID 50212; SEQ ID NO: 2), wherein a highly-conserved threonine (T) amino acid at residue position 813 (T813) of the (native) LOV protein (SEQ ID NO: 2) was substituted with a lysine (T→K813) in the (mutant) B7ms1-SF12 strain (i.e., a T813K substitution, e.g., compare SEQ ID NO: 2 position 813 vis-à-vis SEQ ID NO: 4 position 813). For example, as described in the Examples section below, the lov mutant allele in strain B7ms1-SF12 comprises a single nucleotide change of G (guanine) to T (thymine) at 425393 on Scaffold 16, thereby resulting in the "T813K" substitution in the encoded LOV (variant) protein (SEQ ID NO: 4), comprising a lysine (K) at amino acid position 813 of SEQ ID NO: 4 (in contrast to the native LOV protein of SEQ ID NO: 2, comprising a threonine (T) at amino acid position 813; SEQ ID NO: 2).

As used herein, a *Trichoderma* strain named "T4" was derived from *Trichoderma* strain RL-P37 by incorporation of the nik1(M743T) mutation and chemical mutagenesis, as described in International PCT Publication No. WO2016/130523 (incorporated herein by reference in its entirety).

As used herein, a gene allele named "nik1(M743T)", comprises a mutant histidine kinase gene (nik1) encoding a variant histidine kinase (NIK1; SEQ ID NO: 19) comprising a methionine (M) to threonine (T) substitution at amino acid (residue) position 743 of SEQ ID NO: 19.

As used herein, a *Trichoderma* strain named "T4_pyr2" was derived from *Trichoderma* strain T4 by mutation and loss of function of the pyr2 gene so that it may be used as a transformation selection marker.

As used herein, a *Trichoderma* strain named "T4m" was derived from strain T4, wherein strain T4m comprises a mutation of the mpg1 gene (Δmpg1) and a nik1(M743T) gene. Strain T4m therefore comprises the wild-type lov allele (i.e., allele lov(+)) encoding the native lov protein (SEQ ID NO: 2).

As used herein, a *Trichoderma* strain named "T4m_pyr2" was derived from strain T4m, wherein strain T4m_pyr2 comprises a mutation of the mpg1 gene (Δmpg1), a nik1 (M743T) gene and no functional pyr2 gene.

As used herein, a *Trichoderma* strain named "T4ml+" was derived from strain T4m_pyr2, wherein strain T4ml+ comprises a mutation of the mpg1 gene (Δmpg1) and allele lov(dis).

As used herein, a *Trichoderma* strain named "T4ml" was derived from strain T4ml+, wherein strain T4ml comprises nik1(M743T), a mutation of the mpg1 gene (Δmpg1), allele lov(T813K), and no functional pyr2 gene.

As used herein, a *Trichoderma* strain named "T4mls" was derived from strain T4ml, wherein strain T4mls comprises nik1(M743T), a double mutation of the mpg1 and seb1 genes (Δmpg1; Δseb1) and allele lov(T813K).

As used herein, a *Trichoderma* strain named "T4ms" was derived from strain T4m, wherein strain T4ms comprises nik1(M743T) and a double mutation of the mpg1 and seb1 genes (Δmpg1; Δseb1).

As used herein, a *Trichoderma* strain named "T4s" was derived from strain T4, wherein strain T4s comprises nik1 (M743T) and a mutation of the seb1 gene (Δseb1).

As used herein, a *Trichoderma* strain named "T4s_pyr2" was derived from strain T4s, wherein strain T4s_pyr2 comprises nik1(M743T), a mutation of the seb1 gene (Δseb1) and no functional pyr2 gene.

As used herein, a *Trichoderma* strain named "T4sl+" was derived from strain T4s_pyr2, wherein strain T4sl+ comprises nik1(M743T), a mutation of the seb1 gene (Δseb1) and allele lov(dis).

As used herein, a *Trichoderma* strain named "T4sl" was derived from strain T4sl+, wherein strain T4sl comprises nik1(M743T), a mutation of the seb1 gene (Δseb1), allele lov(T813K) and no functional pyr2 gene.

As used herein, a *Trichoderma* strain named "T4l+" was derived from strain T4_pyr2, wherein strain T4l+ comprises nik1(M743T) and allele lov(dis).

As used herein, a *Trichoderma* strain named "41G" was a mutagenized derived from strain T4, wherein strain 41G comprises nik1(M743T) and the (wild-type) lov(+) allele.

As used herein, a *Trichoderma* strain named "41G_pyr4" was derived from strain 41G, wherein strain 41G_pyr4 comprises nik1(M743T), the (wild-type) lov(+) allele and deletion of the pyr4 gene.

As used herein, a *Trichoderma* strain named "41Gl+" was derived from strain 41G_pyr4, wherein strain 41Gl+ comprises nik1(M743T) and allele lov(dis).

As used herein, a *Trichoderma* strain named "T4mc" was derived from strain T4m_pyr2, wherein strain T4mc comprises nik1(M743T), Δmpg1, pyr2+ insertion at site C and a wild-type lov(+) allele.

As used herein, a *Trichoderma* strain named "T4mlc" was derived from strain T4ml, wherein strain T4mlc comprises nik1(M743T), Δmpg1, pyr2+ insertion at site C and allele lov(T813K).

As used herein, a *Trichoderma* strain named "T4md" was derived from strain T4m_pyr2, wherein strain T4md comprises nik1(M743T), Δmpg1, pyr2+ insertion at site B and a wild-type lov(+) allele.

As used herein, a *Trichoderma* strain named "T4mld" was derived from strain T4ml, wherein strain T4mld comprises nik1(M743T), Δmpg1, pyr2+ insertion at site B and allele lov(T813K).

As used herein, a *Trichoderma* strain named "T4mp" was derived from strain T4m_pyr2, wherein strain T4mp comprises nik1(M743T), Δmpg1, pyr2+ insertion at site A and a wild-type lov(+) allele.

As used herein, a *Trichoderma* strain named "T4mlp" was derived from strain T4ml, wherein strain T4mlp comprises nik1(M743T), Δmpg1, pyr2+ insertion at site A and allele lov(T813K).

As used herein, a *Trichoderma* strain named "T4sp" was derived from strain T4s_pyr2, wherein strain T4sp comprises nik1(M743T), Δseb1, pyr2+ insertion at site A and a wild-type lov(+) allele.

As used herein, a *Trichoderma* strain named "T4slp" was derived from strain T4sl, wherein strain T4slp comprises nik1(M743T), Δseb1, pyr2+ insertion at site A and allele lov(T813K).

As used herein, a "glucoamylase (GA) construct" or "GA construct" encodes a glucoamylase described in PCT Publication No. WO2012/145584 (specifically incorporated herein by reference in its entirety).

As used herein, "allele lov(+)" comprises a wild-type lov DNA sequence encoding a native LOV protein (e.g., SEQ ID NO: 2).

As used herein, "allele lov(T813K)" comprises a mutated (lov) DNA sequence (identified in strain B7ms1-SF12, described above) encoding a variant LOV protein comprising the "T813K" substitution (SEQ ID NO: 4, described above).

As used herein, "allele lov(dis)" comprises a disruption of the lov gene in which a selectable marker, either pyr2 or pyr4, was integrated into the lov coding sequence, as further described in Example 3 below.

As used herein, a "whole cellulase strain" refers to a *Trichoderma* strain where the natural secretome has not been altered by genetic engineering of the major cellulase genes.

As used herein, an "endogenous (or native) filamentous fungal gene" encoding a protein of interest includes, but is not limited to, endogenous (filamentous fungal) genes encoding glycoside hydrolase (GH) family enzymes (e.g., such as EC Nos. 3.2.1.1-3.2.1.206), endogenous genes encoding proteases, esterases, lipases and the like, as known and understood by one skilled in the art.

Thus, as generally described herein, a substitution of a threonine (T) amino acid for a lysine (K) amino acid (T4K substitution) at an amino acid (residue) position equivalent to position 813 of the (variant) LOV protein of SEQ ID NO: 4, has been identified herein as being responsible for the observed (increased) protein productivity phenotypes. For example, filamentous fungal cells disclosed herein, comprising an introduced allele encoding the (mutant) B7ms1-SF12 strain $T_{813} \rightarrow_{813}K$ substitution (e.g., allele lov(T813K)) demonstrate enhanced protein productivity phenotypes relative to isogenic cells lacking this mutation (i.e., comprising a wild-type lov gene, allele lov(+), encoding a native LOV protein) when fermented/cultivated under the same conditions. More particularly as presented in the Examples section below, filamentous fungal cells of the disclosure (comprising such enhanced protein productivity phenotypes) are particularly well-suited for growth in (aerobic) submerged cultures (e.g., such as in large-scale production of proteins of interest for commercial applications).

As used herein, the "position" of an amino acid residue in a "given amino acid sequence" is numbered herein using the amino acid residue numbering (positions) of the native *Trichoderma* sp. LOV protein of SEQ ID NO: 2. For example, phrases such as "comprises a threonine (T) residue at a sequence position corresponding to position 813 of SEQ ID NO: 2" and "comprises a lysine (K) residue at a sequence position corresponding to position 813 of SEQ ID NO: 2", the native (*Trichoderma* sp.) LOV protein's amino acid sequence (SEQ ID NO: 2) serves as a reference (parent) protein sequence.

For example, as shown in FIG. 7C-7F, a given amino acid sequence described herein can be aligned with the native *Trichoderma* sp. LOV protein amino acid sequence (SEQ ID NO: 2), using alignment algorithms described herein (and/or alignment algorithms known in the art,) and an amino acid residue in the given amino acid sequence that aligns (preferably, optimally aligns) with an amino acid residue in the native sequence can be conveniently numbered by reference to the corresponding amino acid residue in the LOV sequence. Thus, FIG. 7 presents a multiple sequence alignment of the native *Trichoderma* sp. LOV protein (SEQ ID NO: 2) labeled sequence "2", aligned with LOV protein orthologues from various (Ascomycota) filamentous fungi, such as *Aspergillus* sp. (SEQ ID NO: 12) labeled sequence "12", *Penicillium* sp. (SEQ ID NO: 13) labeled sequence "13", *Talaromyces* sp. (SEQ ID NO: 14) labeled sequence "14", *Fusarium* sp. (SEQ ID NO: 15) labeled sequence "15", *Myceliophthora* sp. (SEQ ID NO: 16) labeled sequence "16", *Neurospora* sp. (SEQ ID NO: 17) labeled sequence "17" and *Candida* sp. (SEQ ID NO: 18) labeled sequence "18".

Likewise, to establish sequence homology or sequence identity to the primary (10) sequence of the *Trichoderma* sp. LOV protein (SEQ ID NO: 2), one skilled in the art may readily compare the primary sequence of SEQ ID NO: 2 with one or more candidate LOV protein (orthologue) sequences using sequence alignment algorithms, software and methods thereof know to one skilled in the art. Thus, after aligning the conserved residues, allowing for necessary insertions and deletions in order to maintain alignment (i.e., avoiding the elimination of conserved residues through arbitrary deletion and insertion), the residues equivalent to particular amino acids in the primary sequence of Ascomycota LOV protein are defined. Alignment of conserved residues preferably should conserve 100% of such residues.

However, alignment of greater than 98%, 95%, 90%, 85%, 80%, 75% 70%, 50% or at least 45% of conserved residues is also adequate to define equivalent residues.

Thus, as used herein, a substitution of a threonine (T) amino acid for a lysine (K) amino acid ($T_{813} \rightarrow {}_{813}K$ substitution) at an amino acid (residue) position corresponding (or equivalent) to position 813 of SEQ ID NO: 2, includes any $T_{813} \rightarrow {}_{813}K$ substitution at an amino acid (residue) position corresponding to position 813 of SEQ ID NO: 2 in any Ascomycota filamentous fungal cell.

As used herein, the term "gene" is synonymous with the term "allele" in referring to a nucleic acid that encodes and directs the expression of a protein or RNA. Vegetative forms of filamentous fungi are generally haploid, therefore a single copy of a specified gene (i.e., a single allele) is sufficient to confer a specified phenotype.

As used herein, the terms "polypeptide" and "protein" (and/or their respective plural forms) are used interchangeably to refer to polymers of any length comprising amino acid residues linked by peptide bonds. The conventional one-letter or three-letter codes for amino acid residues are used herein. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

As used herein, the term "derivative polypeptide/protein" refers to a protein which is derived or derivable from a protein by addition of one or more amino acids to either or both the N- and C-terminal end(s), substitution of one or more amino acids at one or a number of different sites in the amino acid sequence, deletion of one or more amino acids at either or both ends of the protein or at one or more sites in the amino acid sequence, and/or insertion of one or more amino acids at one or more sites in the amino acid sequence. The preparation of a protein derivative can be achieved by modifying a DNA sequence which encodes for the native protein, transformation of that DNA sequence into a suitable host, and expression of the modified DNA sequence to form the derivative protein.

Related (and derivative) proteins include "variant proteins". Variant proteins differ from a reference/parental protein (e.g., a wild-type protein) by substitutions, deletions, and/or insertions at a small number of amino acid residues. The number of differing amino acid residues between the variant and parental protein can be one or more, for example, 1, 2, 3, 4, 5, 6, 7, 8, 9, 10, 15, 20, 30, 40, 50, or more amino acid residues. Variant proteins can share at least about 50%, at least about 60%, at least about 75%, at least about 80%, at least about 85%, at least about 90%, at least about 91%, at least about 92%, at least about 93%, at least about 94%, at least about 95%, at least about 96%, at least about 97%, at least about 98%, or even at least about 99%, or more, amino acid sequence identity with a reference protein. A variant protein can also differ from a reference protein in selected motifs, domains, epitopes, conserved regions, and the like.

As used herein, the term "analogous sequence" refers to a sequence within a protein that provides similar function, tertiary structure, and/or conserved residues as the protein of interest (i.e., typically the original protein of interest). For example, in epitope regions that contain an α-helix or a β-sheet structure, the replacement amino acids in the analogous sequence preferably maintain the same specific structure. The term also refers to nucleotide sequences, as well as amino acid sequences. In some embodiments, analogous sequences are developed such that the replacement of amino acids result in a variant enzyme showing a similar or improved function. In some embodiments, the tertiary structure and/or conserved residues of the amino acids in the protein of interest are located at or near the segment or fragment of interest. Thus, where the segment or fragment of interest contains, for example, an α-helix or a β-sheet structure, the replacement amino acids preferably maintain that specific structure.

As used herein, the term "homologous protein" refers to a protein that has similar activity and/or structure to a reference protein. It is not intended that homologues necessarily be evolutionarily related. Thus, it is intended that the term encompass the same, similar, or corresponding protein(s) (i.e., in terms of structure and function) obtained from different organisms. In some embodiments, it is desirable to identify a homologue that has a quaternary, tertiary and/or primary structure similar to the reference protein.

The degree of homology between sequences can be determined using any suitable method known in the art (see, e.g., Smith and Waterman, 1981; Needleman and Wunsch, 1970; Pearson and Lipman, 1988; programs such as GAP, BESTFIT, FASTA, and TFASTA in the Wisconsin Genetics Software Package (Genetics Computer Group, Madison, WI); and Devereux et al., 1984).

For example, PILEUP is a useful program to determine sequence homology levels. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (1987). The method is similar to that described by Higgins and Sharp (1989). Useful PILEUP parameters including a default gap weight of 3.00, a default gap length weight of 0.10, and weighted end gaps. Another example of a useful algorithm is the BLAST algorithm, described by Altschul et al., 1990 and Karlin et al., 1993. One particularly useful BLAST program is the WU-BLAST-2 program (see, e.g., Altschul et al., 1996). Parameters "W," "T," and "X" determine the sensitivity and speed of the alignment. The BLAST program uses as defaults a word-length (W) of 11, the BLOSUM62 scoring matrix (see, e.g., Henikoff and Henikoff, 1989) alignments (B) of 50, expectation (E) of 10, M'5, N'-4, and a comparison of both strands.

As used herein, the phrases "substantially similar" and "substantially identical", in the context of at least two nucleic acids or polypeptides, typically means that a polynucleotide or polypeptide comprises a sequence that has at least about 70% identity, at least about 75% identity, at least about 80% identity, at least about 85% identity, at least about 90% identity, at least about 91% identity, at least about 92% identity, at least about 93% identity, at least about 94% identity, at least about 95% identity, at least about 96% identity, at least about 97% identity, at least about 98% identity, or even at least about 99% identity, or more, compared to the reference (i.e., wild-type) sequence. Sequence identity can be determined using known programs such as BLAST, ALIGN, and CLUSTAL using standard parameters. (See, e.g., Altschul, et al., 1990; Henikoff et al., 1989; Karlin et al., 1993; and Higgins et al., 1988). Software for performing BLAST analyses is publicly available through the National Center for Biotechnology Information. Also, databases can be searched using FASTA (Pearson et al., 1988). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

As used herein, "nucleic acid" refers to a nucleotide or polynucleotide sequence, and fragments or portions thereof, as well as to DNA, cDNA, and RNA of genomic or synthetic origin, which may be double-stranded or single-stranded, whether representing the sense or antisense strand.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to transcription, post-transcriptional modification, translation, post-translational modification, secretion and the like.

As used herein, the combined term "expresses/produces", as used in phrases such as a "variant strain of filamentous fungus cells expresses/produces an 'increased' amount of a protein of interest (POI)" (i.e., relative to the parental cell), the term "expresses/produces" is meant to include any steps involved in the expression and production of a protein in such variant filamentous fungus strains of the disclosure.

In certain embodiments, a gene, polynucleotide or nucleic acid sequence encoding a LOV protein comprising "sequence homology" refers to DNA or RNA (nucleic acid) sequences that have de minimus sequence variations from the corresponding nucleic acid sequences (to which comparison is made) and retain substantially the same biological functions as the corresponding nucleic acid sequences (to which comparison is made). For example, in certain embodiments, a nucleic acid sequence comprising substantial sequence homology to a gene, polynucleotide, or nucleic acid encoding a LOV protein is assessed by identifying the encoded gene product (LOV protein), as described herein.

In certain other embodiments, a gene, polynucleotide, or nucleic acid sequence comprising sequence homology to a gene, polynucleotide, or nucleic acid encoding a LOV protein is determined/identified using nucleic acid hybridization methods. For example, in certain embodiments, a DNA/RNA sequence comprising substantial sequence homology to a gene encoding a LOV protein (e.g., SEQ ID NO: 2) is identified by the ability of such DNA/RNA sequence to hybridize with a specified nucleic acid sequence of the disclosure, under stringent conditions.

As used herein, "hybridizes under stringent conditions" is intended to describe conditions for hybridization and washing under which nucleotide sequences that are significantly identical or homologous to each other remain hybridized to each other. Such stringent conditions are well known to those skilled in the art (see, e.g., Ausubel et al., 1995; Sambrook et al., 1989). For example, in certain embodiments, a non-limiting example of stringent hybridization conditions includes hybridization in 4× sodium chlorine/sodium citrate (SSC), at about 65-70° C. (or hybridization in 4×SSC plus 50% formamide at about 42-50° C.), followed by one or more washes in 1×SSC, at about 65-70° C. Likewise, a non-limiting example of highly stringent hybridization conditions includes hybridization in 1×SSC, at about 65-70° C. (or hybridization in 4×SSC plus 50% formamide at about 42-50° C.), followed by one or more washes in 0.3×SSC, at about 65-70° C. Thud, highly stringent hybridization conditions include hybridization in 4×SSC, at about 50-60° C. (or alternatively hybridization in 6×SSC plus 50% formamide at about 40-45° C.), followed by one or more washes in 2×SSC, at about 50-60° C. Ranges intermediate to the above-recited values, e.g., at 65-70° C. or at 42-50° C. are also intended to be encompassed by the present disclosure. In certain embodiments, SSPE (1×SSPE is 0.15 M NaCl, 10 mM NaH2PO4, and 1.25 mM EDTA, pH 7.4) can be substituted for SSC (1×SSPE is 0.15 M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6(log 10[Na+])+0.41(% G+C)−(600/N), where N is the number of bases in the hybrid, and [Na+] is the concentration of sodium ions in the hybridization buffer ([Na+] for 1×SSC=0.165 M). It will also be recognized by the skilled practitioner that additional reagents may be added to the hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS) chelating agents (e.g., EDTA), Ficoll, PVP and the like. When using nylon membranes, in particular, an additional, non-limiting example of stringent hybridization conditions is hybridization in 0.25-0.5M NaH2PO4, 7% SDS at about 65° C., followed by one or more washes at 0.02M NaH2PO4, 1% SDS at 65° C. or alternatively 0.2×SSC, 1% SDS (see, e.g., Church and Gilbert, 1984).

Thus, as generally set forth above, certain embodiments of the disclosure are related to variant strains of filamentous fungus cells comprise a genetic modification of a gene encoding a LOV protein. As used herein, the terms "modification" and "genetic modification" are used interchangeably and include, but are not limited to: (a) the introduction, substitution, or removal of one or more nucleotides in a gene, or the introduction, substitution, or removal of one or more nucleotides in a regulatory element required for the transcription or translation of the gene, (b) gene disruption, (c) gene conversion, (d) gene deletion, (e) the down-regulation of a gene (e.g., antisense RNA, siRNA, miRNA, and the like), (f) specific mutagenesis (including, but not limited to, CRISPR/Cas9 based mutagenesis) and/or (g) random mutagenesis of any one or more the genes disclosed herein.

As used herein, a variant strain of filamentous fungus comprising a genetic modification includes, but is not limited to a genetic modification of a gene encoding a LOV protein disclosed herein. Thus, as described in further detail below, various molecular biological methods are well known and available to one skilled in the art for generating/constructing such variant strains of filamentous fungus cells.

As used herein, "the introduction, substitution, or removal of one or more nucleotides in a gene encoding a protein", such genetic modifications include the gene's coding sequence (i.e., exons) and non-coding intervening (introns) sequences.

As used herein, "disruption of a gene", "gene disruption", "inactivation of a gene" and "gene inactivation" are used interchangeably and refer broadly to any genetic modification that substantially disrupts/inactivates a target gene. Exemplary methods of gene disruptions include, but are not limited to, the complete or partial deletion of any portion of a gene, including a polypeptide coding sequence (CDS), a promoter, an enhancer, or another regulatory element, or mutagenesis of the same, where mutagenesis encompasses substitutions, insertions, deletions, inversions, and any combinations and variations thereof which disrupt/inactivate the target gene(s) and substantially reduce or prevent the expression/production of the functional gene product. In certain embodiments of the disclosure, such gene disruptions prevent a host cell from expressing/producing the encoded lov gene product.

In certain embodiments, a gene, polynucleotide or nucleic acid sequence encoding a LOV protein is genetically modified using an established gene editing technique, such as CRISPR/Cas9 gene editing, zinc-finger nuclease (ZFN) gene editing, transcription activator-like effector nuclease editing (TALEN), homing (mega) nuclease editing, and the like.

In other embodiments, a variant strain of filamentous fungus is constructed (i.e., genetically modified) by the process of gene conversion (e.g., see Iglesias and Trautner, 1983).

In other embodiments, a protein of interest (e.g., an endogenous POI or a heterologous POI) expressed/produced by the Ascomycota cells of the disclosure is detected, measured, assayed and the like, by protein quantification methods, gene transcription methods, mRNA translation methods and the like, including, but not limited to protein migration/mobility (SDS-PAGE), mass spectrometry, HPLC, size exclusion, ultracentrifugation sedimentation velocity analysis, transcriptomics, proteomics, fluorescent tags, epitope tags, fluorescent protein (GFP, RFP, etc.) chimeras/hybrids and the like.

As used herein, functionally and/or structurally similar proteins are considered to be "related proteins". Such related proteins can be derived from organisms of different genera and/or species, or even different classes of organisms (e.g., bacteria and fungi). Related proteins also encompass homologues and/or orthologues determined by primary sequence analysis, determined by secondary or tertiary structure analysis, or determined by immunological cross-reactivity.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation. A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As defined herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding site and stem-loop structure.

As defined herein, the term "introducing", as used in phrases such as "introducing into a fungal cell" at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection and the like.

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in the cell that is to be transformed).

As used herein, "transformation" refers to introducing an exogenous DNA into a host cell so that the DNA is maintained as a chromosomal integrant or a self-replicating extra-chromosomal vector. As used herein, "transforming DNA", "transforming sequence", and "DNA construct" refer to DNA that is used to introduce sequences into a host cell. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein "an incoming sequence" refers to a DNA sequence that is introduced into the fungal cell chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, an incoming sequence is a non-functional sequence inserted into a gene to disrupt function of the gene. In another embodiment, the incoming sequence includes a selective marker. In a further embodiment the incoming sequence includes two homology boxes.

As used herein, "homology box" refers to a nucleic acid sequence, which is homologous to a sequence in the fungal cell chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the fungal cell chromosome a DNA construct is integrated and directs what part of the fungal cell chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, the term "selectable marker-encoding nucleotide sequence" refers to a nucleotide sequence which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell which allows for ease of selection of those hosts containing the vector. Examples of such selectable markers include, but are not limited to, antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

As defined herein, a host cell "genome", a fungal cell "genome", or a filamentous fungus cell "genome" includes chromosomal and extrachromosomal genes.

As used herein, the terms "plasmid", "vector" and "cassette" refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term "vector" refers to any nucleic acid that can be replicated (propagated) in cells and can carry new genes or DNA segments (e.g., an "incoming sequence") into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes), BACs (bacterial artificial chromosomes), PLACs (plant artificial chromosomes), and the like, that are "episomes" (i.e., replicate autonomously) or can integrate into the chromosome of a host cell.

A used herein, a "transformation cassette" refers to a specific vector comprising a gene (or ORF thereof), and having elements in addition to the gene that facilitate transformation of a particular host cell.

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments, DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing genetic modifications into the chromosome of a host cell through homologous recombination. In some embodiments, a targeting vector comprises other non-homologous sequences, e.g., added to the ends (i.e., stuffer sequences or flanking sequences). The ends can be closed such that the targeting vector forms a closed circle, such as, for example, insertion into a vector.

As used herein, a variant cell (or strain) comprising an "enhanced protein productivity phenotype" includes, but is not limited to, a variant cell (or strain) comprising an enhanced/increased volumetric productivity, a variant cell (or strain) comprising an enhanced/increased carbon conversion efficiency, a variant cell (or strain) comprising an enhanced/increased protein yield, a variant cell (or strain) comprising an enhanced/increased specific protein productivity and the like. For example, in certain embodiments, a variant cell or strain comprising an enhanced protein productivity phenotype expresses/produces at least 0.10% or more total protein (g) per g of fed sugars (relative to parental strain), wherein fed sugars can be expressed in terms of mass of sugar added to the fermentor during production phase (i.e., following feed-start).

As defined herein, the phrases "enhanced protein productivity phenotype" and "increased protein productivity phenotype", may be used interchangeably.

As used herein, when describing an "enhanced/increased protein productivity phenotype" in an unmodified (parental) cell vis-à-vis the modified (variant/daughter), it will be understood that the "parental" and "variant" cells are grown/cultivated/fermented under the same conditions (e.g., the same conditions such as media, temperature, pH and the like). Similarly, when describing the "expression/production" of a protein of interest (POI) in an unmodified (parental) cell vis-à-vis the "expression/production" of the same POI in a modified (variant/daughter) cell, it will be understood that the "parental" and "variant" cells are grown/cultivated/fermented under essentially the same conditions (e.g., the same conditions such as media, temperature, pH and the like).

As used herein, "aerobic fermentation" refers to growth in the presence of oxygen.

As used herein, the terms "broth", "cell broth", "fermentation broth" and/or "culture broth" are used interchangeably, and refer collectively to (i) the fermentation (culture) medium and (ii) the cells, in a liquid (submerged) culture.

As used herein, the term "cell mass" refers to the cell component (including intact and lysed cells) present in a liquid (submerged) culture. Cell mass can be expressed in dry cell weight (DCW) or wet cell weight (WCW).

As used herein, a "reduced viscosity" strain of filamentous fungus cells refers to a modified (daughter) strain that produces a cell broth that has a reduced viscosity (i.e., reduced resistance to shear or tensile stress) compared to an equivalent cell broth produced by a parental strain. For example, equivalent cell broths generally have comparable cell masses. Methods for constructing reduced viscosity filamentous fungal strains, and methods for comparing the viscosities thereof, are described in detail in International PCT Publication Nos. WO2012/027580, WO2012/145596, WO2012/145596 and WO2012/145592, and International PCT Application Serial No. PCT/US2019/27590 (each specifically incorporated herein by reference in its entirety).

Thus, in certain embodiments, a variant strain of the disclosure (e.g., a variant strain comprising a genetic modification encoding allele lov(T813K) comprising an enhanced/increased protein productivity phenotype, the variant strain further comprises a genetic modification of a gene encoding a MPG1, SFB3, SEB1, CRZ1, GAS1, TPS2 and/or SSB7 protein.

As used herein, a *Trichoderma* sp. "MPG1 protein" comprises an amino acid sequence of SEQ ID NO: 5 (described in International PCT Publication No. WO2012/145584, incorporated herein by reference in its entirety).

As used herein, a *Trichoderma* sp. "SEB1 protein" comprises an amino acid sequence of SEQ ID NO: 6 (described in International PCT Publication No. WO2012/145595, incorporated herein by reference in its entirety).

As used herein, a *Trichoderma* sp. "SFB3 protein" comprises an amino acid sequence of SEQ ID NO: 7, (described in International PCT Publication No. WO2012/027580, incorporated herein by reference in its entirety).

As used herein, a *Trichoderma* sp. "CRZ1 protein" comprises an amino acid sequence of SEQ ID NO: 8 (as described in International PCT Publication No. WO2012/145596, incorporated herein by reference in its entirety).

As used herein, a *Trichoderma* sp. "GAS1 protein" comprises an amino acid sequence of SEQ ID NO: 9 (as described in International PCT Publication Nos. WO2012/145596 and WO2012/145592, each incorporated herein by reference in their entirety).

As used herein, a *Trichoderma* sp. "TSP2 protein" comprises an amino acid sequence of SEQ ID NO: 10 (as described in International PCT Publication No. WO2012/145598, incorporated herein by reference in its entirety).

As used herein, a wild-type "ssb7 gene" encodes a native "SSB7 protein", described in International PCT Application Serial No. PCT/US2019/27590, filed Apr. 16, 2019. For example, a wild-type *T. reesei* "ssb7 gene" (SEQ ID NO: 20) encodes a native "SSB7 protein" of SEQ ID NO: 21.

As used herein, "allele ssb7(fs)" (SEQ ID NO: 22) encodes a variant SSB7 protein of SEQ ID NO: 23, as described in International PCT Application Serial No. PCT/US2019/27590 (specifically incorporated herein by reference in its entirety).

II. Filamentous Fungal Strains Comprising Enhanced Protein Productivity Phenotypes As generally set forth above, and further described in the Examples section below, certain embodiments of the disclosure are related to mutant and genetically modified (variant) strains of filamentous fungus derived from parental strains. More particularly, certain embodiments are related to mutant and genetically modified (variant) strains of filamentous fungus (and methods thereof), wherein such strains comprise enhanced protein productivity phenotypes, such as improved volumetric efficiencies, higher specific productivities, improved yield on carbon sources, reduced bioreactor (fermentor) operating costs and the like.

More particularly, as further described below in Example 1, a mutant (daughter) *Trichoderma* strain was identified, isolated and named "B7ms1-SF12", which (mutant) strain had a 40% higher protein yield on fed sugars in fermentors relative to the parental strain (B7ms1) from which it was derived (e.g., see, FIG. 1). Genome sequence analysis and genetic analysis were subsequently performed on the mutant B7ms1-SF12 strain to identify one or more mutation(s) in a gene (or genes) therein, as being responsible for the observed (increased productivity) phenotype of the B7ms1-SF12 (mutant) strain. More specifically, the identified mutation was determined to alter the coding sequence of the (native) LOV protein of SEQ ID NO: 2, wherein a highly-conserved threonine (T) at amino acid (residue) position 813 (T813) of the (native) LOV protein (SEQ ID NO: 2) was mutated (substituted) to a lysine at position 813 (813K) of the (variant) LOV protein of SEQ ID NO: 4 (i.e., a T813K substitution; e.g., see FIG. 2).

A review of the scientific literature and related art indicate that the functional characterization of the LOV protein (SEQ ID NO: 2) and/or related LOV protein orthologues (e.g., SEQ ID NOs: 11-17) have not been described in the literature for any organism. However, as generally set forth in Example 1 of the disclosure, a conserved domain analysis (NCBI) identified a (conserved) region distantly related to a glycosyl transferase family group 2 (pfam13632, E-value of 3.25×10-44, e.g., see "Glyco trans 2 3" in FIG. 2). For example, members of this (glycosyl transferase) family of prokaryotic proteins include putative glucosyltransferases, which are involved in bacterial capsule biosynthesis (PFAM). More particularly, a fungal protein with the (glycosyl transferase) family group 2 domain, "ZtGT2", orthologous to *Trichoderma* PID 79396 (i.e., which is not LOV, PID 50212), is important for hyphal growth on solid surfaces (King et al., 2017).

Most surprisingly, the LOV protein is widely conserved among filamentous fungi of Basidiomycetes and Ascomycete phyla. For example, the threonine (T) at position 813 of the (native) LOV protein (i.e., which mutation to lysine (K) is beneficial as disclosed herein) is highly conserved (691/691; 100%) among the top BLASTp search results of the NCBI non-redundant database, within the Pezizomycotina subphylum, to which *Trichoderma* and most industrially relevant filamentous fungi belong. For example, a graphical representation from a Geneious multiple sequence alignment (www.geneious.com, Geneious 11.0, Biomatters Ltd.) of these 691 Pezizomycotinahomologs is presented in FIG. 2. Likewise, among the top 1,000 BLASTp hits, amino acid residue position 813 was identical in 975/1000 (97.5%) hits (i.e., residue T813) in a MUSCLE multiple sequence alignment (Geneious software package), wherein residue position 813 never occurs as a lysine (K) (i.e., the substitution described herein resulting in enhanced protein productivity was not found in the top 1000 orthologs identified by BLASTp).

Thus, to further validate that the lov(T813K) allele was causative for the observed enhanced protein productivity phenotypes, the lov(T813K) mutation was introduced into a different *T. reesei* strain lineage named "T4" (e.g., see TABLE 1), wherein the B7ms1 and T4 parental lineages are both mutagenized derivatives from different strain improvement programs of *Trichoderma* strain RL-P37 (Sheir-Neiss et al., 1984; Montenecourt, 1987). For example, the T4 strain notably differs from the B7ms1 strain in that the T4 strain expresses its (endogenous) native cocktail of cellulases and comprises a nik1(M743T) mutation which increases total protein production (e.g., see International PCT Publication No. WO2016/130523). Likewise, similar to the observed results of B7 ms1 lineage set forth in Example 1, the T4 lineage (strains) comprising the lov (T813K) allele (e.g., see Example 2 and Example 4), had on average a 34% higher total protein yield on fed sugars relative to otherwise isogenic strains comprising the wild-type lov(+) allele.

In addition, to further demonstrate utility of the lov (T813K) allele for improvement of fungal strain protein productivity phenotypes, Applicant integrated a pyr2 marker at three other convenient genomic locations (i.e., named sites A-C; also see Example 4, TABLE 1 and TABLE 2). For example, protein production by these different strains was evaluated in shake flasks, where in all such cases, the presence of the lov(T813K) mutation improved total protein production relative to the otherwise isogenic (parental) strains comprising the wild-type lov(+) allele.

III. Molecular Biology

As generally described above, certain embodiments of the disclosure are related to mutant and genetically modified (variant) strains of filamentous fungus derived from parental strains. More particularly, certain embodiments are related to mutant and genetically modified (variant) strains of filamentous fungus (and methods thereof), wherein such strains comprise enhanced protein productivity phenotypes, such as improved volumetric efficiencies, higher specific productivities, improved yield on carbon sources, reduced bioreactor (fermentor) operating costs and the like.

Thus, certain embodiments of the disclosure are related to mutant (daughter) *Trichoderma* strains (e.g., mutant B7ms1-SF12) derived from parental *Trichoderma* strains (e.g., parent B7ms1), wherein the mutant (daughter) *Trichoderma* strains comprise a mutant lov gene encoding a variant LOV protein comprising a lysine (K) residue at an amino acid position corresponding to amino acid residue position 813 of SEQ ID NO: 4.

Certain other embodiments of the disclosure are therefore related to genetically modified strains (hereinafter, "variant" strains) of filamentous fungus derived from parental strains described herein. For example, in certain embodiments, variant strains of filamentous fungus comprise a modified lov gene (or a modified polynucleotide sequence thereof) encoding a variant LOV protein comprising sequence homology to SEQ ID NO: 2 (i.e., the native LOV protein sequence) and comprise a lysine (K) residue at an amino acid sequence position corresponding to amino acid position 813 of SEQ ID NO: 4.

Thus, in certain embodiments, variants strains of the disclosure comprise a modified lov gene (or a modified polynucleotide sequence thereof) encoding a LOV protein comprising at least about 50% to about 100% sequence homology to a LOV protein of SEQ ID NO: 2 (or SEQ ID NO: 4), and comprising a lysine (K) residue at an amino acid sequence position corresponding to amino acid position 813 of SEQ ID NO: 4. In certain embodiments, variants strains of the disclosure comprise a modified lov gene (or a modified polynucleotide sequence thereof) encoding a LOV protein comprising at least about 50% to about 100% sequence identity to a LOV protein of SEQ ID NO: 2 (or SEQ ID NO: 4), and comprising a lysine (K) residue at an amino acid sequence position corresponding to amino acid position 813 of SEQ ID NO: 4.

Thus, in other embodiments, variants strains of the disclosure comprise a modified lov gene (or a modified polynucleotide sequence thereof) encoding a LOV protein comprising at least about 50% sequence homology or identity to SEQ ID NO: 2 or SEQ ID NO: 4, at least 55% sequence homology or identity to SEQ ID NO: 2 or SEQ ID NO: 4, at least 60% sequence homology or identity to SEQ ID NO: 2 or SEQ ID NO: 4, at least 65% sequence homology or identity to SEQ ID NO: 2 or SEQ ID NO: 4, at least 70% sequence homology or identity to SEQ ID NO: 2 or SEQ ID NO: 4, at least 75% sequence homology or identity to SEQ ID NO: 2 or SEQ ID NO: 4, at least 80% sequence homology or identity to SEQ ID NO: 2 or SEQ ID NO: 4, at least 85% sequence homology or identity to SEQ ID NO: 2 or SEQ ID NO: 4, at least 90% sequence homology or identity to SEQ ID NO: 2 or SEQ ID NO: 4, at least 95% sequence homology or identity to SEQ ID NO: 2 or SEQ ID NO: 4, or up to and about 100% sequence homology or identity to SEQ ID NO: 2 or SEQ ID NO: 4, and comprising a lysine (K) residue at an amino acid sequence position corresponding to amino acid position 813 of SEQ ID NO: 4.

Thus, in certain embodiments, variant strains of filamentous fungus comprise at least a genetic modification which introduces allele lov(T813K) into the strain. For example, in certain embodiments, variant strains of filamentous fungus may comprise genetic modifications including, but is not limited to: (a) the introduction, substitution, or removal of one or more nucleotides in a gene (or ORF or polynucleotide thereof), or the introduction, substitution, or removal of one or more nucleotides in a regulatory element required for the transcription or translation of the gene, (b) a gene disruption, (c) a gene conversion, (d) a gene deletion, (e) a gene down-regulation, (f) specific mutagenesis and/or (g) random mutagenesis. In other embodiments, variant strains of filamentous fungus comprising allele lov(T813K) further comprises one or more genetic modifications of a gene encoding NIK1 protein, an SSB7 protein, a MPG1 protein, SFB3 protein, SEB1 protein, CRZ1 protein, a TSP2 protein and/or GAS1 protein, as described herein.

Thus, in certain embodiments, variant strains of filamentous fungus comprising a genetic modification may be constructed by gene deletion to eliminate the expression/production of given gene product (e.g., LOV(+), NIK1, SSB7, MPG1 SFB3, SEB1, CRZ1, TSP2, GAS1, endogenous (background) proteases, cellulases and the like). In other embodiments, variant strains of filamentous fungus comprising a genetic modification may be constructed by partial gene deletion to eliminate (or reduce) the expression/production of a given gene product. For example, in certain embodiments, modified filamentous fungal strains may comprise a partial deletion of a gene, wherein a partial deletion includes the partial deletion of any portion of the gene's coding sequence. For example, in certain embodiments, such variant strains do not express/produce the encoded protein, or such variant strains express/produce a reduced amount of the encoded protein (relative to the parental strain), wherein a "reduced" amount of the encoded protein can be measured, detected, assayed and the like as described herein.

Thus, as generally set forth and described in the Examples section, one skilled in the art may perform the following genetic modifications (and molecular biology methods thereof described in this section) and construct such (variant) filamentous fungus strains thereof, by reference to one or more amino acid sequences (SEQ ID NOs: 2, 4, 11-19) and/or nucleic acid sequences (SEQ ID NOs: 1 and 2) of the instant disclosure.

For example, gene deletion techniques enable the partial or complete removal of the gene, thereby eliminating or reducing expression/production of the protein, and/or thereby eliminating or reducing expression/production the encoded protein. In such methods, the deletion of the gene may be accomplished by homologous recombination using an integration plasmid/vector that has been constructed to contiguously contain the 5' and 3' regions flanking the gene. The contiguous 5' and 3' regions may be introduced into a filamentous fungal cell, for example, on an integrative plasmid/vector in association with a selectable marker to allow the plasmid to become integrated in the cell.

In other embodiments, a variant strain of filamentous fungus comprises genetic modification which disrupts or inactivates a gene encoding a protein of the disclosure. Exemplary methods of gene disruption/inactivation include disrupting any portion of a gene, including the polypeptide coding sequence (CDS), promoter, enhancer, or another regulatory element, which disruption includes substitutions, insertions, deletions, inversions, and combinations thereof and variations thereof. Thus, in certain embodiments, a variant strain of filamentous fungus is constructed by a gene disruption technique. A non-limiting example of a gene disruption technique includes inserting (integrating) into one or more of the genes of the disclosure an integrative plasmid containing a nucleic acid fragment homologous to the gene, which will create a duplication of the region of homology and incorporate (insert) vector DNA between the duplicated regions.

Thus, in certain other non-limiting examples, a gene disruption technique includes inserting into a gene an integrative plasmid containing a nucleic acid fragment homologous to the gene, which will create a duplication of the region of homology and incorporate (insert) vector DNA between the duplicated regions, wherein the vector DNA inserted separates, e.g., the promoter of the gene from the protein coding region, or interrupts (disrupts) the coding, or non-coding, sequence of the gene. Thus, a disrupting construct may be a selectable marker gene (e.g., pyr2; see Examples) accompanied by 5' and 3' regions homologous to the gene. The selectable marker enables identification of transformants containing the disrupted gene. Thus, in certain embodiments, gene disruption includes modification of control elements of the gene, such as the promoter, ribosomal binding site (RBS), untranslated regions (UTRs), codon changes, and the like.

In other embodiments, a variant strain of filamentous fungus is constructed (i.e., genetically modified) by introducing, substituting, or removing one or more nucleotides in the gene, or a regulatory element required for the transcription or translation thereof. For example, nucleotides may be inserted or removed so as to result in the introduction of a stop codon, the removal of the start codon, or a frame-shift of the open reading frame (ORF). Such a modification may be accomplished by site-directed mutagenesis or PCR generated mutagenesis in accordance with methods known in the art (e.g., see, Botstein and Shortle, 1985; Lo et al., 1985; Higuchi et al., 1988; Shimada, 1996; Ho et al., 1989; Horton et al., 1989 and Sarkar and Sommer, 1990). Likewise, allele lov(T813K) comprising the T813K substitution described herein may be constructed by substituting nucleotides encoding the position 813 threonine of the wild-type lov(+) gene for nucleotides encoding the position 813 lysine of allele lov(T813K).

In other embodiments, a variant strain of filamentous fungus is constructed (i.e., genetically modified) by the process of gene conversion (e.g., see Iglesias and Trautner, 1983). For example, in the gene conversion method, a nucleic acid sequence corresponding to the target gene is mutagenized in vitro to produce a defective nucleic acid sequence, which is then transformed into the parental cell to produce a variant cell comprising a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993).

In other embodiments, a variant strain of filamentous fungus is constructed by established anti-sense (gene-silencing) techniques, using a nucleotide sequence complementary to the nucleic acid sequence of the gene (Parish and Stoker, 1997). More specifically, expression of a gene by a filamentous fungus strain may be reduced (down-regulated) or eliminated by introducing a nucleotide sequence complementary to the nucleic acid sequence of the gene, which is transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a variant strain of filamentous fungus is constructed (i.e., genetically modified) by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the gene has been reduced or eliminated. For example, one of skill in the art may readily adapt and/or modify the screening methods set forth in the Example section herewith to identify such (mutagenized) variant strains of filamentous fungus cells comprising a reduced viscosity phenotype.

The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods. Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

For example, such genetic modifications in the one or more of the genes disclosed herein can reduce the efficiency of the gene's promoter, reduce the efficiency of an enhancer, interfere with the splicing or editing of the gene's mRNA, interfere with the translation of the gene's mRNA, introduce a stop codon into the gene's-coding sequence to prevent the translation of full-length protein, change the coding sequence of the protein to produce a less active or inactive protein, reduce the protein interaction with other nuclear protein components, change the coding sequence of the protein to produce a less stable protein, or target the protein for destruction, or cause the protein to misfold or be incorrectly modified (e.g., by glycosylation), or interfere with cellular trafficking of the protein.

In certain other embodiments, a variant strain of filamentous fungus is constructed (i.e., genetically modified) by means of site specific gene editing techniques. For example, in certain embodiments, a variant strain of filamentous fungus is constructed (i.e., genetically modified) by use of transcriptional activator like endonucleases (TALENs), zinc-finger endonucleases (ZFNs), homing (mega) endonuclease and the like. More particularly, the portion of the gene to be modified (e.g., a coding region, a non-coding region, a leader sequence, a pro-peptide sequence, a signal sequence, a transcription terminator, a transcriptional activator, or other regulatory elements required for expression of the coding region) is subjected genetic modification by means of ZFN gene editing, TALEN gene editing, homing (mega) endonuclease and the like, which modification methods are well known and available to one skilled in the art.

Thus, in certain embodiments, a variant strain of filamentous fungus is constructed (i.e., genetically modified) by means of CRISPR/Cas9 editing. More specifically, compositions and methods for fungal genome modification by CRISPR/Cas9 systems are described and well known in the art (e.g., see, International PCT Publication Nos: WO2016/100571, WO2016/100568, WO2016/100272, WO2016/100562 and the like). For example, a gene encoding a native LOV protein can be genetically modified by means of nucleic acid guided endonucleases, that find their target DNA by binding either a guide RNA (e.g., Cas9) or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (e.g., a Cas9 from *S. pyogenes*, or a codon optimized gene encoding the Cas9 nuclease) is operably linked to a promoter active in the filamentous fungal cell and a terminator active in filamentous fungal cell, thereby creating a filamentous fungal Cas9 expression cassette. Likewise, one or more target sites unique to the gene of interest are readily identified by a person skilled in the art.

For example, to build a DNA construct encoding a gRNA-directed to a target site within the gene of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a filamentous fungal expression cassette for the gRNA is created by operably linking the DNA encoding the gRNA to a promoter active in filamentous fungal cells and a terminator active in filamentous fungal cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the filamentous fungal host's machinery to repair the DNA break generated by the RGEN (RNA-guided endonuclease).

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR, by amplifying the target locus with a forward and reverse primer. These primers can amplify the wild-type locus or the modified locus that has been edited by the RGEN. These fragments are then sequenced using a sequencing primer to identify edited colonies.

IV. Proteins of Interest

As briefly stated in the preceding section, the present strains and methods find use in the production of commercially important proteins in submerged cultures of filamentous fungi. A protein of interest (POI) of the instant disclosure can be any endogenous or heterologous protein, and it may be a variant of such a POI. The protein can contain one or more disulfide bridges or is a protein whose functional form is a monomer or a multimer, i.e., the protein has a quaternary structure and is composed of a plurality of identical (homologous) or non-identical (heterologous) subunits, wherein the POI or a variant POI thereof is preferably one with properties of interest.

In certain embodiments, a variant strain of filamentous fungus exhibits an increased protein titer relative to the (unmodified) parental strain, wherein protein titer is defined as the amount of protein per volume (g/L). For example, titers can be measured by methods known in the art (e.g., ELISA, HPLC, Bradford assay, LC/MS and the like). Thus, in certain embodiments, a variant strain of filamentous fungus comprises a protein titer increase of at least about 0.1%, at least about 1%, at least about 5%, at least about 6%, at least about 7%, at least about 8%, at least about 9%, or at least about 10% or more as compared to the unmodified (parental) cell.

In certain embodiments, a variant strain of filamentous fungus exhibits an increased volumetric productivity relative to the (unmodified) parental strain, wherein volumetric productivity is defined as the amount of protein produced (g) during the fermentation per nominal volume (L) of the bioreactor per total fermentation time (h). For example, volumetric productivities can be measured by methods know in the art (e.g., ELISA, HPLC, Bradford assay, LC/MS and the like). Thus, in certain embodiments, a variant strain of filamentous fungus comprises a volumetric productivity increase of at least about 0.1%, at least about 1%, at least about 5%, at least about 6%, at least about 7%, at least about 8%, at least about 9%, or at least about 10% or more as compared to the unmodified (parental) cell.

In certain other embodiments, a variant strain of filamentous fungus exhibits an increased total protein yield, wherein total protein yield is defined as the amount of protein produced (g) per gram of carbohydrate fed, relative to the (unmodified) parental strain. Thus, as used herein, total protein yield (g/g) may be calculated using the following equation:

$$Y_f = T_P/T_c$$

wherein "$Y_f$" is total protein yield (g/g), "$T_p$" is the total protein produced during the fermentation (g) and "$T_c$" is the total carbohydrate (g) fed during the fermentation (bioreactor) run. In certain embodiments, the increase in total protein yield of the modified strain (i.e., relative to the parental strain) is an increase of at least about 0.1%, at least about 1%, at least about 5%, at least about 6%, at least about 7%, at least about 8%, at least about 9%, or at least about 10% or more as compared to the unmodified (parental) cell.

Total protein yield may also be described as carbon conversion efficiency/carbon yield, for example, as in the percentage (%) of carbon fed that is incorporated into total protein. Thus, in certain embodiments, a variant strain of filamentous fungus comprises an increased carbon conversion efficiency (e.g., an increase in the percentage (%) of carbon fed that is incorporated into total protein), relative to the (unmodified) parental strain. In certain embodiments, the increase in carbon conversion efficiency of the modified strain (i.e., relative to the parental strain) is an increase of at least about 0.1%, at least about 1%, at least about 5%, at least about 6%, at least about 7%, at least about 8%, at least about 9%, or at least about 10% or more as compared to the unmodified (parental) cell.

In certain embodiments, a variant strain of filamentous fungus exhibits an increased specific productivity (Qp) of a POI relative the (unmodified) parental strain. For example, the detection of specific productivity (Qp) is a suitable method for evaluating rate of protein production. The specific productivity (Qp) can be determined using the following equation:

$$\text{"}Qp = gP/gDCW \cdot hr\text{"}$$

wherein, "gP" is grams of protein produced in the tank; "gDCW" is grams of dry cell weight (DCW) in the tank and "hr" is fermentation time in hours from the time of inoculation, which includes the time of production as well as growth time. Thus, in certain embodiments, a variant strain of filamentous fungus comprises a specific productivity (Qp) increase of at least about 0.1%, at least about 1%, at least about 5%, at least about 6%, at least about 7%, at least about 8%, at least about 9%, or at least about 10% or more as compared to the unmodified (parental) cell.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannanases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

In certain embodiments, a POI or a variant POI thereof is selected from an Enzyme Commission (EC) Number selected from the group consisting of EC 1, EC 2, EC 3, EC 4, EC 5 or EC 6.

For example, in certain embodiments a POI is an oxidoreductase enzyme, including, but not limited to, an EC1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase), EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1,4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase), EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., *Aspergillus* nuclease Si), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase I), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1,6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase), EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofuranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-O-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetyl-glucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase I), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin), EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.—(e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1→4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate: coenzyme A ligase) and EC 6.3.2.28 (e.g., L-amino-acid alpha-ligase).

These and other aspects and embodiments of the present strains and methods will be apparent to the skilled person in view of the present description and the following Examples.

EXAMPLES

Certain aspects of the present disclosure may be further understood in light of the following examples, which should not be construed as limiting. Modifications to materials and methods will be apparent to those skilled in the art.

Example 1

Identification of the lov Gene as being Responsible for Protein Production Increases in Filamentous Fungi

A. Overview

In the present example, a reduced viscosity *Trichoderma* strain named "B7ms1", expressing a glucoamylase (GA) construct, was specifically evolved towards reducing the propensity to pellet under shake flask conditions. More particularly, a mutant (strain) of B7ms1 was identified, isolated and named "B7ms1-SF12". The (mutant) B7ms1-SF12 strain had a 40% higher protein yield on fed sugars in fermentors relative to the B7ms1 (parental) strain (e.g., see, FIG. 1).

Thus, as described herein, genome sequence analysis and genetic analysis were performed on the B7ms1-SF12 (mutant) strain, to identify one or more mutation(s) in a gene (or genes) therein, as being responsible for the observed (increased productivity) phenotype of the B7ms1-SF12 (mutant) strain. As disclosed herein, the identified mutation was determined to alter the coding sequence of the (native) LOV protein, wherein a highly-conserved threonine (T) at amino acid (residue) position 813 (T813) of the (native) LOV protein (SEQ ID NO: 2) was changed (substituted) to a lysine at position 813 (813K) of the (variant) LOV protein (SEQ ID NO: 4, i.e., a T813K substitution) (see FIG. 2).

B. Evolution Strategy

Filamentous fungal species (e.g., *Trichoderma* sp., *Aspergillus* sp., *Fusarium* sp., *Penicillium* sp., *Chrysosporium* sp., *Cephalosporium* sp., *Talaromyces* sp., *Geosmithia* sp., *Neurospora* sp., *Myceliophthora* sp. and the like) are aerobic fungi that generally produce a thick, viscous fermentation broth when used in commercial/industrial fermentations. The high fermentation (broth) viscosity typically reduces dissolved oxygen (DO) transfer, thereby limiting the amount of cell mass and reducing the volumetric productivity that can be achieved in such aerobic filamentous fungus fermentations. For example, isolation of reduced viscosity filamentous fungal mutants has resulted in mutant strains/cells that produce lower viscosity fermentation broths, wherein fermentations using such reduced viscosity strains/cells can utilize more cell mass leading to increases in protein productivity (e.g., see Applicant's International PCT Publication Nos. WO2012/145584, WO2012/027580, WO2012/145595, WO2012/145596 and WO2012/145592). More particularly, as Applicant began to combine certain reduced viscosity mutations to generate further reduced viscosity strains thereof, it was surprisingly observed that certain viscosity (reducing) combinations (i.e, mutations) thereof seemed to have a greater propensity to form mycelial pellets in shake flask assays.

More particularly, as contemplated herein, in the event that the observed increased propensity to form mycelial pellets in shake flasks may scale to fermentors, Applicant sought to mitigate the aforementioned pelting phenotype by means of directed evolution experimentation. For example, without wishing to be bound by any particular theory, mechanism or mode of action, it is contemplated herein that such propensity to form mycelial pellets may negatively interfere with protein production and/or the downstream processing of such proteins. Applicant therefore rationalized that "evolved" mutants of these strains could be generated, screened and isolated, wherein such evolved strains comprise a reduced propensity for mycelial pelleting in shake flasks, fermentors, bioreactors and the like.

For example, cultures of *Trichoderma* strain B7ms1 were grown for 12-24 hours in shake flasks containing complete complex media, then passed through a 70 micrometer (μm) sieve. The flow through, depending on the cell density, was used to inoculate fresh culture media, or the whole of the flow through was transferred to a fresh shake flask. After incubation, the process was repeated serially for weeks, occasionally taking samples that were then plated to isolate possible mutants. Isolates were (individually) visually screened for gross changes in shake flask morphology (e.g., changes in shake flask morphology including, but not limited to, pelleting or mycelia chunkiness). Those isolates with more homogeneous growth in shake flasks were additionally tested for protein production in shake flasks, and then in fermentors.

C. Isolation and Characterization of *Trichoderma* Mutant Strain B7ms1-Sf12

In such an evolution scheme set forth above, Applicant isolated a mutant strain named "B7ms1-SF12", wherein the (mutant) B7ms1-SF12 strain demonstrated higher protein production in shake flasks, relative to the (parental) B7ms1 strain (data not shown). Thus, independent of any influence on the aforementioned pelleting phenotype, any mutation(s) enhancing the protein production phenotype of the host strain is of particular value in its potential to reduce fermentation/protein production costs.

Thus, the (parental) B7 ms1 strain and the spontaneous mutant (daughter) strain B7 ms1-SF12 were assayed for total protein production in fermentors. These strains were grown under identical conditions in submerged (liquid culture), and their total protein yield on fed sugars compared in 14 L fermentors. As presented in FIG. 1, the mutant B7ms1-SF12 strain (FIG. 1; black line/black squares) showed a 44% increased improvement in yield on fed sugars vis-à-vis the (parental) B7 ms1 strain (FIG. 1; grey line/grey squares).

Briefly, spores of each strain were added separately to 500 mL of medium in a 3 L flask with both side and bottom baffles. The cultures were grown in a minimal medium for 48 hours at 34° C. in a shaking incubator. After 48 hours, the contents of each flask were added separately to 14 L fermentors containing 9.5 L of medium containing 4.7 g/L KHPO, 1.0 g/L MgSO$_7$HO, 4.3 g/L (NH)SO and 2.5 mL/L of 400× *T. reesei* trace elements solution (citric Acid (anhydrous), 175 g/L; FeSO$_4$·7 H$_2$O, 200 g/L, ZnSO$_4$·7 H$_2$O, 16 g/L, CuSO$_4$·5 H$_2$O, 3.2 g/L; MnSO$_4$H$_2$O, 1.4 g/L; H$_3$BO$_3$, 0.8 g/L.). These components were heat sterilized together at 121° C. for 30 minutes. A solution of 60% glucose and 0.48% CaCl$_2$·2 H$_2$O was separately autoclaved, cooled, and added to the fermentor to a final concentration of 75 g/L glucose and 0.6 g/L CaCl$_2$·2 H$_2$O. The medium was adjusted to pH 3.5 with 28% NH and the temperature was maintained at 34° C. during the growth period. Once glucose was exhausted, the temperature was dropped to 28° C., and the cultures were fed glucose-sophorose. The dry cell weight (DCW), total protein concentrations and other parameters were measured, and specific total protein production rates and yield on fed sugars were calculated.

D. Identification of the Causative lov(T813K) Mutation in *Trichoderma* Mutant Strain B7ms1-SF12

Applicant sequenced the genomes of the (parental) B7ms1 strain and the (mutant) B7ms1-SF12 (daughter) strain, leading to the identification of two (2) new mutations predicted to alter a coding sequence in the B7ms1-SF12 genome, either of which mutations alone (or in combination), could have been necessary for the observed protein productivity (improvement) phenotypes. More particularly, to determine/identify which of these mutations were of importance, complementation analysis was used by transforming the (mutant) B7ms1-SF12 strain with DNA encoding each of the wild-type loci. For example, only one locus when transformed complemented the mutant phenotype, which locus was called lov. The lov gene encodes the predicted protein PID 50212 (SEQ ID NO: 2), wherein in the (mutant) B7ms1-SF12 strain the lov mutant (allele) comprises a single nucleotide change of G (guanine) to T (thymine) at 425393 on Scaffold 16, resulting in amino acid substitution T813K in the encoded LOV (variant) protein (SEQ ID NO: 4), which mutant allele is referred to herein as allele "lov(T813K)" and the native (wild-type) allele is referred to herein as "lov(+)".

Functional characterization of the LOV protein or LOV protein orthologues, has not been described in the literature for any organism. As described herein, a conserved domain analysis (NCBI) identified a region distantly related to a glycosyl transferase family group 2 (pfam13632, E-value of 3.25×10-44, e.g., see "Glyco trans 2 3" in FIG. 2). For example, members of this (glycosyl transferase) family of prokaryotic proteins include putative glucosyltransferases, which are involved in bacterial capsule biosynthesis (PFAM). More particularly, a fungal protein with the (glycosyl transferase) family group 2 domain, "ZtGT2", orthologous to Trichoderma PID 79396 (i.e., which is not LOV, PID 50212), is important for hyphal growth on solid surfaces (King et al., 2017).

Figure 2:
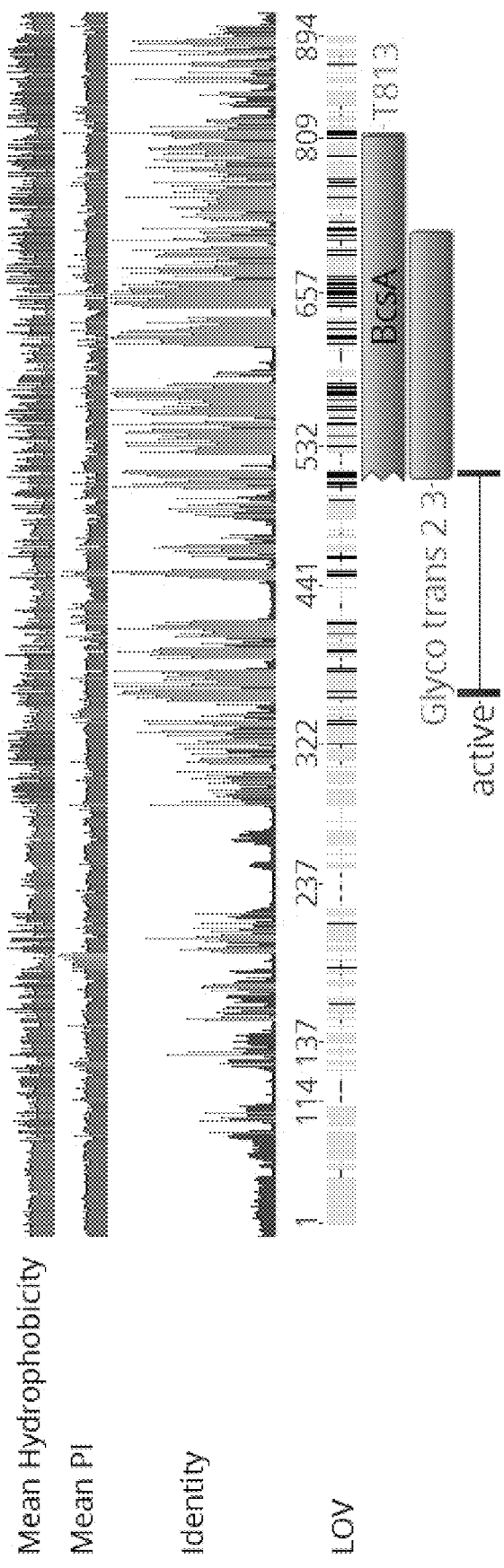
FIG. 2 is a graphical representation illustrating amino acid conservation of the LOV protein. More specifically.

Most surprisingly, the LOV protein is widely conserved among filamentous fungi of Basidiomycetes and Ascomycete phyla. For example, the threonine (T) at position 813 of the (native) LOV protein (i.e., which mutation to lysine (K) is beneficial as disclosed herein) is highly conserved (691/691; 100%) among the top BLASTp search results of the NCBI non-redundant database, within the Pezizomycotina subphylum, to which Trichoderma and most industrially relevant filamentous fungi belong. A graphical representation from a Geneious multiple sequence alignment (www.geneious.com, Geneious 11.0, Biomatters Ltd.) of these 691 Pezizomycotina homologs is presented in FIG. 2. Likewise, among the top 1,000 BLASTp hits, residue position 813 was identical in 975/1000 (97.5%) hits (i.e., T813) in a MUSCLE multiple sequence alignment (Geneious software package), wherein residue 813 never occurs as a lysine (K) (i.e., the substitution described herein resulting in enhanced protein productivity was not found in the top 1000 orthologs identified by BLASTp). While a conserved position and mutation is useful for improving fungal protein production, the T813 residue is not within any of the regions previously annotated in Genebank (FIG. 2). The LOV protein is the only predicted member of this class of proteins in the Trichoderma genome, whereas many genomes have more than one.

Example 2

Targeted Introduction of the lov(T813K) Allele in Reduced Viscosity Strains Increases Protein Productivity in Fermentors A. Overview To further validate that the lov(T813K) allele was causative for the observed protein productivity improvements, the lov(T813K) mutation was introduced into a different T. reesei strain lineage (herein named "T4"). B7ms1 (Example 1) and T4 lineages are both mutagenized derivatives from different strain improvement programs of Trichoderma strain RL-P37 (Sheir-Neiss et al., 1984; Montenecourt, 1987). The T4 strain notably differs from B7ms1 in that the T4 strain expresses the native cocktail of cellulases and contains a nik1(M743T) mutation that increases total protein production (US20180037919). As before with the B7ms1 linage (Example 1), reduced viscosity double mutants (Δmpg1; Δseb1) were developed in the T4 lineage both with or without the presence of the lov(T813K) allele. For example, in fermentors, the T4 Δmpg1; Δseb1 strains comprising the lov(T813K) allele had on average, a 37% higher total protein yield on fed sugars.

B. Construction of Plasmids Comprising lov Disruption Cassettes with Either pyr4 or pyr2 Selection Markers The Trichoderma lov disruption cassette plasmids were prepared using standard molecular biology procedures, wherein one of skill in the relevant art may readily recreate this plasmid from the information disclosed herein. The plasmid included a DNA sequence having a 1.6 Kb homology box identical to the DNA sequence corresponding to Scaffold 16, 426947 to 425393 (Left Flank). The last nucleotide of the Left Flank introduced a single nucleotide G to T mutation, corresponding to the mutation identified in the (mutant) B7ms1-SF12 strain (Example 1). Also included within the plasmid was a DNA sequence having a 1.5 Kb homology box corresponding to the DNA sequence identical to Scaffold 16, 425392 to 423880 (Right Flank). These sequences were designed to target the lov gene and replace the nucleotide of the genome between the Left and Right Flanks (Scaffold 16, 425393) with the intervening cassette sequences.

These intervening (cassette) sequences included either a pyr4 selection marker from Trichoderma reesei (pRATT308) or a pyr2 selection marker from Trichoderma atroviride (pRATT312). Immediately downstream of the selection marker was a DNA sequence having a 0.5 Kb region homologous to the 3'-most 0.5 Kb region of the Left Flank (Repeat). These repeated sequences were intended to facilitate the subsequent loss of the selection marker, enabling subsequent use of this marker in future strain development, and leaving the single nucleotide G to T mutation (Scaffold 16, 425393) in the lov gene, encoding the LOV(T813K) protein (SEQ ID NO: 4), as the only new targeted genome modification.

C. Development of T4 Derived Strains with the lov(T813K) Allele

Derivatives of the T4 strain, herein named strain "T4m" and "T4m_pyr2", comprising a viscosity reducing disruption of gene mpg1 (Δmpg1), were developed essentially as described in U.S. Pat. No. 9,725,727 (incorporated herein by referenced in its entirety). Thus, the T4m_pyr2 strain (Δmpg1; pyr2) was transformed with a lov disruption cassette from pRATT312 (pyr2 selection marker), using PEG-mediated transformation and plated on Vogel's minimal medium (Vogel, 1956) containing 1.2 M sorbitol to select for candidates based on uridine prototrophy acquired by the pyr2 marker. Trichoderma transformations are well known and described in the art (e.g., see U.S. Pat. No. 5,246,853). Individual transformants were isolated and propagated by transfer to Vogel's minimal medium. PCR analysis was used to identify transformants in which the lov disruption cassette integrated at the lov locus by homologous recombination, using methods known to one skilled in the art per guidance below.

Only a subset of recombinant cells may successfully utilize the homologous flanks to correctly target the disruption of the gene of interest, so many transformants may need to be screened to identify one with the desired event. PCR can be used to test which recombinant cells have the desired targeted disruption. Primers must be designed that amplify across each of the homology box regions, where one primer primes at a location within the selectable marker greater than 100 bp from the closest end and the other primes at a location greater than 100 bp beyond the end of a homology box region within the adjacent genomic sequence. Cells likely containing the correct targeted disruption will successfully create PCR products spanning the Left Flank and Right Flank of the disruption cassette, whereas unsuccessful transformation events will not generate a product of the expected size. At this stage the culture may be a mix of transformed and untransformed cells, so a step of purification may be needed. Purification of the culture can be tested by PCR for loss of a short PCR product spanning the disruption site.

More particularly, one such T4m derived strain comprising a pyr2 disruption of the lov gene was identified, isolated and named "T4ml+" (i.e., comprising allele lov(dis) in contrast to allele lov(T813K) encoding the specific T813K substitution). Thus, to generate strains comprising the specific lov(T813K) allele, spore suspensions of strain T4ml+ (comprising the lov(dis) allele) were plated on media containing 5-fluoro-orotic acid (FOA) to select for derivative strains in which there was a spontaneous recombination between the repeated regions flanking the inserted selection marker and concomitant loss of the selection marker from the genome. The uridine auxotrophs were isolated and analyzed by PCR to test for loss of the selection marker and sequencing of PCR products to confirm presence of the lov(T813K) allele. One strain comprising the lov(T813K) allele was generated in this manner and is referred to herein as "T4ml". To restore the pyrimidine prototrophy for fermentor evaluation, both the T4ml and T4m_pyr2 strains had the pyr2 marker targeted to the viscosity reducing locus seb1, as essentially described in U.S. Pat. No. 9,725,727, resulting in strains herein referred to as "T4mls" (comprising the lov(T813K) allele) and "T4ms" (comprising the lov(+) allele).

D. Fermentor Evaluation of T4 Derived Strains Comprising the lov(T813K) Allele

Figure 3:
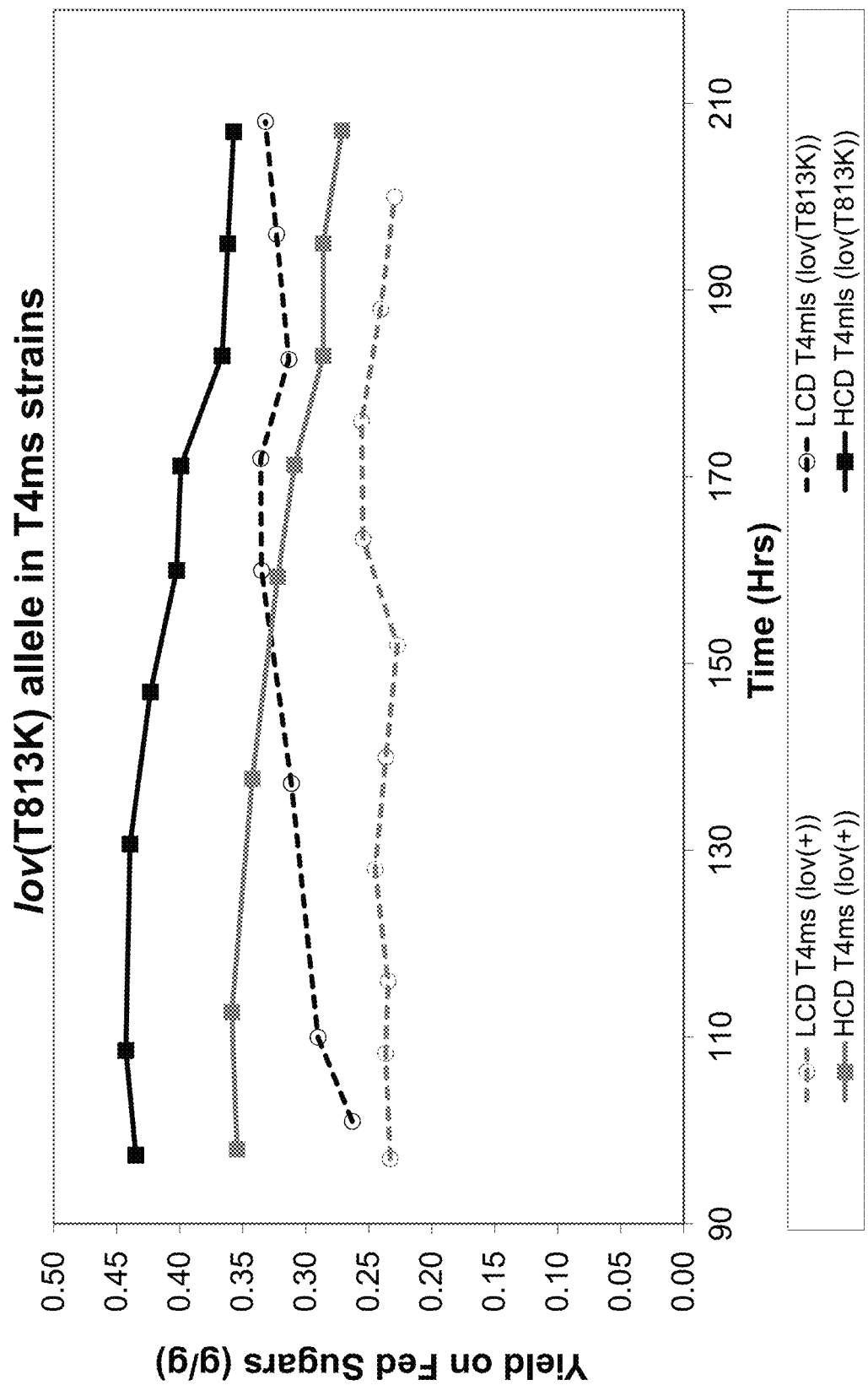
FIG. 3 presents a comparison of total protein yield on fed sugars in fermentors for the whole cellulase producing T4ms strain (grey lines) and mutant derivative T4mls comprising an engineered lov(T813K) allele (black lines). More particularly.

Thus, strains T4mls (comprising the lov(T813K) allele) and T4ms (comprising the lov(+) allele) were evaluated in fermentors as described in Example 1. In addition, the T4mls and T4ms strains were evaluated at a lower cell density fermentation relative to Example 1, by adjusting the amount of glucose provided before feed start, to ensure that the protein production phenotypes observed with the lov (T813K) allele were not limited to higher cell density fermentations. As shown in FIG. 3, under both lower cell density (LCD; FIG. 3, T4mls, black circles/black dashed lines; T4ms, grey circles/grey dashed lines) fermentation conditions and higher cell density (HCD; FIG. 3, T4mls, black squares/black solid lines; T4ms, grey squares/grey solid lines) fermentation conditions, the protein yield on fed sugars increased 42% and 32%, respectively, when the lov(T813K) allele was present.

Example 3

Targeted Disruption of the lov Gene by Insertion of pyr2 Selection Marker Failed to Improve Productivity in Fermentors A. Overview Given the high conservation of the threonine (T) amino acid at residue 813 position of (native) LOV protein (SEQ ID NO: 2), it seemed probable that disruption of the locus in any way that would block the expression/production of the LOV protein, would also improve strain productivity as well. To test this hypothesis, fungal strains with and without the lov(dis) allele were compared in fermentors, wherein a pyr2 selection marker was inserted into the lov gene to disrupt LOV protein expression. Surprisingly, the lov(dis) allele did not improve production in fermentors.

B. Fermentor Evaluation of Strains with the lov(dis) Allele

Development of the T4m and T4ml+ strains are described above in Example 2. Strain T4ml+ is a derivative of T4m in which the pyr2 marker was inserted into the lov coding sequence of stain T4m_pyr2. The T4m and T4ml+ strains were evaluated under identical conditions in 14 L fermentors that were essentially the same as described in Example 1, except at a lower cell density fermentation, by adjusting the amount of glucose provided before feed start.

Figure 4:
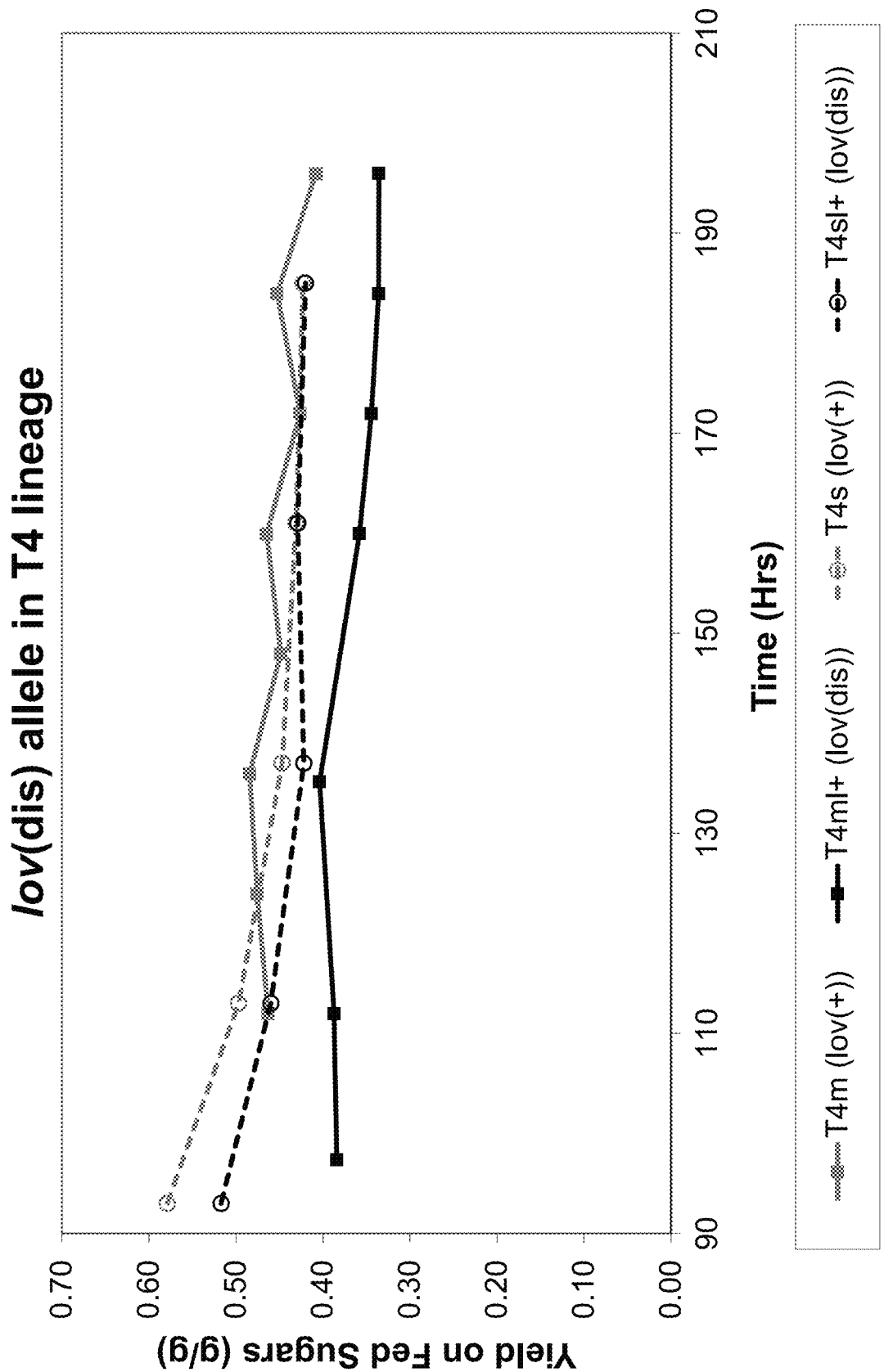
FIG. 4 presents a comparison of total protein yield on fed sugars in fermentors for the whole cellulase producing strains T4m (solid lines, squares) and T4s (dashed lines, circles) with the wild-type lov allele (grey lines) and their mutant derivatives T4ml+(solid lines, squares) and T4sl+ (dashed lines, circles), respectively, comprising an engineered lov(dis) allele (black lines). The figure legend shows the strain name (see TABLE 1 for genotypes) followed by the lov allele in that strain shown in parenthesis for each line type. As presented in FIG. 4, the T4ml+ and T4sl+(daughter) strains (FIG. 4, black lines; i.e., comprising the mutant lov(dis) allele)) do not have an enhanced protein productivity phenotype relative to their T4m and T4s (parental) strains (FIG. 4, grey lines; i.e., comprising the wild-type lov gene).

Derivatives of T4, named "T4s" and "T4s_pyr2" (comprising a viscosity reducing disruption of gene seb1), were developed essentially as described in U.S. Pat. No. 9,725,727. The lov(dis) allele was introduced into T4s_pyr2 analogously as described for strain T4m_pyr2 in Example 2, to generate strain T4sl+. Thus, the T4s and T4sl+ strains were evaluated under identical conditions in 2 L bioreactors. Specifically, for 2 L bioreactors, to create a seed culture, the spores of each strain were added separately to 50 mL of citrate minimal medium in a 250 mL flask. The cultures were grown for 48 h at 30° C. and 170 rpm in a shaking incubator. After 48 hours, 145.6 mL of 50% glucose, and 0.6 g/kg of $CaCl_2$, adjusted to pH 3.5, was inoculated with the seed culture. Thereafter, the temperature was maintained at 34° C., and pH at 3.5. Following exhaustion of batched glucose, a glucose-sophorose feed was thereafter introduced, and the temperature was dropped to 25° C., and pH increased to 4.8. The dry cell weight (DCW), total protein concentrations, and other parameters were measured, and specific total protein production rates and yield on fed sugars were calculated. As shown in FIG. 4, protein yield on fed sugars decreased 17% when the lov(dis) mutation was present in the T4m background and was unchanged when present in the T4s background.

Example 4

Targeted Introduction of the lov(T813K) Allele in Other Fungal Strains Improves Protein Productivity A. Overview In Example 2, the pyr2 auxotrophy generated concomitant with allele lov(T813K) generation and marker loss had been restored by integration of the pyr2 marker at the seb1 locus. Therefore, the improvement in protein production observed with the lov(T813K) allele has thus far been exemplified, in Example 1 and Example 2, in strains always containing both the mpg1 and seb1 viscosity mutations. To demonstrate the more general application of the lov(T813K) allele for improvement of strain productivity, the pyr2 marker was integrated at three other convenient genomic locations: site A, site B and site C. Protein production by these different strains was evaluated in shake flasks, where in all cases, presence of the lov(T813K) mutation improved total protein production relative to the isogenic strains with a wild-type lov(+) allele. On the contrary, strains comprising a lov(dis) mutation did not show significant improvement in protein production in shake flasks.

B. Restored Pyrimidine Auxotrophy in T4ml and T4sl by Targeted Integration of A pyr2 Selection Marker at Different Genomic Locations Strains either with or without the lov(T318K) allele were transformed independently with cassettes targeting integration of pyr2 to three convenient genomic locations named sites A-C, using methods known to one skilled in the art. Briefly, following PEG-mediated transformation with the pyr2 cassettes, protoplasts were plated on Vogel's minimal medium containing 1.2 M sorbitol to select for candidates based on uridine prototrophy acquired by the pyr2 marker. Individual transformants were isolated and propagated by transfer to Vogel's minimal medium. PCR analysis was used to identify transformants in which the pyr2 cassette integrated at the intended genomic location. Following spore purification, further PCR analysis was done to ensure integration occurred correctly and that the transformants were homokaryotic.

Thus, the pyr2 marker was integrated at site A, site B and site C in pyr2 mutant strains T4m_pyr2 (lov(+)) and T4ml (Δmpg1; lov(T318K)) which were described in Example 2 (see, Table 1). Likewise, the pyr2 marker was integrated at site A in mutants strain T4s_pyr2 (Δseb1; lov(+)) and T4sl (Δseb1; lov(T318K)) described in Example 3. In addition, disruption allele lov(dis) was added to whole cellulase strains T4_pyr2 (pyr2; lov(+)) and 41G_pyr4 (pyr4; lov(+)) using plasmids pRATT312 and pRATT308 respectively as described in Example 2.

C. Shake Flask Evaluation of Strains with and without Either the lov(T813K) or lov(dis) Alleles Strains were evaluated in shake flask fermentations for their protein production. The strains evaluated are listed in TABLE 1. In all genetic backgrounds tested, the total protein titers increased when the lov(T813K) allele was present. However, disruption of the lov gene, the lov(dis) allele, with either the pyr4 (41G) or pyr2 marker (T4 and T4m) showed no significant improvement in relative titers.

Liquid defined (LD) culture medium (e.g., see, U.S. Pat. No. 8,455,631), contained the following components. Casamino acids, 9 g/L; $(NH_4)_2SO_4$, 5 g/L; $MgSO_4 \cdot 7H_2O$, 1 g/L; $KH_2PO_4$, 4.5 g/L; $CaCl_2 \cdot 2H2O$, 1 g/L, PIPPS, 33 g/L, 400× *T. reesei* trace elements, 2.5 ml/L; pH adjusted to 5.5 with NaOH. After sterilization, lactose or a glucose/sophorose mixture was added to a final concentration of 1.6% w/v.

To create a seed culture, the spores of each strain were added separately to 50 mL of YEG (5 g/L yeast extract, 22 g/L glucose, $H_2O$) in a 250 mL flask. The cultures were grown for 36-48 hours at 28° C. and 200 rpm in a shaking incubator. After incubation, 0.3 mL of seed culture were added to 50 mL of LD medium in a baffled shake flask. This production culture was grown for 5 days at 28° C. and 180 rpm. Secreted protein was harvested by centrifugation to pellet cells, and then collecting the supernatant. Proteins were precipitated from the supernatant with an equal volume of trichloroacetic acid (TCA), followed by dissolution in 0.1 N sodium hydroxide (NaOH). Total protein was then measured with a BCA protein assay (ThermoFisher Scientific, Grand Island, N.Y., USA) per manufacturer protocol. In all shake flask experiments, prototrophic T4 and T4m strains were included in duplicate. BCA assay numbers were normalized to the average of these controls which were run in parallel to minimize the influence of any week-to-week variation in total protein production efficiency.

Figure 5:
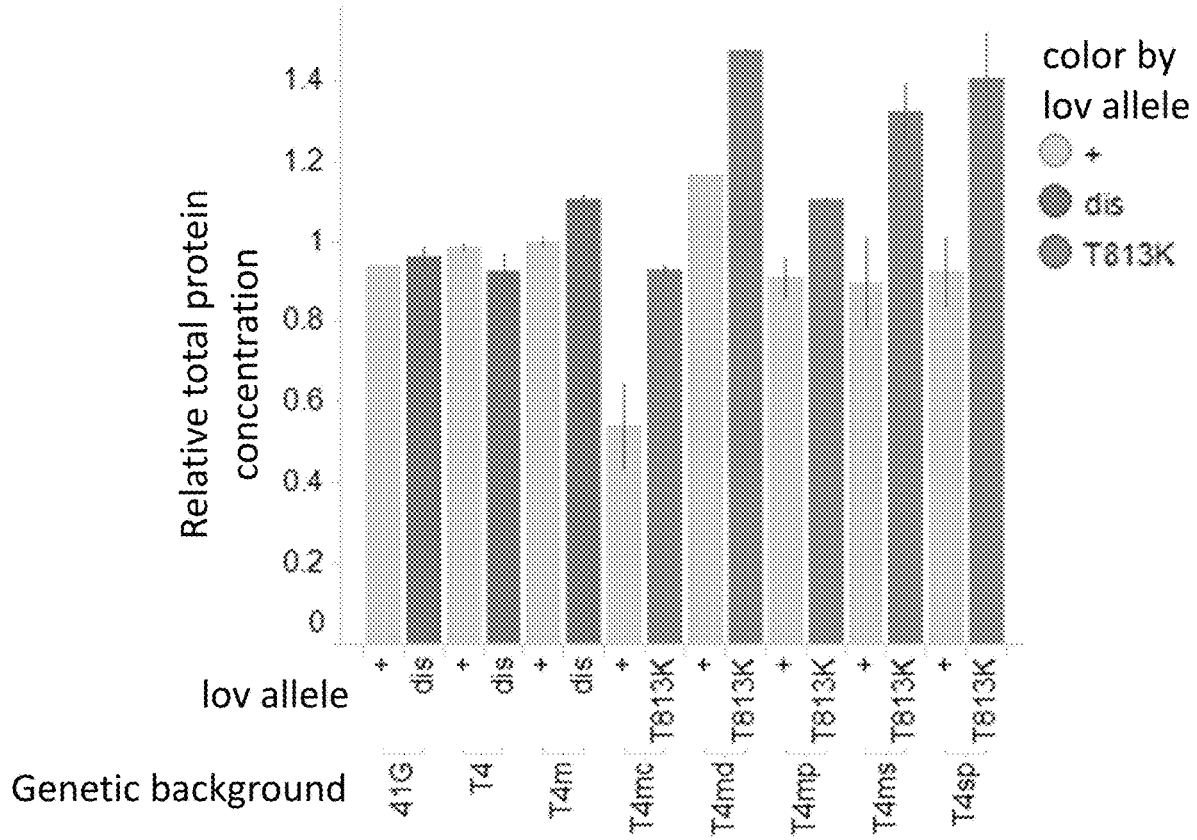
FIG. 5 presents a comparison of relative total protein titer in shake flask fermentations of strains with various marker insertion sites with either the lov(T813K) allele, the lov(dis) allele, or the wild-type lov(+) allele. More particularly, whole cellulase producing strains were evaluated in shake flasks for total protein titer relative to T4 strains and T4m strains run in parallel. Strains of various marker insertion sites were compared in the fermentations with either the wild-type lov(+) allele (FIG. 5, lightest grey bars), the mutant lov(T813K) allele (FIG. 5, medium grey bars), or the lov(dis) allele (FIG. 5, darkest grey bars). Thus, in all marker insertion sites evaluated, the total protein titers increased when the lov(T813K) allele was present. However, insertion of either the pyr4 (FIG. 5, strain "41G") or pyr2 marker (strains T4 and T4m) in the lov gene itself (the lov(dis) allele) showed no significant improvement in relative titers.

As shown in FIG. 5, protein titer increased when the lov(T813K) mutation was present in the T4mc (site C), T4md (site B), T4mp (site A) and T4sp (site A) backgrounds in addition to the T4ms background which was exemplified above in bioreactors (Example 2). On the contrary, genetic backgrounds 41G, T4 and T4m comprising an insertion of the pyr2 marker or pyr4 marker disrupting the lov gene, i.e., allele lov(dis), did not show significant improvement in protein production in shake flasks.

D. Fermentor Evaluation of Strain T4mp with and without the lov(T813K) Allele

Figure 6:
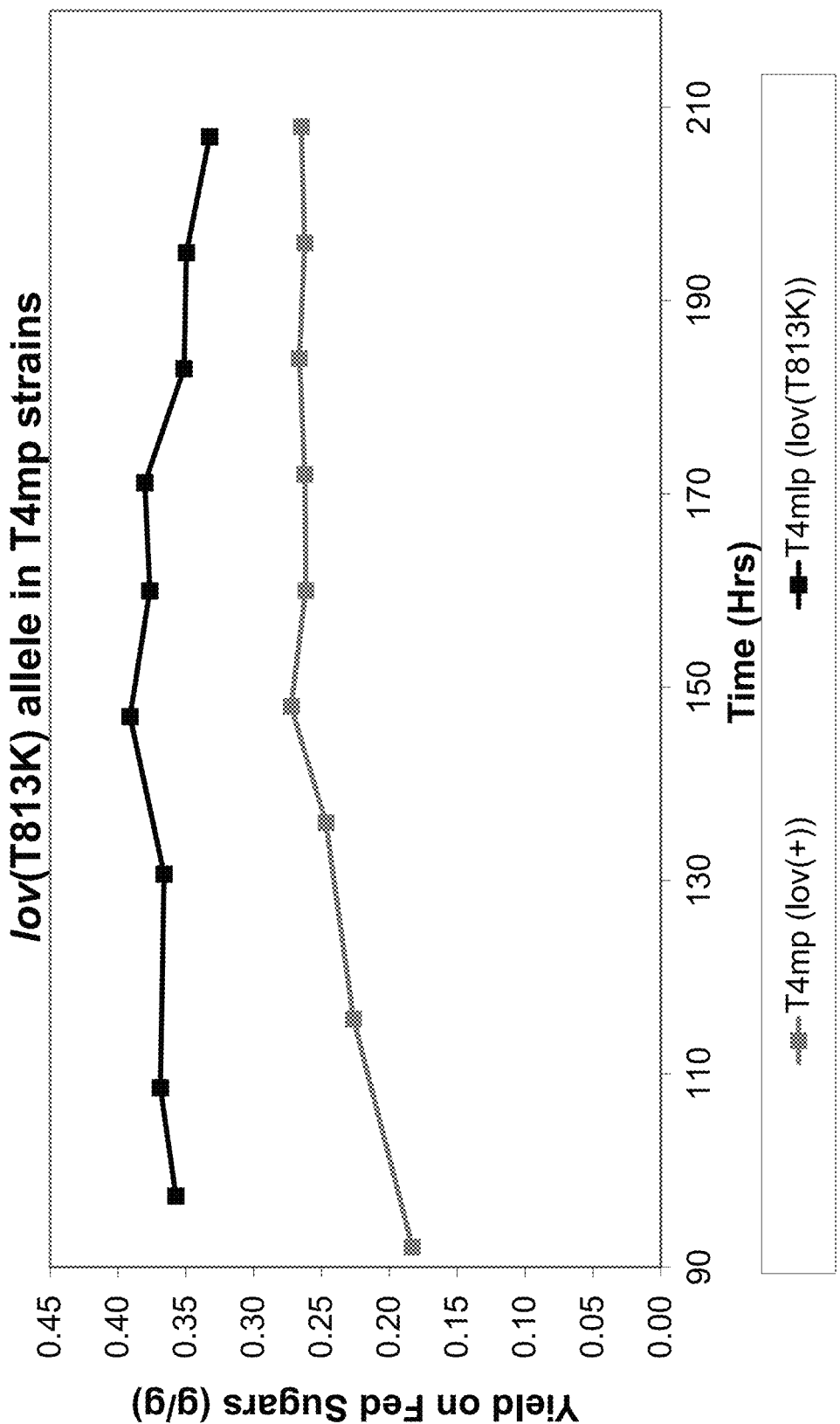
FIG. 6 shows a comparison of total protein yield on fed sugars for the whole cellulase producing T4mp strain (FIG. 6, grey data points/grey line) and lov(T813K) mutant T4mlp strain (FIG. 6, black data points/black line). Thus, these whole cellulase expressing strains were evaluated for protein productivity in fermentors. The figure legend shows the strain name (see TABLE 1 for genotypes) followed by the lov allele in that strain in parenthesis for each line type.

One pair of these strains, T4mp and T4mlp (insertion of pyr2 at site A), was further evaluated in 14 L fermentors as generally described in Example 1, but at lower cell density. As shown in FIG. 6, in the presence of the lov(T813K) allele, this genetic background showed a 28% increase in total protein yield on fed sugars.

---

The invention claimed is:

1. A recombinant *Trichoderma* sp. cell comprising an introduced polynucleotide construct encoding a variant LOV protein comprising at least 99% sequence identity to SEQ ID NO: 4 and a lysine (K) residue at an amino acid position corresponding to position 813 of SEQ ID NO: 4, wherein the recombinant cell comprises an enhanced protein productivity phenotype relative to an isogenic *Trichoderma* sp. control cell which does not comprise the introduced polynucleotide construct, wherein the recombinant and control cells are fermented under the same conditions.

2. The recombinant cell of claim 1, further comprising a polynucleotide encoding a protein of interest (POI).

3. The recombinant cell of claim 1, comprising a polynucleotide construct encoding a NIK1 (M743T) protein of comprising SEQ ID NO: 19.

4. The recombinant cell of claim 1, comprising at least one genetic modification which deletes, disrupts or reduces the expression of a protein selected from the group consisting of SSB7, MPG1 SFB3, SEB1, CRZ1, TSP2 and/or GAS1.

5. A vector comprising a nucleic acid encoding a variant LOV protein comprising at least 99% sequence identity to SEQ ID NO: 4 and a lysine (K) residue at an amino acid position corresponding to position 813 of SEQ ID NO: 4.

6. A method for constructing a recombinant *Trichoderma* sp. cell comprising an enhanced protein productivity phenotype comprising:
   (a) obtaining a parental *Trichoderma* sp. cell producing a protein of interest (POI) and introducing into the cell a polynucleotide construct encoding a LOV variant protein comprising at least 99% identity to SEQ ID NO: 4 and a lysine (K) residue at an amino acid position corresponding to position 813 of SEQ ID NO: 4, and
   (b) isolating the recombinant cell of step (a),
   wherein the recombinant cell comprises an enhanced protein productivity phenotype relative to the parental cell when fermented under the same conditions.

7. The method of claim 6, wherein the parental cell comprises an introduced polynucleotide encoding a NIK1 (M743T) protein comprising SEQ ID NO: 19.

8. The method of claim 6, wherein the parental cell comprises at least one genetic modification which deletes, disrupts or reduces the expression of a protein selected from the group consisting of SSB7, MPG1 SFB3, SEB1, CRZ1, TSP2 and/or GAS 1.

* * * * *

SEQUENCE LISTING

```
<160> NUMBER OF SEQ ID NOS: 24

<210> SEQ ID NO 1
<211> LENGTH: 2765
<212> TYPE: DNA
<213> ORGANISM: Hypocrea jecorina

<400> SEQUENCE: 1
atgggtatcg gaagctactt caaggccagt accaaaaatg ctgagcaggc accgccagcg        60
ccgccgccgg ccaagctggc tcctcctcct cggttacagc tggaaggtcg gcagtcggta       120
atgtcggaga agccaccatc gtccacctcg ggcaacgacg tggatcttca gcctcccacc       180
cctaggtttc attcccgacc ccaatccagc tctggcaggt ctacccttc aacgcagagc        240 tccatgttcc tcgacgacat caagcatgaa gtcatggtca actatctgta ccagcagcag       300
tgttctcagc tctgggtcag cgacgggtct ggggagatcg agggtgtcct gcttcgtaaa       360
gctcgaggcc actacatggc ctgtccccccc cagcttgcca gttctccctt tgcgctggca      420
tgcgctgctc tcaacgtgca gtgcgccatg acagtcaact cgcgtgtcat caagactttt       480
ctgcaatggt cccctgacgc cgttgacgtg ccgctcatga acggcttgcg cgtgcagatt       540
```

-continued

```
ctccctacca ttgatgactt gccgcgagct cgcaagtacc agtttgctgc ctttgtcgcg      600
tctgagggcc tcctggttgt ctgggacgat gatgctcttc atttggtggc acgagccaag      660
gctatcgagt ccgagctcat ggagctggtg tggaaggccg gcaacgtaga cgaggaaggc      720
ggcgacgaga agggaggcca acctgtcact gaggttgaaa ttgatgaaga gagcggagag      780
atcaagcccg agaagcggcc cattcatctc caaaacaccg tcctcgtgtc tctgaccctg      840
gccttggtaa ccgtctctct tggcgccgcc tggagacagt tggccattga ggtttccgtg      900
gacagcaact acatccgtct tgccctcgtc gccctggctc cagtccaggt tttcttcacc      960
ctcttcttcg cccaggtcat tatcggctgc ttggctcaaa tctttggtcc catccgtcag     1020
ctcacaatca actccaagtt ctactctgcc cgaccccac cgcgcctgca gagtgccgtt      1080
cttcctcatg taaccatcca gtgccccgtc tacaaggaag gtctgcaggg tgtcatcatg     1140
ccgacggtca agtccatcaa gcaggccatg tccacgtacg agctccaggg cggttccgca     1200
aacatgttca tcaacgacga tggtttgcag ctcatctccg aagaggatcg tcttgctcgc     1260
atcgagttct acgccgacaa cagcatcggc tgggtcgctc gccccaagca cggagagaac     1320
ggcttcaccc gcaagggcaa gttcaagaag gcctccaaca tgaactttgc cctcatgatc     1380
tcatgcaagg tcgaggagaa gctgcaggca attgagcgtc accccggatg gagccagaat     1440
gacgaggcct ggcgtacgga ggaagctctc aaggaagttc tcgaggccga tggccgtgcc     1500
tgggctgatg gtaacatccg catgggagac tacatcttgc tcatcgactc cgatacccgt     1560
gtccccgccg attgcctgct cgatgctgtt tccgagatgg agcagtcccc cgacgttggc     1620
atcatgcagt tctcctccgg cgtcatgcag gtcgtccaca cgtactttga aacggcatc      1680 accttcttca ccaacctcat ttactctgcc atccgataca ccgtctccaa cggtgacgtc     1740
gcgccctttg tcggccacaa cgccatcctc cgctggtctg ccatccagca ggtcgcctac     1800
caggacgagg acggctacga caagttctgg tcggagagcc acgtctcgga agactttgac     1860
atgtcgctgc gtctgcagtg caacggctac atcatccgcc tggctgcctg ggctggagag     1920
ggtttcaagg agggcgtgtc gctgaccgtc tacgacgagc ttgcccggtg gaaaaagtac     1980
gcctacggct gcaacgagct cctgttccac cccattcgca cctggctctg gcgcggtccc     2040
tttacgccct tgttccgccg cttcctcttc tccaacattc gctttacgtc caaggtcacc     2100
gtcatctcct acatcggtac ctactacgcc atcggcgctg cctggatctt gaccgcggtc     2160
aactacttcg tcatgggctg gttcaacggc tacctggata agtactacgt cgactcgtgg     2220
caggtctggt tctccatcat catcgtcttc aacggcctcg gcaacattgc cctagccgtc     2280
atgcggtacc gcgtcggcga gcgcggtctg ctgtacgccc tgtttgagaa ctttatgtgg     2340
actctcatgc tggccatatt cctcggcggc ctgtcactgc acgtcagcca ggctctgctg     2400
gcgcacatgt ttgagattaa catgacatgg ggcgccacaa gcaaggaggc cgagtttttcc    2460 aacttttttca tcgaggtgcc aaaggtcttg aagaaggtta gtcaccctcg tttcattcat    2520
ccatccatct taccatgctg cgcgaagact tcagtttgct gacaattctg ttgtagttca     2580
aattctccat gctcttctcg ttgatcttca tcgccggcat gattatcctc gcccaggcgc     2640
cctttgtccc ctttgattgg cgcatcaagg actttgtcgc catcctgcct atggccaccg     2700
tcgccgccag ccacttcctg ctgcccctgg ccctgaaccc tgccctcatg acgttctcat     2760
ggtaa                                                                 2765
```

<210> SEQ ID NO 2

```
<211> LENGTH: 894
<212> TYPE: PRT
<213> ORGANISM: Hypocrea jecorina

<400> SEQUENCE: 2

Met Gly Ile Gly Ser Tyr Phe Lys Ala Ser Thr Lys Asn Ala Glu Gln
1               5                   10                  15

Ala Pro Ala Pro Pro Ala Lys Leu Ala Pro Pro Arg Leu
            20                  25                  30

Gln Leu Glu Gly Arg Gln Ser Val Met Ser Glu Lys Pro Pro Ser Ser
            35                  40                  45

Thr Ser Gly Asn Asp Val Asp Leu Gln Pro Pro Thr Pro Arg Phe His
        50                  55                  60

Ser Arg Pro Gln Ser Ser Ser Gly Arg Ser Thr Pro Ser Thr Gln Ser
65                  70                  75                  80

Ser Met Phe Leu Asp Asp Ile Lys His Glu Val Met Val Asn Tyr Leu
                85                  90                  95

Tyr Gln Gln Gln Cys Ser Gln Leu Trp Val Ser Asp Gly Ser Gly Glu
            100                 105                 110

Ile Glu Gly Val Leu Leu Arg Lys Ala Arg Gly His Tyr Met Ala Cys
        115                 120                 125

Pro Pro Gln Leu Ala Ser Ser Pro Phe Ala Leu Ala Cys Ala Ala Leu
    130                 135                 140

Asn Val Gln Cys Ala Met Thr Val Asn Ser Arg Val Ile Lys Thr Phe
145                 150                 155                 160

Leu Gln Trp Ser Pro Asp Ala Val Asp Val Pro Leu Met Asn Gly Leu
                165                 170                 175

Arg Val Gln Ile Leu Pro Thr Ile Asp Asp Leu Pro Arg Ala Arg Lys
            180                 185                 190

Tyr Gln Phe Ala Ala Phe Val Ala Ser Glu Gly Leu Leu Val Val Trp
        195                 200                 205

Asp Asp Asp Ala Leu His Leu Val Ala Arg Ala Lys Ala Ile Glu Ser
    210                 215                 220

Glu Leu Met Glu Leu Val Trp Lys Ala Gly Asn Val Asp Glu Glu Gly
225                 230                 235                 240

Gly Asp Glu Lys Gly Gly Gln Pro Val Thr Glu Val Glu Ile Asp Glu
                245                 250                 255

Glu Ser Gly Glu Ile Lys Pro Glu Lys Arg Pro Ile His Leu Gln Asn
            260                 265                 270

Thr Val Leu Val Ser Leu Thr Leu Ala Leu Val Thr Val Ser Leu Gly
        275                 280                 285

Ala Ala Trp Arg Gln Leu Ala Ile Glu Val Ser Val Asp Ser Asn Tyr
    290                 295                 300

Ile Arg Leu Ala Leu Val Ala Leu Ala Pro Val Gln Val Phe Thr
305                 310                 315                 320

Leu Phe Phe Ala Gln Val Ile Ile Gly Cys Leu Ala Gln Ile Phe Gly
                325                 330                 335

Pro Ile Arg Gln Leu Thr Ile Asn Ser Lys Phe Tyr Ser Ala Arg Pro
            340                 345                 350

Pro Pro Arg Leu Gln Ser Ala Val Leu Pro His Val Thr Ile Gln Cys
        355                 360                 365

Pro Val Tyr Lys Glu Gly Leu Gln Gly Val Ile Met Pro Thr Val Lys
    370                 375                 380
```

-continued

Ser Ile Lys Gln Ala Met Ser Thr Tyr Glu Leu Gln Gly Gly Ser Ala
385                 390                 395                 400

Asn Met Phe Ile Asn Asp Asp Gly Leu Gln Leu Ile Ser Glu Glu Asp
        405                 410                 415

Arg Leu Ala Arg Ile Glu Phe Tyr Ala Asp Asn Ser Ile Gly Trp Val
            420                 425                 430

Ala Arg Pro Lys His Gly Glu Asn Gly Phe Thr Arg Lys Gly Lys Phe
                435                 440                 445

Lys Lys Ala Ser Asn Met Asn Phe Ala Leu Met Ile Ser Cys Lys Val
            450                 455                 460

Glu Glu Lys Leu Gln Ala Ile Glu Arg His Pro Gly Trp Ser Gln Asn
465                 470                 475                 480

Asp Glu Ala Leu Ala Tyr Glu Glu Ala Leu Lys Glu Val Leu Glu Ala
                485                 490                 495

Asp Gly Arg Ala Trp Ala Asp Gly Asn Ile Arg Met Gly Asp Tyr Ile
            500                 505                 510

Leu Leu Ile Asp Ser Asp Thr Arg Val Pro Ala Asp Cys Leu Leu Asp
        515                 520                 525

Ala Val Ser Glu Met Glu Gln Ser Pro Asp Val Gly Ile Met Gln Phe
530                 535                 540

Ser Ser Gly Val Met Gln Val His Thr Tyr Phe Glu Asn Gly Ile
545                 550                 555                 560

Thr Phe Phe Thr Asn Leu Ile Tyr Ser Ala Ile Arg Tyr Thr Val Ser
            565                 570                 575

Asn Gly Asp Val Ala Pro Phe Val Gly His Asn Ala Ile Leu Arg Trp
        580                 585                 590

Ser Ala Ile Gln Gln Val Ala Tyr Gln Asp Glu Asp Gly Tyr Asp Lys
    595                 600                 605

Phe Trp Ser Glu Ser His Val Ser Glu Asp Phe Asp Met Ser Leu Arg
    610                 615                 620

Leu Gln Cys Asn Gly Tyr Ile Ile Arg Leu Ala Ala Trp Ala Gly Glu
625                 630                 635                 640

Gly Phe Lys Glu Gly Val Ser Leu Thr Val Tyr Asp Glu Leu Ala Arg
                645                 650                 655

Trp Glu Lys Tyr Ala Tyr Gly Cys Asn Glu Leu Leu Phe His Pro Ile
                660                 665                 670

Arg Thr Trp Leu Trp Arg Gly Pro Phe Thr Pro Leu Phe Arg Arg Phe
            675                 680                 685

Leu Phe Ser Asn Ile Arg Phe Thr Ser Lys Val Thr Val Ile Ser Tyr
        690                 695                 700

Ile Gly Thr Tyr Tyr Ala Ile Gly Ala Ala Trp Ile Leu Thr Ala Val
705                 710                 715                 720

Asn Tyr Phe Val Met Gly Trp Phe Asn Gly Tyr Leu Asp Lys Tyr Tyr
                725                 730                 735

Val Asp Ser Trp Gln Val Trp Phe Ser Ile Ile Val Phe Asn Gly
            740                 745                 750

Leu Gly Asn Ile Ala Leu Ala Val Met Arg Tyr Arg Val Gly Glu Arg
        755                 760                 765

Gly Leu Leu Tyr Ala Leu Phe Glu Asn Phe Met Trp Thr Leu Met Leu
    770                 775                 780

Ala Ile Phe Leu Gly Gly Leu Ser Leu His Val Ser Gln Ala Leu Leu
785                 790                 795                 800

```
Ala His Met Phe Glu Ile Asn Met Thr Trp Gly Ala Thr Ser Lys Glu
                805                 810                 815

Ala Glu Phe Ser Asn Phe Phe Ile Glu Val Pro Lys Val Leu Lys Lys
            820                 825                 830

Phe Lys Phe Ser Met Leu Phe Ser Leu Ile Phe Ile Ala Gly Met Ile
        835                 840                 845

Ile Leu Ala Gln Ala Pro Phe Val Pro Phe Asp Trp Arg Ile Lys Asp
    850                 855                 860

Phe Val Ala Ile Leu Pro Met Ala Thr Val Ala Ala Ser His Phe Leu
865                 870                 875                 880

Leu Pro Leu Ala Leu Asn Pro Ala Leu Met Thr Phe Ser Trp
                885                 890

<210> SEQ ID NO 3
<211> LENGTH: 2765
<212> TYPE: DNA
<213> ORGANISM: Hypocrea jecorina

<400> SEQUENCE: 3
atgggtatcg gaagctactt caaggccagt accaaaaatg ctgagcaggc accgccagcg      60
ccgccgccgg ccaagctggc tcctcctcct cggttacagc tggaaggtcg gcagtcggta     120
atgtcggaga agccaccatc gtccacctcg gcaacgacg tggatcttca gcctcccacc      180
cctaggtttc attcccgacc ccaatccagc tctggcaggt ctaccccttc aacgcagagc     240
tccatgttcc tcgacgacat caagcatgaa gtcatggtca actatctgta ccagcagcag     300
tgttctcagc tctgggtcag cgacgggtct ggggagatcg agggtgtcct gcttcgtaaa     360
gctcgaggcc actacatggc ctgtccccc cagcttgcca gttctcccttt gcgctggca    420 tgcgctgctc tcaacgtgca gtgcgccatg acagtcaact cgcgtgtcat caagacgttt     480
ctgcaatggt cccctgacgc cgttgacgtg ccgctcatga acggcttgcg cgtgcagatt     540
ctccctacca ttgatgactt gccgcgagct cgcaagtacc agtttgctgc ctttgtcgcg     600
tctgagggcc tcctggttgt ctgggacgat gatgctcttc atttggtggc acgagccaag     660
gctatcgagt ccgagctcat ggagctggtg tggaaggccg gcaacgtaga cgaggaaggc     720
ggcgacgaga agggaggcca acctgtcact gaggttgaaa ttgatgaaga gagcggagag     780
atcaagcccg agaagcggcc cattcatctc caaaacaccg tcctcgtgtc tctgaccctg     840
gccttggtaa ccgtctctct ggcgccgcc tggagacagt tggccattga ggtttccgtg      900
gacagcaact acatccgtct tgccctcgtc gccctggctc cagtccaggt tttcttcacc     960
ctcttcttcg cccaggtcat tatcggctgc ttggctcaaa tctttggtcc catccgtcag    1020
ctcacaatca actccaagtt ctactctgcc cgaccccac cgcgcctgca gagtgccgtt     1080
cttcctcatg taaccatcca gtgccccgtc tacaaggaag gtctgcaggg tgtcatcatg    1140
ccgacggtca gtccatcaa gcaggccatg tccacgtacg agctccaggg cggttccgca    1200
aacatgttca tcaacgacga tggtttgcag ctcatctccg aagaggatcg tcttgctcgc    1260
atcgagttct acgccgacaa cagcatcggc tgggtcgctc gccccaagca cggagagaac    1320
ggcttcaccc gcaagggcaa gttcaagaag gcctccaaca tgaactttgc cctcatgatc    1380
tcatgcaagg tcgaggagaa gctgcaggca attgagcgtc accccggatg gagccagaat    1440
gacgaggcct ggcgtacga ggaagctctc aaggaagttc tcgaggccga tggccgtgcc     1500
tgggctgatg gtaacatccg catgggagac tacatcttgc tcatcgactc cgataccccgt    1560 gtccccgccg attgcctgct cgatgctgtt tccgagatgg agcagtcccc cgacgttggc    1620
```

-continued

```
atcatgcagt tctcctccgg cgtcatgcag gtcgtccaca cgtactttga gaacggcatc    1680
accttcttca ccaacctcat ttactctgcc atccgataca ccgtctccaa cggtgacgtc    1740 gcgcccttg tcggccacaa cgccatcctc cgctggtctg ccatccagca ggtcgcctac     1800
caggacgagg acggctacga caagttctgg tcggagagcc acgtctcgga agactttgac    1860
atgtcgctgc gtctgcagtg caacggctac atcatccgcc tggctgcctg ggctggagag    1920
ggtttcaagg agggcgtgtc gctgaccgtc tacgacgagc ttgcccggtg ggaaaagtac    1980
gcctacggct gcaacgagct cctgttccac cccattcgca cctggctctg cgcggtccc    2040 tttacgcccct tgttccgccg cttcctcttc tccaacattc gctttacgtc caaggtcacc   2100
gtcatctcct acatcggtac ctactacgcc atcggcgctg cctggatctt gaccgcggtc    2160
aactacttcg tcatgggctg gttcaacggc tacctggata gtactacgt cgactcgtgg    2220 caggtctggt tctccatcat catcgtcttc aacggcctcg gcaacattgc cctagccgtc    2280
atgcggtacc gcgtcggcga gcgcggtctg ctgtacgccc tgtttgagaa ctttatgtgg    2340
actctcatgc tggccatatt cctcggcggc ctgtcactgc acgtcagcca ggctctgctg    2400
gcgcacatgt ttgagattaa catgacatgg ggcgccaaaa gcaaggaggc cgagttttcc    2460 aacttttca tcgaggtgcc aaaggtcttg aagaaggtta gtcaccctcg tttcattcat     2520
ccatccatct taccatgctg cgcgaagact tcagtttgct gacaattctg ttgtagttca    2580
aattctccat gctcttctcg ttgatcttca tcgccggcat gattatcctc gcccaggcgc    2640
cctttgtccc ctttgattgg cgcatcaagg actttgtcgc catcctgcct atggccaccg    2700
tcgccgccag ccacttcctg ctgccccctgg ccctgaaccc tgccctcatg acgttctcat   2760
ggtaa                                                                2765
```

<210> SEQ ID NO 4
<211> LENGTH: 894
<212> TYPE: PRT
<213> ORGANISM: Hypocrea jecorina

<400> SEQUENCE: 4

```
Met Gly Ile Gly Ser Tyr Phe Lys Ala Ser Thr Lys Asn Ala Glu Gln
1               5                   10                  15

Ala Pro Ala Pro Pro Ala Lys Leu Ala Pro Pro Arg Leu
            20                  25                  30

Gln Leu Glu Gly Arg Gln Ser Val Met Ser Glu Lys Pro Pro Ser Ser
            35                  40                  45

Thr Ser Gly Asn Asp Val Asp Leu Gln Pro Thr Pro Arg Phe His
        50                  55                  60

Ser Arg Pro Gln Ser Ser Gly Arg Ser Thr Pro Ser Thr Gln Ser
65              70                  75                  80

Ser Met Phe Leu Asp Asp Ile Lys His Glu Val Met Asn Tyr Leu
            85                  90                  95

Tyr Gln Gln Gln Cys Ser Gln Leu Trp Val Ser Asp Gly Ser Gly Glu
            100                 105                 110

Ile Glu Gly Val Leu Leu Arg Lys Ala Arg Gly His Tyr Met Ala Cys
            115                 120                 125

Pro Pro Gln Leu Ala Ser Ser Pro Phe Ala Leu Ala Cys Ala Ala Leu
            130                 135                 140

Asn Val Gln Cys Ala Met Thr Val Asn Ser Arg Val Ile Lys Thr Phe
145             150                 155                 160
```

```
Leu Gln Trp Ser Pro Asp Ala Val Asp Val Pro Leu Met Asn Gly Leu
                165                 170                 175
Arg Val Gln Ile Leu Pro Thr Ile Asp Asp Leu Pro Arg Ala Arg Lys
            180                 185                 190
Tyr Gln Phe Ala Ala Phe Val Ala Ser Glu Gly Leu Leu Val Val Trp
        195                 200                 205
Asp Asp Asp Ala Leu His Leu Val Ala Arg Ala Lys Ala Ile Glu Ser
    210                 215                 220
Glu Leu Met Glu Leu Val Trp Lys Ala Gly Asn Val Asp Glu Glu Gly
225                 230                 235                 240
Gly Asp Glu Lys Gly Gly Gln Pro Val Thr Glu Val Glu Ile Asp Glu
                245                 250                 255
Glu Ser Gly Glu Ile Lys Pro Glu Lys Arg Pro Ile His Leu Gln Asn
            260                 265                 270
Thr Val Leu Val Ser Leu Thr Leu Ala Leu Val Thr Val Ser Leu Gly
        275                 280                 285
Ala Ala Trp Arg Gln Leu Ala Ile Glu Val Ser Val Asp Ser Asn Tyr
    290                 295                 300
Ile Arg Leu Ala Leu Val Ala Leu Ala Pro Val Gln Val Phe Phe Thr
305                 310                 315                 320
Leu Phe Phe Ala Gln Val Ile Ile Gly Cys Leu Ala Gln Ile Phe Gly
                325                 330                 335
Pro Ile Arg Gln Leu Thr Ile Asn Ser Lys Phe Tyr Ser Ala Arg Pro
            340                 345                 350
Pro Pro Arg Leu Gln Ser Ala Val Leu Pro His Val Thr Ile Gln Cys
        355                 360                 365
Pro Val Tyr Lys Glu Gly Leu Gln Gly Val Ile Met Pro Thr Val Lys
    370                 375                 380
Ser Ile Lys Gln Ala Met Ser Thr Tyr Glu Leu Gln Gly Gly Ser Ala
385                 390                 395                 400
Asn Met Phe Ile Asn Asp Asp Gly Leu Gln Leu Ile Ser Glu Glu Asp
                405                 410                 415
Arg Leu Ala Arg Ile Glu Phe Tyr Ala Asp Asn Ser Ile Gly Trp Val
            420                 425                 430
Ala Arg Pro Lys His Gly Glu Asn Gly Phe Thr Arg Lys Gly Lys Phe
        435                 440                 445
Lys Lys Ala Ser Asn Met Asn Phe Ala Leu Met Ile Ser Cys Lys Val
    450                 455                 460
Glu Glu Lys Leu Gln Ala Ile Glu Arg His Pro Gly Trp Ser Gln Asn
465                 470                 475                 480
Asp Glu Ala Leu Ala Tyr Glu Glu Ala Leu Lys Glu Val Leu Glu Ala
                485                 490                 495
Asp Gly Arg Ala Trp Ala Asp Gly Asn Ile Arg Met Gly Asp Tyr Ile
            500                 505                 510
Leu Leu Ile Asp Ser Asp Thr Arg Val Pro Ala Asp Cys Leu Leu Asp
        515                 520                 525
Ala Val Ser Glu Met Glu Gln Ser Pro Asp Val Gly Ile Met Gln Phe
    530                 535                 540
Ser Ser Gly Val Met Gln Val Val His Thr Tyr Phe Glu Asn Gly Ile
545                 550                 555                 560
Thr Phe Phe Thr Asn Leu Ile Tyr Ser Ala Ile Arg Tyr Thr Val Ser
                565                 570                 575
```

```
Asn Gly Asp Val Ala Pro Phe Val Gly His Asn Ala Ile Leu Arg Trp
            580                 585                 590

Ser Ala Ile Gln Gln Val Ala Tyr Gln Asp Glu Asp Gly Tyr Asp Lys
        595                 600                 605

Phe Trp Ser Glu Ser His Val Ser Glu Asp Phe Asp Met Ser Leu Arg
    610                 615                 620

Leu Gln Cys Asn Gly Tyr Ile Ile Arg Leu Ala Ala Trp Ala Gly Glu
625                 630                 635                 640

Gly Phe Lys Glu Gly Val Ser Leu Thr Val Tyr Asp Glu Leu Ala Arg
                645                 650                 655

Trp Glu Lys Tyr Ala Tyr Gly Cys Asn Glu Leu Leu Phe His Pro Ile
            660                 665                 670

Arg Thr Trp Leu Trp Arg Gly Pro Phe Thr Pro Leu Phe Arg Arg Phe
        675                 680                 685

Leu Phe Ser Asn Ile Arg Phe Thr Ser Lys Val Thr Val Ile Ser Tyr
690                 695                 700

Ile Gly Thr Tyr Tyr Ala Ile Gly Ala Ala Trp Ile Leu Thr Ala Val
705                 710                 715                 720

Asn Tyr Phe Val Met Gly Trp Phe Asn Gly Tyr Leu Asp Lys Tyr Tyr
                725                 730                 735

Val Asp Ser Trp Gln Val Trp Phe Ser Ile Ile Val Phe Asn Gly
            740                 745                 750

Leu Gly Asn Ile Ala Leu Ala Val Met Arg Tyr Arg Val Gly Glu Arg
                755                 760                 765

Gly Leu Leu Tyr Ala Leu Phe Glu Asn Phe Met Trp Thr Leu Met Leu
    770                 775                 780

Ala Ile Phe Leu Gly Gly Leu Ser Leu His Val Ser Gln Ala Leu Leu
785                 790                 795                 800

Ala His Met Phe Glu Ile Asn Met Thr Trp Gly Ala Lys Ser Lys Glu
                805                 810                 815

Ala Glu Phe Ser Asn Phe Phe Ile Glu Val Pro Lys Val Leu Lys Lys
                820                 825                 830

Phe Lys Phe Ser Met Leu Phe Ser Leu Ile Phe Ile Ala Gly Met Ile
    835                 840                 845

Ile Leu Ala Gln Ala Pro Phe Val Pro Phe Asp Trp Arg Ile Lys Asp
850                 855                 860

Phe Val Ala Ile Leu Pro Met Ala Thr Val Ala Ala Ser His Phe Leu
865                 870                 875                 880

Leu Pro Leu Ala Leu Asn Pro Ala Leu Met Thr Phe Ser Trp
                885                 890

<210> SEQ ID NO 5
<211> LENGTH: 364
<212> TYPE: PRT
<213> ORGANISM: Hypocrea jecorina

<400> SEQUENCE: 5

Met Lys Gly Leu Ile Leu Val Gly Gly Phe Gly Thr Arg Leu Arg Pro
1               5                   10                  15

Leu Thr Leu Thr Leu Pro Lys Pro Leu Val Glu Phe Cys Asn Lys Pro
            20                  25                  30

Met Ile Val His Gln Ile Glu Ala Leu Val Ala Ala Gly Val Thr Asp
        35                  40                  45
```

```
Ile Val Leu Ala Val Asn Tyr Arg Pro Glu Ile Met Glu Lys Phe Leu
    50                  55                  60
Ala Glu Tyr Glu Glu Lys Tyr Asn Ile Asn Ile Glu Phe Ser Val Glu
65                  70                  75                  80
Ser Glu Pro Leu Asp Thr Ala Gly Pro Leu Lys Leu Ala Glu Arg Ile
                85                  90                  95
Leu Gly Lys Asp Asp Ser Pro Phe Phe Val Leu Asn Ser Asp Val Ile
            100                 105                 110
Cys Asp Tyr Pro Phe Lys Glu Leu Glu Phe His Lys Ala His Gly
            115                 120                 125
Asp Glu Gly Thr Ile Val Val Thr Lys Val Glu Pro Ser Lys Tyr
    130                 135                 140
Gly Val Val His Lys Pro Asn His Pro Ser Arg Ile Asp Arg Phe
145                 150                 155                 160
Val Glu Lys Pro Val Glu Phe Val Gly Asn Arg Ile Asn Ala Gly Met
                165                 170                 175
Tyr Ile Phe Asn Pro Ser Val Leu Lys Arg Ile Glu Leu Arg Pro Thr
            180                 185                 190
Ser Ile Glu Lys Glu Thr Phe Pro Ala Met Val Ala Asp Asn Gln Leu
        195                 200                 205
His Ser Phe Asp Leu Glu Gly Phe Trp Met Asp Val Gly Gln Pro Lys
    210                 215                 220
Asp Phe Leu Ser Gly Thr Cys Leu Tyr Leu Ser Ser Leu Thr Lys Lys
225                 230                 235                 240
Gly Ser Lys Glu Leu Thr Pro Pro Thr Glu Pro Tyr Val His Gly Gly
                245                 250                 255
Asn Val Met Ile His Pro Ser Ala Lys Ile Gly Lys Asn Cys Arg Ile
            260                 265                 270
Gly Pro Asn Val Thr Ile Gly Pro Asp Val Val Gly Asp Gly Val
        275                 280                 285
Arg Leu Gln Arg Cys Val Leu Leu Lys Gly Ser Lys Val Lys Asp His
    290                 295                 300
Ala Trp Val Lys Ser Thr Ile Val Gly Trp Asn Ser Thr Val Gly Arg
305                 310                 315                 320
Trp Ala Arg Leu Glu Asn Val Thr Val Leu Gly Asp Asp Val Thr Ile
                325                 330                 335
Gly Asp Glu Ile Tyr Val Asn Gly Gly Ser Val Leu Pro His Lys Ser
            340                 345                 350
Ile Lys Ala Asn Val Asp Val Pro Ala Ile Ile Met
        355                 360

<210> SEQ ID NO 6
<211> LENGTH: 534
<212> TYPE: PRT
<213> ORGANISM: Hypocrea jecorina

<400> SEQUENCE: 6

Met Asp Gly Met Met Ser Gln Pro Met Gly Gln Gln Ala Phe Tyr Phe
1               5                   10                  15
Tyr Asn His Glu His Lys Met Ser Pro Arg Gln Val Ile Phe Ala Gln
            20                  25                  30
Gln Met Ala Ala Tyr Gln Met Met Pro Ser Leu Pro Thr Pro Met
        35                  40                  45
```

```
Tyr Ser Arg Pro Asn Ser Ser Cys Ser Gln Pro Thr Leu Tyr Ser
     50              55              60

Asn Gly Pro Ser Val Met Thr Pro Thr Ser Thr Pro Pro Leu Ser Ser
65               70              75              80

Arg Lys Pro Met Leu Val Asp Thr Glu Phe Gly Asp Asn Pro Tyr Phe
                 85              90              95

Pro Ser Thr Pro Pro Leu Ser Ala Ser Gly Ser Thr Val Gly Ser Pro
            100             105             110

Lys Ala Cys Asp Met Leu Gln Thr Pro Met Asn Pro Met Phe Ser Gly
        115             120             125

Leu Glu Gly Ile Ala Ile Lys Asp Ser Ile Asp Ala Thr Glu Ser Leu
    130             135             140

Val Leu Asp Trp Ala Ser Ile Ala Ser Pro Pro Leu Ser Pro Val Tyr
145             150             155             160

Leu Gln Ser Gln Thr Ser Ser Gly Lys Val Pro Ser Leu Thr Ser Ser
                165             170             175

Pro Ser Asp Met Leu Ser Thr Thr Ala Ser Cys Pro Ser Leu Ser Pro
            180             185             190

Ser Pro Thr Pro Tyr Ala Arg Ser Val Thr Ser Glu His Asp Val Asp
        195             200             205

Phe Cys Asp Pro Arg Asn Leu Thr Val Ser Val Gly Ser Asn Pro Thr
210             215             220

Leu Ala Pro Glu Phe Thr Leu Leu Ala Asp Asp Ile Lys Gly Glu Pro
225             230             235             240

Leu Pro Thr Ala Ala Gln Pro Ser Phe Asp Phe Asn Pro Ala Leu Pro
                245             250             255

Ser Gly Leu Pro Thr Phe Glu Asp Phe Ser Asp Leu Glu Ser Glu Ala
            260             265             270

Asp Phe Ser Ser Leu Val Asn Leu Gly Glu Ile Asn Pro Val Asp Ile
        275             280             285

Ser Arg Pro Arg Ala Cys Thr Gly Ser Ser Val Val Ser Leu Gly His
290             295             300

Gly Ser Phe Ile Gly Asp Glu Asp Leu Ser Phe Asp Asp Glu Ala Phe
305             310             315             320

His Phe Pro Ser Leu Pro Ser Pro Thr Ser Ser Val Asp Phe Cys Asp
                325             330             335

Val His Gln Asp Lys Arg Gln Lys Asp Arg Lys Glu Ala Lys Pro
            340             345             350

Val Met Asn Ser Ala Ala Gly Gly Ser Gln Ser Gly Asn Glu Gln Ala
        355             360             365

Gly Ala Thr Glu Ala Ala Ser Ala Ala Ser Asp Ser Asn Ala Ser Ser
    370             375             380

Ala Ser Asp Glu Pro Ser Ser Met Pro Ala Pro Thr Asn Arg Arg
385             390             395             400

Gly Arg Lys Gln Ser Leu Thr Glu Asp Pro Ser Lys Thr Phe Val Cys
                405             410             415

Asp Leu Cys Asn Arg Arg Phe Arg Arg Gln Glu His Leu Lys Arg His
            420             425             430

Tyr Arg Ser Leu His Thr Gln Glu Lys Pro Phe Glu Cys Asn Glu Cys
        435             440             445

Gly Lys Lys Phe Ser Arg Ser Asp Asn Leu Ala Gln His Ala Arg Thr
450             455             460
```

His Ser Gly Gly Ala Ile Val Met Asn Leu Ile Glu Glu Ser Ser Glu
465                 470                 475                 480

Val Pro Ala Tyr Asp Gly Ser Met Met Ala Gly Pro Val Gly Asp Asp
            485                 490                 495

Tyr Ser Thr Tyr Gly Lys Val Leu Phe Gln Ile Ala Ser Glu Ile Pro
        500                 505                 510

Gly Ser Ala Ser Glu Leu Ser Ser Glu Glu Gly Glu Gln Gly Lys Lys
    515                 520                 525

Lys Arg Lys Arg Ser Asp
        530

<210> SEQ ID NO 7
<211> LENGTH: 1042
<212> TYPE: PRT
<213> ORGANISM: Hypocrea jecorina

<400> SEQUENCE: 7

Met Asp Tyr Thr Gln Tyr His Ala Leu Gly His Gly Glu Val Leu Asp
1               5                   10                  15

Pro Asn Asp Pro Asn Lys Thr Ser Ala Pro Ala Ala Pro Gln Phe Gln
            20                  25                  30

Pro Pro Ser Ser Pro Tyr Val Pro Gly Ser Pro Tyr Gly Ala Pro
        35                  40                  45

Pro Tyr His Gly His Gln Ala Pro Met Ala Met Pro Pro
    50                  55                  60

Ser Thr Pro Gly Tyr Gly Pro Pro Gln Gly Gln Ser Phe Pro Gly Ser
65                  70                  75                  80

Pro Met Pro Ser Gln Asp Ala Gly Leu Ala Ala Gln Phe Gly Gly Met
                85                  90                  95

Ser Leu Gly Ala Asp Ala Gly Ala Ala Ala Arg Lys Lys Lys Lys
            100                 105                 110

Asp Arg His Ala Tyr His Ser Val Glu Pro Thr Gly Ser Ser Gln Ala
        115                 120                 125

Phe Asn Gly Leu Pro Pro Gly Thr Pro Ala Glu Gln Phe Leu Asn Val
    130                 135                 140

Asn Asn Pro Gln Gly Ile Pro Ala Leu Gly Gly Gln Phe Gly Ser Pro
145                 150                 155                 160

Leu Ala Ser Pro Met Gly Thr Pro His Met Ala Asn Pro Gly Gln Phe
                165                 170                 175

Pro Ala Pro Thr Ser Pro Phe Thr Pro Ser Ala Pro Val Ser Pro Ala
            180                 185                 190

Glu Phe Ala Ser Arg Phe Gly Ser Pro Asp Ala Ala Thr Ser Ile Gly
        195                 200                 205

Ser Ala Gly Pro Ser Gln Val Ser Pro Asp Asp Met Pro Ser Ile Pro
    210                 215                 220

Ala Ser Arg Asp Ala Ile Gln Glu His Phe Phe Lys Asn Val Tyr Pro
225                 230                 235                 240

Thr Phe Glu Arg His Val Pro Pro Ala Thr Val Ser Phe Val Ala
                245                 250                 255

Phe Asp Gln Gly Asn Ala Ser Pro Lys Phe Thr Arg Leu Thr Leu Asn
            260                 265                 270

Asn Ile Pro Thr Thr Ala Glu Gly Leu His Ala Thr Gly Leu Pro Leu
        275                 280                 285

Gly Met Leu Ile Gln Pro Leu Ala Pro Leu Gln Ala Gly Glu Ala Glu
    290                 295                 300

-continued

```
Ile Pro Val Leu Asp Phe Gly Asp Ala Gly Pro Pro Arg Cys Arg Arg
305                 310                 315                 320

Cys Arg Ala Tyr Ile Asn Pro Phe Met Met Phe Arg Ser Gly Gly Asn
                325                 330                 335

Lys Phe Val Cys Asn Leu Cys Ser Tyr Pro Asn Glu Thr Pro Pro Glu
                340                 345                 350

Tyr Phe Cys Ala Val Ser Pro Gln Gly Val Arg Leu Asp Arg Asp Gln
                355                 360                 365

Arg Pro Glu Leu His Arg Gly Thr Val Glu Phe Val Val Pro Lys Glu
                370                 375                 380

Tyr Trp Thr Arg Glu Pro Val Gly Leu Arg Trp Leu Phe Val Ile Asp
385                 390                 395                 400

Val Thr Gln Glu Ser Tyr Asn Lys Gly Phe Met Glu Thr Phe Cys Glu
                405                 410                 415

Gly Ile Leu Ala Ala Leu Tyr Gly Gly Asn Asp Glu Glu Asn Asp Glu
                420                 425                 430

Asp Gly Glu Pro Lys Arg Arg Ile Pro Lys Gly Ala Lys Val Gly Phe
                435                 440                 445

Ile Thr Tyr Asp Lys Asp Ile His Phe Tyr Asn Ile Asn Pro His Leu
                450                 455                 460

Asp Gln Ala His Met Met Ile Met Pro Asp Leu Glu Asp Pro Phe Leu
465                 470                 475                 480

Pro Leu Gly Glu Gly Leu Phe Val Asp Pro Tyr Glu Ser Lys Ala Ile
                485                 490                 495

Ile Thr Ser Leu Leu Thr Arg Leu Pro Glu Met Phe Ser Thr Ile Lys
                500                 505                 510

Asn Pro Glu Pro Ala Leu Leu Ala Thr Leu Asn Ala Ala Val Ala Ala
                515                 520                 525

Leu Glu Ala Thr Gly Gly Lys Val Val Cys Ser Cys Ser Thr Leu Pro
                530                 535                 540

Thr Trp Gly Pro Gly Arg Leu Phe Met Arg Asp Asp Gly Asn His Pro
545                 550                 555                 560

Gly Gly Glu Leu Asp Lys Lys Leu Tyr Thr Thr Glu His Pro Ala Trp
                565                 570                 575

Lys Lys Val Ser Glu Lys Met Ala Ser Ser Gly Ile Gly Val Asp Phe
                580                 585                 590

Phe Leu Ala Ala Pro Ser Gly Gly Tyr Leu Asp Ile Ala Thr Ile Gly
                595                 600                 605

His Val Ala Ala Thr Thr Gly Gly Glu Thr Phe Tyr Tyr Pro Asn Phe
                610                 615                 620

Ile Ala Pro Arg Asp Gly Ala Arg Leu Ser Met Glu Ile Thr His Ala
625                 630                 635                 640

Ile Thr Arg Glu Thr Gly Phe Gln Ala Leu Met Lys Val Arg Cys Ser
                645                 650                 655

Thr Gly Leu Gln Val Ala Ala Tyr His Gly Asn Phe Val Gln His Thr
                660                 665                 670

Phe Gly Ala Asp Leu Glu Ile Gly Val Ile Asp Ala Asp Lys Ala Leu
                675                 680                 685

Gly Val Ser Phe Ser His Asp Gly Lys Leu Asp Pro Lys Leu Asp Ala
                690                 695                 700

His Phe Gln Thr Ala Leu Leu Tyr Thr Thr Ala Ser Gly Gln Arg Arg
705                 710                 715                 720
```

```
Val Arg Cys Ser Asn Val Ile Ala Ser Val Ser Asp Thr Ser Lys Glu
            725                 730                 735

Ser Asn Thr Lys Glu Leu Ala Ile Arg Gln Cys Leu Lys Phe Val Asp
            740                 745                 750

Gln Asp Ala Val Val Gly Ile Phe Ala Lys Glu Ala Ser Thr Lys Leu
            755                 760                 765

Ala Thr Thr Ser Ala Asn Leu Gln Asp Val Arg Asn Trp Leu Thr Glu
            770                 775                 780

Arg Thr Ile Asp Ile Met Ala Tyr Tyr Lys Lys His Ser Ala Asn Gln
785                 790                 795                 800

Phe Pro Pro Ser Gln Leu Val Met Pro Glu Arg Leu Lys Glu Phe Cys
            805                 810                 815

Met Tyr Met Leu Gly Met Leu Lys Cys Arg Ala Phe Lys Gly Gly Ile
            820                 825                 830

Glu Asn Ser Asp Arg Arg Val His Glu Leu Arg Met Val Arg Ser Met
            835                 840                 845

Gly Pro Leu Glu Leu Ser Leu Tyr Leu Tyr Pro Arg Met Ile Ala Leu
            850                 855                 860

His Asn Leu Gln Pro Glu Glu Gly Phe Ala Asp Pro Glu Thr Gly His
865                 870                 875                 880

Leu Lys Met Pro Pro Ser Val Arg Thr Ser Phe Ser Arg Val Glu Pro
            885                 890                 895

Gly Gly Val Tyr Leu Val Asp Asn Gly Gln Gln Cys Leu Leu Trp Phe
            900                 905                 910

His Ala Gln Thr Ser Pro Asn Leu Ile Thr Asp Leu Phe Gly Glu Gly
            915                 920                 925

His Asp Ser Leu Lys Gly Leu Asp Pro Tyr Thr Ser Thr Leu Pro Val
930                 935                 940

Leu Glu Thr His Leu Ser Ala Gln Val Arg Asn Ile Ile Glu Phe Leu
945                 950                 955                 960

Lys Ser Met Arg Gly Ser Lys Gly Met Thr Ile Gln Leu Ala Arg Gln
            965                 970                 975

Gly Ile Asp Gly Ala Glu Tyr Glu Phe Ala Arg Met Leu Val Glu Asp
            980                 985                 990

Arg Asn Asn Glu Ala Lys Ser Tyr Val Asp Trp Leu Val His Ile His
            995                 1000                1005

Arg Gly Val Gln Leu Glu Leu Ser Gly Gln Arg Lys Lys Glu Gly
            1010                1015                1020

Asp Gly Glu Ala Thr Ala Val Met Ala Asn Phe Ala Gly Leu Arg
            1025                1030                1035

Pro Ala Tyr Trp
            1040

<210> SEQ ID NO 8
<211> LENGTH: 668
<212> TYPE: PRT
<213> ORGANISM: Hypocrea jecorina

<400> SEQUENCE: 8

Arg Gly Arg Ser Pro Ser Ala Gly Gly Phe Gln Ser Asp Ile Asn Gln
1               5                   10                  15

Ser His Ser Pro Ala Arg Ser Pro Leu Ala Pro Thr Asn Glu Gln Pro
            20                  25                  30

Ser Ala Gly Leu Gly Val Gly Leu Gly Gln Gln Gln Arg Ala Phe
            35                  40                  45
```

-continued

```
Ala Ala Pro Leu His Pro Asn Tyr Asp Ser Phe Gly Ala Asn Gly Phe
     50                  55                  60

Leu Gly Ala Gln Ala Asn Ala Val Asp Pro Thr Asn Gly Phe Asp Pro
 65                  70                  75                  80

Ser Ala Ser Phe Gly Gln Gln Pro Ala Thr Gly Pro Asp Ser Thr Leu
                 85                  90                  95

Ser Leu Asn Ala Gln Ala Gln His Asn Tyr Leu Ser Pro Asn Leu His
                100                 105                 110

Asp Gly Asp Phe Ser Leu Phe Pro Ser Ala Ala Glu Gln Gly Asp Gln
                115                 120                 125

Tyr Asn Ala Pro Leu Phe Glu Gln Pro Leu Gly Asp Leu Asn Ala
        130                 135                 140

Met Thr Ser Pro His Ser His Gln Ser Pro Thr Pro Pro Gln Leu Phe
145                 150                 155                 160

Gln Pro Asp Ser Leu Gln Ser Pro Pro Phe Asn Arg His Gln Phe Ser
                165                 170                 175

Ser Pro Pro Thr His Ser Arg Asn Ala Ser Leu Gly Pro Glu Ala Ala
                180                 185                 190

Leu Leu Pro Ser Gln Ile Gly Asp Trp Thr Gln Pro Gln Phe Gln Gly
        195                 200                 205

His Arg Arg Thr Pro Ser Glu Tyr Ser Asp Val Ser Ser Val Ala Pro
        210                 215                 220

Ser Pro His Leu Val Ser Ser Asp Thr Phe Asp Ala Asp Gln Ser Gly
225                 230                 235                 240

His Ser Pro Leu Gln Arg Pro Ala Asp Val Ser Leu Tyr Gln Glu Val
                245                 250                 255

Leu Gly Ile Gly Ser Phe Ser Leu Ala Asp His Gly Ser Pro Gly Tyr
                260                 265                 270

His Gly Arg Ser Pro Ser His Ser Pro Ala Ile Ser Pro Arg Ile Met
        275                 280                 285

Pro Gln Gln Met Pro Asp Thr Met Gln Pro Ser Phe Asn Leu Ile Pro
        290                 295                 300

Pro Asn Gly Gly Phe Asp Gly Val Ser Gly Tyr Pro Asp Leu Gln Pro
305                 310                 315                 320

Ser His Glu Ser Phe Pro Ser Leu Ser Gly Gly Met Gly Gly Asp Met
                325                 330                 335

His Gln Met Ala Pro Pro Ala Ile Asn Ile Asp Phe Ala Pro Thr Asn
        340                 345                 350

Ser Arg Gln Gly Ser Phe Glu Pro Pro Lys Ser Gln Met Asp Gln Asp
        355                 360                 365

Ser Leu Thr Pro Pro Glu Arg Gly Arg Pro Lys Ser Arg Pro Arg Ala
        370                 375                 380

Val Thr Asp Pro Phe His Pro Gly Ser Gly Ile Leu Pro Pro Gly Asn
385                 390                 395                 400

Leu Gly Ser Ser Leu Gly Val Asp Leu Ala Ala Arg Ser Asp Thr Ala
                405                 410                 415

Ser Arg Ser Leu Ser Pro Leu Asp Arg Ser Gly Thr Ser Ser Pro Ala
                420                 425                 430

Ser Arg Arg Arg Gln Ser Thr Ser Ser Val Pro Asn Asn Val Ile Ala
        435                 440                 445

Leu Arg Leu Ala Asp Pro Glu Tyr Gln Asn Ser Gln Glu Ala Gly Thr
        450                 455                 460
```

-continued

Ser Lys Arg Met Gln Lys His Pro Ala Thr Phe Gln Cys Thr Leu Cys
465                 470                 475                 480

Pro Lys Arg Phe Thr Arg Ala Tyr Asn Leu Arg Ser His Leu Arg Thr
            485                 490                 495

His Thr Asp Glu Arg Pro Phe Val Cys Thr Val Cys Gly Lys Ala Phe
        500                 505                 510

Ala Arg Gln His Asp Arg Lys Arg His Glu Ser Leu His Ser Gly Glu
    515                 520                 525

Lys Lys Phe Val Cys Lys Gly Asp Leu Lys Thr Gly Gly Gln Trp Gly
530                 535                 540

Cys Gly Arg Arg Phe Ala Arg Ala Asp Ala Leu Gly Arg His Phe Arg
545                 550                 555                 560

Ser Glu Ala Gly Arg Ile Cys Ile Lys Pro Leu Leu Asp Glu Met
            565                 570                 575

Val Glu Arg Gln Arg Gln Trp Gln Glu Gln Arg Met Gln Gln Asn Met
            580                 585                 590

Ala Gln Asn Met Ala Asn Pro Gln Val Met Gly Met Asp Ala Gly Pro
    595                 600                 605

Ala Tyr Pro Met Asp Ala Ser Gly Asn Tyr Thr Leu Pro Gln Ala Leu
    610                 615                 620

Leu Ala Gln Tyr Pro Ala Leu Ala Gln Met Asn Trp Ser Ala Thr Asp
625                 630                 635                 640

Met Gly Gly Gly Leu Asp Asp Glu Leu Ser Gly Arg Ser Ser Phe Asp
            645                 650                 655

Ala Ser Asp Tyr Asp Asp Gly Asp Asp Gly Gly Tyr
    660                 665

<210> SEQ ID NO 9
<211> LENGTH: 540
<212> TYPE: PRT
<213> ORGANISM: Hypocrea jecorina

<400> SEQUENCE: 9

Met Ser Leu Ser Lys Leu Ser Val Ser Leu Ala Leu Ala Gly Ser
1               5                   10                  15

Ala Ile Ala Gly Asp Leu Pro Ser Ile Thr Ala Lys Gly Ser Lys Phe
            20                  25                  30

Phe Tyr Pro Asn Gly Thr Gln Phe Phe Ile Lys Gly Val Ala Tyr Gln
        35                  40                  45

Gln Asp Val Gly Gln Ala Gly Ser Thr Asp Ser Ser Thr Ser Thr Phe
    50                  55                  60

Ile Asp Pro Leu Ser Ser Glu Ala Asn Cys Lys Arg Asp Val Pro Leu
65                  70                  75                  80

Leu Lys Gln Leu Gly Thr Asn Val Ile Arg Thr Tyr Ala Ile Asp Pro
            85                  90                  95

Lys Ala Asp His Ser Ala Cys Met Lys Leu Leu Asn Asp Ala Gly Ile
        100                 105                 110

Tyr Val Phe Ser Asp Leu Gly Glu Pro Ser Leu Ser Ile Asn Arg Asp
    115                 120                 125

Thr Pro Ala Trp Asn Thr Glu Leu Phe Asp Arg Tyr Lys Ala Val Val
    130                 135                 140

Asp Glu Met Ser Gln Tyr Pro Asn Val Ile Gly Tyr Phe Ala Gly Asn
145                 150                 155                 160

Glu Val Ser Asn Ala Lys Asn Asn Thr Gly Ala Ser Ala Tyr Val Lys
            165                 170                 175

```
Ala Ala Val Arg Asp Thr Lys Ala Tyr Ile Lys Ser Lys Lys Tyr Arg
            180                 185                 190

Trp Gln Gly Val Gly Tyr Ala Ala Asn Asp Asp Val Asp Ile Arg Ala
        195                 200                 205

Glu Ile Ala Asp Tyr Phe Asn Cys Gly Asp Gln Asp Glu Ala Ile Asp
    210                 215                 220

Phe Trp Gly Tyr Asn Ile Tyr Ser Trp Cys Gly Gln Ser Ser Met Gln
225                 230                 235                 240

Lys Ser Gly Tyr Asp Glu Gln Thr Thr Phe Phe Ser Asn Tyr Ser Val
                245                 250                 255

Pro Val Phe Phe Ala Glu Tyr Gly Cys Asn Leu Pro Ser Gly Ala Ala
            260                 265                 270

Ala Arg Ile Phe Gln Glu Thr Ala Ala Leu Tyr Ser Asp Glu Met Thr
        275                 280                 285

Lys Val Phe Ser Gly Gly Ile Val Tyr Met Tyr Phe Glu Glu Asp Asn
    290                 295                 300

Asp Tyr Gly Leu Val Lys Val Asn Asn Gly Ala Val Ser Lys Leu Lys
305                 310                 315                 320

Asp Phe Ser Ala Leu Gln Thr Gln Val Thr Lys Ala Asp Pro Lys Gly
                325                 330                 335

Val Asp Ala Asp Asp Tyr Lys Pro Thr Asn Lys Pro Ala Ser Cys Pro
            340                 345                 350

Ala Leu Thr Asp Asp Trp Gln Ala Ile Asn Ser Leu Pro Pro Thr Pro
        355                 360                 365

Asp Ala Ser Leu Cys Thr Cys Met Gln Ser Ser Leu Ser Cys Val His
    370                 375                 380

Ala Asp Asp Leu Asp Thr Lys Asp Phe Gly Asp Ile Phe Gly Phe Ile
385                 390                 395                 400

Cys Gly Lys Ser Pro Glu Val Cys Ala Gly Ile Asn Gly Asp Pro Ser
                405                 410                 415

Thr Gly Val Tyr Gly Ala Tyr Ser Met Cys Glu Asp Ala Ala Lys Leu
            420                 425                 430

Asp Tyr Val Leu Asp Ala Tyr Tyr Gln Ser Gln Lys Lys Ala Ser Thr
        435                 440                 445

Ala Cys Asp Phe Asn Gly Gln Ala Gln Val Val Ser Pro Lys Ala Ala
    450                 455                 460

Ser Thr Cys Ser Ala Ala Leu Ala Ser Ala Ser Ala Ile Asn Lys Gln
465                 470                 475                 480

Ala Ala Thr Ala Thr Ala Pro Val Gly Ala Gly Ser Thr Ser Gly Ser
                485                 490                 495

Lys Gly Ala Ala Thr Ser Thr Asn Ala Ala Val Ala Gly Arg Pro Val
            500                 505                 510

Ser His Leu Leu Ser Met Gly Glu Ile Ser Val Ala Leu Tyr Met Gly
        515                 520                 525

Val Ala Met Leu Ala Gly Gly Ala Met Ile Val Leu
    530                 535                 540

<210> SEQ ID NO 10
<211> LENGTH: 874
<212> TYPE: PRT
<213> ORGANISM: Hypocrea jecorina
```

<400> SEQUENCE: 10

```
Met Ala Arg Arg Glu Ser Leu Ser Glu Ile Arg Ala Ala Asn Pro Glu
1               5                   10                  15

Leu Phe Leu Thr Gly Asn Ile Ile Ser Ala Thr Phe Asn Ile Pro His
            20                  25                  30

Ala Val Thr Tyr His Lys Gly Gly Ala Trp Asp Leu Lys Pro Arg Arg
            35                  40                  45

Gly Gln Ser Ala Leu Ile Asp Ser Phe Ala Tyr Leu Ser Ser Asp Ala
        50                  55                  60

Thr Pro Trp Asn His Thr Val Ala Trp Thr Gly Glu Ile Ala Asn
65                  70                  75                  80

Pro Asp Asn Asp Pro Leu Ser Pro Pro Asp Thr Pro Ser Ala Ala Ala
                85                  90                  95

Thr Thr Ile Gly Ala Ala Asn Ser Leu Ser Ala Pro Val Pro Ile Asp
                100                 105                 110

Ala Thr Thr Arg Leu Pro Thr Pro Pro Val Asp Gly Leu Trp Ile
            115                 120                 125

Pro Lys Ala Asp Gln Thr Arg Leu Glu His Gln Leu Ser His Ser Thr
130                 135                 140

Thr Ile Arg Thr Val Pro Val Trp Leu Ala Asp Gln Ser Glu Ala Thr
145                 150                 155                 160

Asp Asp Gly Ile Met Leu Lys Asp Gln Ala Arg Trp Arg Arg Tyr Ala
                165                 170                 175

Glu His Asp Leu Tyr Thr Leu Phe His Tyr Lys Gln His Glu Pro Thr
            180                 185                 190

Asp Gly Arg Lys Glu Arg Ala Gln Trp Ala Asp Tyr Tyr Arg Met Asn
        195                 200                 205

Gln Lys Phe Ala Asn Lys Ile Ile Glu Ile Tyr Lys Pro Gly Asp Val
    210                 215                 220

Val Ile Val His Asp Tyr Tyr Leu Met Leu Leu Pro Ser Met Leu Arg
225                 230                 235                 240

Gln Arg Ala Pro Lys Met Tyr Ile Ser Phe Phe Leu His Ser Pro Phe
                245                 250                 255

Pro Ser Ser Glu Phe Leu Arg Cys Leu Pro Arg Arg Lys Glu Val Leu
            260                 265                 270

Glu Gly Val Leu Gly Ala Asn Leu Val Gly Phe Gln Ser Tyr Ser Tyr
        275                 280                 285

Ser Arg His Phe Leu Ser Cys Cys Thr Arg Ile Leu Gly Phe Pro Ser
    290                 295                 300

Asp Thr Leu Gly Ile Asp Ala Tyr Gly Ser Arg Val Gln Val Gly Val
305                 310                 315                 320

Phe Pro Ile Gly Ile Asp Ala Ala Lys Val Glu Thr Ala Ala Trp Ala
                325                 330                 335

Asp Thr Val Asn Glu Lys His Ala Ala Val Leu Lys Met Tyr Glu Gly
            340                 345                 350

Lys Lys Ile Ile Val Gly Arg Asp Arg Leu Asp Ser Val Arg Gly Val
        355                 360                 365

Ala Gln Lys Leu Gln Ala Phe Glu Arg Phe Leu Glu Leu Tyr Pro His
    370                 375                 380

Trp Arg Glu Lys Val Val Leu Ile Gln Val Thr Ser Pro Thr Ser Ile
385                 390                 395                 400
```

-continued

Glu Ala Glu Lys Gly Asp Pro Glu Asn Lys Asn Ala Ser Arg Val Asn
            405                 410                 415
Glu Leu Ile Thr Lys Ile Asn Gly Glu Tyr Gly Ser Leu Gly Phe Ser
            420                 425                 430
Pro Val Gln His Tyr Pro Gln Tyr Leu Ser Gln Ala Glu Tyr Phe Ala
            435                 440                 445
Leu Leu Arg Ala Ala Asp Ile Gly Leu Ile Thr Ser Val Arg Asp Gly
            450                 455                 460
Met Asn Thr Thr Ser Leu Glu Tyr Val Val Cys Gln Lys Asp Ser Asn
465                 470                 475                 480
Gly Pro Leu Ile Leu Ser Glu Phe Ser Gly Thr Ala Gly Ser Leu Arg
            485                 490                 495
Asp Ala Ile His Ile Asn Pro Trp Asp Leu Thr Gly Val Ala Glu Lys
            500                 505                 510
Ile Asn Ala Ala Leu Glu Met Ser Glu Glu Arg Val Lys Met Gln
            515                 520                 525
Thr Ser Leu Tyr Thr His Val Thr Gln Asn Val Gln Ser Trp Ile
            530                 535                 540
Thr Lys Phe Ile Arg Lys Phe His Ala Ala Leu Ser Glu Thr Asn Ser
545                 550                 555                 560
Val Thr Ser Thr Pro Leu Leu Asp Arg Ala Leu Leu Leu Ser Arg Tyr
            565                 570                 575
Arg Ala Ala Lys Lys Arg Leu Phe Met Phe Asp Tyr Asp Gly Thr Leu
            580                 585                 590
Thr Pro Ile Val Arg Glu Pro Ser Ala Ala Val Pro Ser Glu Arg Ile
            595                 600                 605
Ile Arg Tyr Leu Gln Ser Leu Ala Ser Asp Pro Arg Asn Ala Val Trp
            610                 615                 620
Ile Ile Ser Gly Arg Asp Gln Glu Phe Leu Gln Gln His Leu Gly His
625                 630                 635                 640
Ile Pro Arg Ile Gly Phe Ser Ala Glu His Gly Ser Phe Met Arg Asp
            645                 650                 655
Pro Gly Ser Asp Glu Trp Val Asn Leu Ala Glu Lys Phe Asp Met Gly
            660                 665                 670
Trp Gln Ala Glu Val Met Glu Val Phe Gln Arg Tyr Thr Asp Lys Val
            675                 680                 685
Pro Gly Ser Phe Ile Glu Arg Lys Arg Cys Ala Leu Thr Trp His Tyr
            690                 695                 700
Arg Leu Ala Glu Pro Glu Gln Gly Leu His Met Ser Arg Glu Cys His
705                 710                 715                 720
Arg Glu Leu Glu Thr Gly Ile Ala Gln Arg Trp Glu Val Glu Val Met
            725                 730                 735
Pro Gly Lys Ala Asn Ile Glu Val Arg Pro Thr Phe Ile Asn Lys Gly
            740                 745                 750
Glu Ile Ala Lys Arg Leu Val Ala Thr Tyr His Asn Pro Gly Ala Ala
            755                 760                 765
Pro Thr Asp Lys Asp Pro Tyr Pro Gly Lys Ile Glu Phe Ala Leu Cys
            770                 775                 780
Ser Gly Asp Asp Phe Thr Asp Glu Asp Met Phe Arg Ser Leu Asn Gly
785                 790                 795                 800
Ala Cys Gly Thr Ile Leu Glu Asp Gln His Val Phe Thr Val Thr Val
            805                 810                 815

```
Gly Ala Ser Thr Lys Val Thr Leu Ala Lys Trp His Leu Leu Glu Pro
                820                 825                 830

Glu Asp Val Ile Glu Cys Val Gly Leu Leu Ala Gly Ala Gly Asp Pro
                835                 840                 845

Ala Ser Leu Glu Arg Val Gly Glu Val Asn Leu Ala Ala Leu Ser Gln
            850                 855                 860

Val Glu Gly His Ile Pro Ala Glu Glu Leu
865                 870

<210> SEQ ID NO 11
<211> LENGTH: 997
<212> TYPE: PRT
<213> ORGANISM: Aspergillus clavatus

<400> SEQUENCE: 11

Met Thr Met Leu Ser Pro Thr Ser Asp His Pro Gln Gly Ala Ser Met
1               5                   10                  15

Lys Asp Ile Glu Asn Pro Gly Asn Asp Ser Pro Ala Leu Glu Gly Ser
                20                  25                  30

Thr Gln Ala Glu Lys Thr Val Asp Asn Pro Ser Arg Ser Pro Thr Pro
            35                  40                  45

Gln Leu Gln Thr Ala Glu Leu Ala Gln Val Leu Ser Pro Leu Ala Val
    50                  55                  60

Arg Gln Thr Gln Ser Ile Ser Thr Arg Ser Gln His Asn Arg Leu Glu
65                  70                  75                  80

Tyr Leu Cys Leu Pro Asn Ala Thr Asn Arg Gly Lys Leu Ser Arg Ser
                85                  90                  95

Leu Ala Arg Arg Ala Thr Leu Leu Gly Trp Phe Asp Gln Ala Ala Thr
                100                 105                 110

Gln Ser Gly Gln Glu Ser Gln Ser Ser Val Cys Val Ala Val Lys Leu
            115                 120                 125

Pro Asp Asp Gly Tyr Ser Phe Ser Pro Ser Asn Ile Thr Pro Ala Leu
    130                 135                 140

Ser Lys Ala Ile Thr Arg Leu Asn Glu Met Ala Val Val Ala Leu Ser
145                 150                 155                 160

Ser Arg Val Val Asp Lys Gly Leu Ser Gly Ile Leu Pro Gly Gln Lys
                165                 170                 175

Ser Phe Leu Val Glu Ser Thr Ser Thr Arg Ile Pro Ile Val Ala Thr
                180                 185                 190

Leu Asp Asp Val Glu Pro Thr Leu Ala His Tyr Ser Arg Ala Cys Ile
            195                 200                 205

Val Met Glu Gln Lys Ile Val Leu Val Trp Ser His Asp Thr Ala Gly
    210                 215                 220

Ile Leu Asn Val Ala Tyr Asp Val Glu Thr Gln Leu Gly Gly Gln Ser
225                 230                 235                 240

Pro Lys Ile Ser Asn Ala Thr Thr Pro Arg Ile Ser Gly Arg Ser Thr
                245                 250                 255

Pro Met Asp Pro Tyr Arg Thr Asp Asp Leu Gln Lys Pro Ala Asn Val
                260                 265                 270

Leu Gln Pro Val Arg Gly Ala Leu Asp Glu Lys Gln Ala Ile Tyr Ser
            275                 280                 285

Lys Ala Val Ala Leu Glu Glu Gly Glu Asp Asn Glu Val Pro Asp Leu
    290                 295                 300

Glu Arg Asn Ala Ala Pro Arg Pro Val Leu Leu Val His Thr Val Lys
305                 310                 315                 320
```

```
Ile Ser Leu Ala Ile Met Leu Val Ile Val Thr Gln Ser Leu Gly Val
                325                 330                 335

Ala Arg Leu Leu Asn Glu Phe Gln Trp Asp Gly Gln Tyr Thr Arg Phe
                340                 345                 350

Ala Leu Val Val Thr Ile Pro Pro Leu Ala Leu Phe Ser Leu Phe Phe
                355                 360                 365

Phe Ile Val Leu Val Thr Ser Val Phe Gln Leu Phe Leu Pro Ala Ser
        370                 375                 380

Phe Cys Leu Lys Asn Ser Lys Phe His Ser Gly Asp Thr Glu Asp Ser
385                 390                 395                 400

Ser Ala Val Lys Pro Asn Pro Lys Ala His Gly Glu Tyr Glu Leu Pro
                    405                 410                 415

His Ile Thr Ile Gln Met Pro Val Tyr Lys Glu Gly Leu Lys Gly Val
                420                 425                 430

Ile Val Pro Thr Met Ile Ser Val Leu Ala Ala Val Gln Tyr Tyr Glu
                435                 440                 445

Glu Gln Gly Gly Thr Ala Ser Val Phe Val Asn Asp Gly Met Gln
        450                 455                 460

Val Ile Gln Ser Asp Leu Ala Glu Ala Arg Lys Gln Tyr Tyr Arg Glu
465                 470                 475                 480

Asn Gly Ile Gly Phe Thr Ala Arg Pro Pro Asn Lys Lys Ser Pro Val
                    485                 490                 495

Gln Lys Gly Gly Trp Gly Ser Trp Phe Arg Lys Ser Lys Pro Ala Thr
                500                 505                 510

Thr Glu Pro Ala Asp Ser Glu Glu Pro Glu Gly Pro Tyr Thr Pro Gln
                515                 520                 525

Ala Leu Ala Asn Lys Ile Gly Phe Glu Arg Lys Gly Lys Phe Lys Lys
                530                 535                 540

Ala Ser Asn Met Asn Tyr Gly Leu Ala Phe Ser Leu Arg Val Glu Asp
545                 550                 555                 560

Glu Leu Ala Arg Leu Thr Gln Ile Glu Thr Glu Arg Arg Gly Cys Thr
                    565                 570                 575

Val Asp Asp Leu Thr Ala Glu Asp Asp Arg Leu Tyr Gln Gln Ala
        580                 585                 590

Leu Asp Asn Met Leu Ala Ala Asp Glu Glu Arg Thr Trp Ala Glu Gly
            595                 600                 605

Asn Ile Arg Ile Gly Glu Leu Ile Leu Leu Ile Asp Cys Asp Thr Arg
610                 615                 620

Val Pro Val Asp Cys Leu Leu Tyr Gly Ala Leu Glu Met His Glu Ser
625                 630                 635                 640

Pro Glu Val Ala Ile Leu Gln His Gly Ser Gly Val Met Gln Val Val
                    645                 650                 655

His Asn Val Phe Glu Asn Gly Ile Thr Tyr Phe Thr Asn Val Val Tyr
                660                 665                 670

Thr Ala Ile Lys Tyr Gly Val Gly Ser Gly Asp Val Ser Pro Phe Val
                675                 680                 685

Gly His Asn Ala Phe Leu Arg Trp Arg Ala Leu Gln Ser Ile Glu Phe
            690                 695                 700

Val Asp Pro Ser Asp Gly Gln Thr Lys Trp Trp Ser Asp Thr His Val
705                 710                 715                 720

Ser Glu Asp Phe Asp Ile Ser Leu Arg Leu Gln Met Gln Gly Met Val
                    725                 730                 735
```

-continued

```
Val Arg Leu Ala Thr Tyr His Asn Gly Glu Phe Lys Glu Gly Val Ser
            740                 745                 750

Leu Thr Leu Tyr Asp Glu Leu Thr Arg Trp Glu Lys Tyr Ala Tyr Gly
            755                 760                 765

Cys Asn Glu Leu Val Phe His Pro Phe Tyr Gln Trp Val Tyr Lys Gly
            770                 775                 780

Pro Val Thr Arg Leu Phe Leu Arg Phe Leu Trp Ser Asn Met Pro Val
785                 790                 795                 800

Thr Ser Lys Val Thr Ile Ile Ala Tyr Ile Phe Thr Tyr Ala Ile
                805                 810                 815

Gly Ser Gly Met Leu Leu Ala Thr Val Asn Tyr Val Ile Leu Gly Leu
            820                 825                 830

Phe Asp Ser Asp Ile Asp His Leu Tyr Leu Pro Ser Trp Gly Ile Trp
            835                 840                 845

Cys Ser Leu Val Val Val Phe Asn Gly Phe Ser Ser Ile Ala Phe Ser
            850                 855                 860

Met Val Arg His Gln Leu Lys Glu Glu Thr Phe Trp Arg Ala Leu Leu
865                 870                 875                 880

Asp Ala Ile Lys Trp Leu Pro Phe Leu Ile Ile Tyr Phe Gly Gly Ile
                885                 890                 895

Ser Leu Asn Cys Ala Lys Ala Ile Leu Cys His Ala Phe Ser Ile Asn
            900                 905                 910

Leu Glu Trp Ala Ser Thr Ala Lys Glu Met Gly Pro Thr Gly Phe Tyr
            915                 920                 925

Ile Gly Met Asp Lys Met Val Arg Arg Phe Lys Trp Thr Trp Ala Ile
930                 935                 940

Cys Leu Val Leu Ala Gly Val Met Ile Tyr Phe Ala Val Gly Ala Pro
945                 950                 955                 960

Trp Gly Trp Thr Ile Thr Pro Gly Pro Tyr Ser Thr Ala Asn Val Ala
                965                 970                 975

Ile Ala Pro Leu Ala Ile Gln Ile Cys Ser Ala Ser Phe Leu Pro Phe
            980                 985                 990

Phe Leu Gly Leu Asn
            995

<210> SEQ ID NO 12
<211> LENGTH: 988
<212> TYPE: PRT
<213> ORGANISM: Penicillium oxalicum

<400> SEQUENCE: 12

Met Glu Glu Trp Pro Arg Asn Ala Asp Glu Pro Tyr Gly Ser Gln Arg
1               5                   10                  15

Tyr Gln Glu Asp Val Gln Asp Leu Val Ser Leu Pro Ser Arg Ser Ser
                20                  25                  30

Thr Pro His Leu Asp Arg Ala Glu Ile Gly Arg Val Leu Ser Pro Ser
            35                  40                  45

Val Gln Pro Gly Arg Asn Ser Arg Ser Arg Arg Ser Asn Pro Ser Ile
50                  55                  60

Ala His Ser Phe Thr Ser Pro Ser Ile Ser Glu Ser Gly Glu Gly Glu
65                  70                  75                  80

Asp Pro Ser Ser Thr Ala Arg Tyr Leu Ala Arg Arg Ala Thr Leu Leu
                85                  90                  95

Gly Trp Phe Asp Glu Val Asp Val Glu Asp Gly Arg Asn Ser Trp Ser
            100                 105                 110
```

-continued

```
Ser Thr Cys Ile Ser Leu Arg Arg Ala Asp Asn Glu Tyr Thr Phe Phe
        115                 120                 125

Pro Tyr Asn Val Asn Pro Ser Leu Ile Asp Ala Ile Thr Arg Leu Gly
        130                 135                 140

Glu Thr Ala Ala Met Ala Met Ser Ser Arg Phe Thr Ser Met Leu Ile
145                 150                 155                 160

Asp Ser Ile Leu Pro Gly Gln Lys Ser Leu Val Val Glu Ser Thr Ser
                165                 170                 175

Ala Arg Ile Pro Val Val His Ser Leu Asn Asp Val Ser Ser Asn Leu
                180                 185                 190

Val His Phe Ala Arg Ala Cys Ile Val Val Gln Glu Lys Leu Val Leu
                195                 200                 205

Ile Trp Ser His Asn Ala Gly Thr Ile Leu His Val Ala His Asp Val
        210                 215                 220

Glu Arg Gln Leu Gly Lys Lys Ser Pro Arg Ile Ser Thr Ala Thr Thr
225                 230                 235                 240

Pro Arg Ala Ser Gly Arg Ser Ser Pro Phe Asp Val Asp Ala Asp Val
                245                 250                 255

Ala Pro Ser Thr Gln Ile Ser Ile Lys Ala Lys Ile Asp Ser Phe Pro
                260                 265                 270

Val Arg Gly Ala Leu Asp Glu Lys His Glu Val Tyr Ser Lys Ala Val
                275                 280                 285

Ala Leu Glu Glu Gly Thr Val Glu Asp Asp Thr Pro Val Asp Leu Glu
        290                 295                 300

Gly Asn Leu Pro Pro Arg Pro Ala His Arg Ile His Ala Val Lys Ile
305                 310                 315                 320

Ser Leu Ala Ile Met Leu Val Ile Leu Thr Gln Ser Leu Gly Val Ser
                325                 330                 335

Arg Leu Val Asn Glu Phe Ala Trp Asp Gly Ser Phe Thr Arg Phe Ala
                340                 345                 350

Leu Val Val Thr Ile Pro Pro Leu Ala Leu Phe Ser Leu Phe Phe Phe
        355                 360                 365

Ile Val Leu Val Thr Ser Ala Phe Gln Leu Phe Leu Pro Ala Ser Phe
        370                 375                 380

Cys Leu Lys Asn Ser Lys Phe His Ser Ala Ile Lys Pro Asn Pro Arg
385                 390                 395                 400

Phe His Arg Asp Tyr Glu Leu Pro His Ile Thr Val Gln Met Pro Val
                405                 410                 415

Tyr Lys Glu Gly Leu Lys Gly Val Ile Val Pro Thr Met Met Ser Val
                420                 425                 430

Leu Ala Ala Val Gln Tyr Tyr Glu Glu Gln Gly Gly Thr Ala Ser Val
                435                 440                 445

Phe Ile Asn Asp Asp Gly Met Gln Cys Ile Gln Pro Glu Leu Ala Glu
        450                 455                 460

Ala Arg Lys Gln Tyr Tyr Arg Glu Asn Gly Ile Gly Tyr Thr Ala Arg
465                 470                 475                 480

Leu Pro Asn Arg Lys Thr Ala Ser Lys Lys Arg Gly Phe Gly Trp
                485                 490                 495

Phe Arg Lys Ala Lys Ser Ala Glu Gly Asp Ala Glu Thr Glu Ala Glu
                500                 505                 510

Glu Asp Thr Ser Ser Pro Gln Ala Ile Ala Asn Lys Ile Gly Phe Glu
        515                 520                 525
```

```
Arg Lys Gly Lys Phe Lys Lys Ala Ser Asn Met Asn Tyr Gly Leu Ala
    530             535                 540

Phe Ser Asn Arg Val Glu Asp Glu Leu Ala Arg Leu Ala Asp Leu Glu
545             550              555                 560

Cys Gln Gln Arg Gly Cys Ser Asn Asp Asp Leu Thr Phe Glu Asp Asp
                565             570                 575

Asp Arg Leu Tyr Gln Gln Ala Leu Ser Asn Met Leu Ala Glu Asp Glu
            580             585                 590

Gly Arg Thr Trp Ala Glu Gly Asn Val Arg Ile Gly Glu Ile Ile Leu
            595             600             605

Ile Ile Asp Cys Asp Thr Arg Val Pro Val Asp Cys Leu Leu Tyr Gly
    610             615             620

Ala Leu Glu Met His Glu Ser Pro Glu Val Ala Ile Val Gln His Gly
625             630             635                 640

Ser Gly Val Met Gln Val Val His Asn Met Phe Glu Asn Gly Ile Thr
                645             650             655

Tyr Phe Thr Asp Val Val Tyr Thr Ala Ile Lys Tyr Gly Val Gly Ser
            660             665             670

Gly Asp Val Ser Pro Phe Val Gly His Asn Ala Phe Leu Arg Trp Lys
        675             680             685

Ala Leu Gln Ser Ile Gln Phe Val Asp Pro Ala Asp Gly Gln Thr Lys
    690             695             700

Trp Trp Ser Asp Ala His Val Ser Glu Asp Phe Asp Ile Ser Leu Arg
705             710             715                 720

Leu Gln Met Gln Gly Met Thr Val Arg Leu Ala Thr Tyr His Asn Gly
            725             730             735

Gly Phe Lys Glu Gly Val Ser Leu Thr Leu Tyr Asp Glu Leu Thr Arg
            740             745             750

Trp Glu Lys Tyr Ala Tyr Gly Cys Asn Glu Leu Val Phe Asn Pro Phe
            755             760             765

Tyr Gln Trp Pro Tyr Lys Gly Pro Val Thr Arg Leu Phe Leu Arg Phe
            770             775             780

Leu Trp Ser Asn Met Pro Val Thr Ser Lys Val Thr Ile Ile Ala Tyr
785             790             795                 800

Ile Phe Thr Tyr Tyr Ala Ile Ala Ser Gly Met Met Leu Ser Val Val
                805             810             815

Asn Tyr Val Ile Val Gly Leu Phe Asn Ser Glu Val Asp His Ile Tyr
            820             825             830

Leu Arg Ser Trp Gly Ile Trp Ile Ser Leu Val Val Val Phe Asn Gly
            835             840             845

Val Ala Ser Val Ala Phe Ser Met Ala Arg His Gln Leu Lys Glu Met
    850             855             860

Val Phe Trp Lys Ala Leu Leu Lys Ser Ala Leu Trp Leu Pro Phe Leu
865             870             875                 880

Val Val Phe Phe Gly Gly Ile Ser Leu Asn Cys Ala Lys Ala Ile Leu
                885             890             895

Cys His Ala Phe Ser Ile Asn Ile Glu Trp Ala Ser Thr Ala Lys Glu
            900             905             910

Pro Gly Pro Ser Gly Phe Phe Ile Gly Leu Asp Lys Met Val Lys Gln
            915             920             925

Phe Lys Tyr Thr Trp Ala Ile Cys Leu Phe Leu Ala Ala Val Met Ile
930             935             940
```

```
Phe Met Ala Leu Gly Thr Pro Trp Gly Trp Gln Ile Lys Pro Gly Glu
945                 950                 955                 960

Tyr Ser Thr Ala Ser Ile Ala Ile Gly Pro Leu Ala Ile Gln Ile Cys
                965                 970                 975

Asn Ala Ala Ile Leu Pro Leu Ile Leu Gly Leu Asn
            980                 985

<210> SEQ ID NO 13
<211> LENGTH: 920
<212> TYPE: PRT
<213> ORGANISM: Talaromyces cellulolyticus

<400> SEQUENCE: 13

Met Ser Ser Leu Phe Pro Thr Arg Trp Ser Phe Arg Gly His Lys Thr
1               5                   10                  15

Pro Lys Gly Asp Gly Thr Pro Thr Glu Thr Ala Ser Gln Arg Asp Ser
            20                  25                  30

Leu Pro Val Ser Glu Ser Gly Arg Ser Arg Gly Gln Gly Tyr Phe
        35                  40                  45

Asp Arg Arg His Val Asn Asn Ser Ile Asp Asp Ala Ser Lys Tyr Lys
50                  55                  60

Ala Met Ile Lys Phe Phe His Val Arg Leu Thr Ala Tyr Gln Trp Leu
65                  70                  75                  80

Pro Pro Pro Thr His Pro Gln His Ser Ser Thr Gly Val Phe Leu Arg
                85                  90                  95

Arg Ser Arg Gly Ile Tyr Met Ser Glu Pro Glu Asp Ile Asn Pro Leu
            100                 105                 110

Leu Leu Ala Ala Ile Gln Arg Ile Asn Ala Thr Ile Ala Phe Thr Met
        115                 120                 125

Met Thr Glu Thr Thr Ser Ile Ile Thr Ser Gln Leu Ala Pro Gly Gln
130                 135                 140

Thr Glu Leu Ile Leu Pro Asn Gly Tyr Gln Val Gln Ile Ile Glu Ser
145                 150                 155                 160

Tyr Ala Asp Ile Val Gly Ser His Ser Asn Met Val Lys Lys Tyr Gln
                165                 170                 175

Tyr Ala Ala Leu Ile Arg Glu Glu Gln Leu Leu Leu Val Trp Asn Asp
            180                 185                 190

Asp Leu Asn Ala Ile Leu Asn His Ala Ala Asp Val Glu Gly Lys Leu
        195                 200                 205

Leu Ser Leu Ile Trp Gly Ser Pro Ile Pro Thr Phe Asn Leu Gln Ala
210                 215                 220

Val Pro Met Met Thr Pro Gly Glu Ser Val Val Ala Ser Pro Asn Asp
225                 230                 235                 240

Ser Leu Tyr His Leu Ala Leu Glu Pro Arg Glu Ser Pro Ala Ala Ala
                245                 250                 255

Glu Asp Ser Gly Thr Ser Arg Asp Ala Ser Pro Arg Arg Met Ile Asn
            260                 265                 270

Glu Glu Val Lys Arg Pro Lys Glu Ser Leu Glu Arg Pro Leu Ala Val
        275                 280                 285

Thr Ser Ala Ile Phe Val Gly Met Ala Gly Met Leu Leu Val Ile Leu
290                 295                 300

Leu Leu Gly Phe Gly Ile Ser Asn Leu Leu Leu Glu Tyr Ser Val Asp
305                 310                 315                 320
```

```
Gly Gly Ala Met Arg Phe Ala Leu Thr Ala Thr Ile Pro Phe Phe Leu
            325                 330                 335

Leu Phe Ser Ile Phe Phe Met Ile Val Ile Phe Thr Asp Ile Phe Gln
            340                 345                 350

Ala Val Gly Pro Val Lys Thr Leu Lys Ser Asn Ser Arg Phe Tyr Ser
            355                 360                 365

Pro Ile Ala Pro Asp Leu Lys Thr Ala Tyr Ser Leu Gly Phe Thr Pro
            370                 375                 380

Pro Arg Val Thr Ile Gln Met Pro Ile Tyr Thr Glu Ser Leu Glu Gly
385                 390                 395                 400

Val Ile Lys Pro Thr Ile Ser Ser Leu Lys Thr Ala Ile Ser His Tyr
            405                 410                 415

Glu Ser His Gly Gly Thr Ala Asn Ile Phe Ile Asn Asp Asp Gly Phe
            420                 425                 430

Ala Leu Leu Ser Glu Glu Gln Gln His Glu Arg Ile Asn Phe Tyr His
            435                 440                 445

Asp Asn Asn Ile Gly Trp Val Ala Arg Pro Lys Asn Asn Glu Asp Gly
            450                 455                 460

Tyr Ile Arg Lys Gly Lys Phe Lys Lys Ala Ser Asn Met Asn Phe Ala
465                 470                 475                 480

Leu Asn Val Ser Asn Lys Val Glu Met Glu Leu Ile Gln Arg Met Ala
            485                 490                 495

Pro Thr Leu Glu Lys Ser Asp Met Val Asp Pro Met Glu Glu Glu Leu
            500                 505                 510

Val Tyr Arg Glu Ala Phe Asp His Val Ile Gln Ser Asp Pro Arg Ile
            515                 520                 525

Arg Gly Ala Gly Gly Asp Ile Arg Val Gly Glu Phe Ile Leu Ile Val
            530                 535                 540

Asp Ser Asp Thr Arg Ile Pro Ala Asp Cys Leu Leu Tyr Gly Ala Ala
545                 550                 555                 560

Glu Met Phe Leu Ser Pro Glu Val Ala Ile Ile Gln His Ser Thr Ser
            565                 570                 575

Val Met Gln Val Ser Gln Asp Tyr Phe Glu Asn Gly Ile Thr Tyr Phe
            580                 585                 590

Thr Asn Leu Ile Tyr Ser Ala Ile Arg Phe Ala Val Gly Ser Gly Glu
            595                 600                 605

Thr Ala Pro Phe Val Gly His Asn Ala Phe Leu Arg Trp Gln Ala Val
            610                 615                 620

Gln Ser Val Gly Arg Pro Asp Asp Gly Tyr Val Ser Phe Trp Ser Glu
625                 630                 635                 640

Ser His Val Ser Glu Asp Phe Asp Ile Ala Leu Arg Leu Gln Ile Gln
            645                 650                 655

Gly Asn Ile Ile Arg Leu Ala Ser Tyr His Asn Asp Glu Phe Lys Glu
            660                 665                 670

Gly Val Ser Leu Thr Ile Tyr Asp Glu Leu Ser Arg Trp Glu Lys Tyr
            675                 680                 685

Ala Tyr Gly Cys Asn Glu Leu Val Phe Asn Pro Val His Thr Trp Phe
            690                 695                 700

Tyr Arg Gly Pro Leu Thr Lys Leu Phe Met Thr Phe Leu Trp Ser Asn
705                 710                 715                 720

Leu Gln Leu Ser Ser Lys Ile Thr Ile Leu Gly Tyr Ile Ser Ser Tyr
            725                 730                 735
```

-continued

```
Tyr Ala Leu Ala Ser Gly Phe Pro Leu Thr Val Leu Asn Tyr Phe Leu
                740                 745                 750

Val Gly Trp Phe Glu Gly Tyr Leu Asp Lys Phe Tyr Met Glu Ser Trp
            755                 760                 765

Lys Val Phe Leu Ser Leu Leu Val Phe Ser Ala Ala Gly Asn Val
        770                 775                 780

Cys Leu Ala Ile Ile Arg Tyr Arg Leu Gly Glu Lys Pro Leu Leu Ala
785                 790                 795                 800

Ser Leu Val Glu Asn Phe Met Trp Met Pro Met Phe Ala Ile Phe Phe
                805                 810                 815

Gly Gly Leu Ser Phe His Leu Ser Leu Ala Ile Leu Ser His Met Phe
                820                 825                 830

Gly Ile Asn Met Ser Trp Gly Thr Thr Ala Lys Glu Lys Asp Asp Ser
                835                 840                 845

Asn Phe Phe Lys Glu Ile Pro Lys Ile Phe Lys Ser Phe Lys Trp Met
                850                 855                 860

Tyr Ala Val Val Leu Pro Phe Phe Pro Ala Met Ile Tyr Leu Ala Cys
865                 870                 875                 880

Phe Ala Pro Asn Gly Trp Thr Ile Thr Glu Val Gly Ala Ile Val Pro
                885                 890                 895

Met Ser Val Thr Leu Ala Ser His Ala Leu Leu Pro Leu Leu Leu Asn
                900                 905                 910

Pro Ser Leu Met Val Phe Asn Tyr
                915                 920

<210> SEQ ID NO 14
<211> LENGTH: 884
<212> TYPE: PRT
<213> ORGANISM: Fusarium oxysporum

<400> SEQUENCE: 14

Met Gly Ile Gly Ser Tyr Phe Lys Ala Asp Ile Pro Pro Gln Thr Pro
1               5                   10                  15

Ile Gly Pro Pro Arg Arg Pro Ser His Arg Pro Ser Met Ser Leu
            20                  25                  30

His Ala Pro Ile Ile Glu Glu Lys Ile Pro Ala Ala Val Val Glu
        35                  40                  45

Leu His Ser Ala Ala Gly Pro Lys Phe Thr Ala Gly Pro Pro Ser Ile
    50                  55                  60

Ala Pro Ser Ser Lys Ser Gly Asn Ser Asn Leu Leu Asp Asp Ile Lys
65                  70                  75                  80

His Glu Val Met Val Asn Tyr Leu Tyr Gln Gln Gln Cys Ser Gln Leu
                85                  90                  95

Trp Val Gly Asp Gly Ser Gly Glu Ile Glu Gly Val Leu Leu Arg Lys
            100                 105                 110

Ser Arg Gly Gln Tyr Met Ala Cys Pro Pro Gln Leu Gly Gln Ser Pro
        115                 120                 125

Phe Ala Ile Ala Cys Thr Ala Leu Asn Val Gln Cys Ala Met Thr Val
130                 135                 140

Asn Ser Arg Val Ile Lys Thr Phe Leu Gln Trp Ser Pro Asp Ala Val
145                 150                 155                 160

Asp Val Pro Leu Met Asn Gly Leu Arg Val Gln Ile Leu Pro Thr Val
                165                 170                 175

Asn Asp Leu Pro Arg Ala Arg Lys His Gln Phe Ala Ala Phe Ile Ala
            180                 185                 190
```

```
Ser Asp Gly Leu Leu Val Val Trp Asp Asp Ala Leu Asn Leu Met
    195                 200                 205

Ala Arg Ala Lys Ile Ile Glu Ser Glu Leu Met Glu Leu Val Trp Asn
210                 215                 220

Ser Gly Gln Ser Val Asp Glu Asp Arg Asp Ser Thr Ile Ala Ala
225                 230                 235                 240

Glu Tyr Glu Ile Asp Glu Glu Ser Gly Glu Ile Lys Pro Glu Ala Arg
                    245                 250                 255

Pro Val His Leu Gln Asn Ala Val Leu Val Ser Leu Thr Leu Leu Leu
                260                 265                 270

Val Met Ala Ser Leu Gly Ala Ala Trp Arg Gln Leu Ala Val Glu Ile
        275                 280                 285

Ala Ile Asp Gly Asp Tyr Lys Arg Leu Gly Leu Val Ala Leu Phe Pro
    290                 295                 300

Ile Gln Ile Phe Phe Ser Leu Phe Phe Ala Gln Val Ile Val Gly Cys
305                 310                 315                 320

Leu Ala Gln Ile Phe Gly Pro Ile Arg Gln Leu Thr Ile Asn Ser Lys
                325                 330                 335

Phe Tyr Ser Ala Arg Pro Pro Arg Arg Leu Gln Gly Ala Thr Leu Pro
                340                 345                 350

His Ile Thr Ile Gln Cys Pro Val Tyr Lys Glu Gly Leu Asn Ala Val
            355                 360                 365

Ile Leu Pro Thr Val Lys Ser Ile Lys Gln Ala Met Ser Thr Tyr Glu
            370                 375                 380

Leu Gln Gly Gly Ser Ala Asn Met Phe Ile Asn Asp Gly Leu Gln
385                 390                 395                 400

Leu Leu Ser Glu Glu Arg Asp Ala Arg Ile Asp Phe Tyr Ala Asp
                405                 410                 415

Asn Ser Ile Gly Trp Val Ala Arg Pro Lys His Gly Glu Asp Gly Phe
                420                 425                 430

Ile Arg Lys Gly Lys Phe Lys Lys Ala Ser Asn Met Asn Phe Gly Leu
            435                 440                 445

Met Ile Ser Cys Lys Val Glu Glu Arg Leu Gln Leu Ile Lys Arg Pro
    450                 455                 460

Ala Asp Trp Ser Gln Ser Asp Glu Ala Leu Ala Tyr Glu Gln Ala Leu
465                 470                 475                 480

Lys Asp Val Leu Glu Glu Asn Gly Arg Ala Trp Ala Asp Gly Asn Ile
                485                 490                 495

Arg Val Gly Asp Tyr Ile Leu Leu Ile Asp Ser Asp Thr Arg Val Pro
                500                 505                 510

Thr Asp Cys Leu Leu Asp Ser Val Ser Glu Met Glu Gln Ser Pro Asp
            515                 520                 525

Val Gly Ile Met Gln Phe Ser Ser Gly Val Met Gln Val Val His Thr
    530                 535                 540

Tyr Phe Glu Asn Gly Ile Thr Phe Phe Thr Asp Leu Ile Tyr Thr Ala
545                 550                 555                 560

Ile Arg Phe Thr Val Ser Asn Gly Asp Val Ala Pro Phe Val Gly His
                565                 570                 575

Asn Ala Ile Leu Arg Trp Ser Ala Ile Gln Gln Val Ala Tyr Gln Asp
                580                 585                 590

Glu Asp Gly Tyr Asp Lys Phe Trp Ser Glu Ser His Val Ser Glu Asp
            595                 600                 605
```

```
Phe Asp Met Ser Leu Arg Leu Gln Cys Asn Gly Tyr Ile Ile Arg Leu
    610                 615                 620

Ala Ala Trp Ala Gly Asp Gly Phe Lys Glu Gly Val Ser Leu Thr Val
625                 630                 635                 640

Tyr Asp Glu Leu Ala Arg Trp Glu Lys Tyr Ala Phe Gly Cys Asn Glu
                645                 650                 655

Leu Leu Phe Asn Pro Ile Arg Thr Trp Leu Trp Arg Gly Pro Phe Thr
                660                 665                 670

Pro Leu Phe Arg Arg Phe Cys Phe Ser Asn Ile Arg Phe Thr Ser Lys
                675                 680                 685

Ile Thr Val Val Ser Tyr Ile Gly Thr Tyr Ala Ile Gly Ala Ala
    690                 695                 700

Trp Ile Met Thr Thr Ala Asn Tyr Phe Leu Met Gly Trp Phe Asn Gly
705                 710                 715                 720

Tyr Leu Asp Lys Tyr Tyr Leu Asp Ser Trp Gln Val Trp Phe Ser Ile
                725                 730                 735

Ile Leu Val Phe Asn Gly Leu Gly Asn Leu Ala Leu Ala Ile Met Arg
                740                 745                 750

Tyr Arg Ser Gly Glu Arg Thr Leu Gly Tyr Ala Ile Tyr Glu Asn Phe
                755                 760                 765

Lys Trp Thr Leu Met Leu Ala Val Phe Leu Gly Gly Leu Ser Leu His
    770                 775                 780

Val Ser Gln Ala Leu Leu Ala His Met Phe Glu Ile Asp Met Ser Trp
785                 790                 795                 800

Gly Ser Thr Ser Lys Glu Ala Glu Phe Ser Asn Phe Phe Ile Glu Val
                805                 810                 815

Pro Lys Val Leu Lys Lys Phe Arg Val Ser Met Thr Leu Ser Leu Leu
                820                 825                 830

Ala Ile Val Ala Leu Ile Ile Met Ala Thr Ala Asp Phe Ile Pro His
                835                 840                 845

Tyr Trp Arg Ile Asn Asp Phe Val Ala Ile Leu Pro Met Ala Thr Val
    850                 855                 860

Ala Gly Ser His Leu Leu Leu Pro Leu Ala Leu Asn Pro Ala Leu Met
865                 870                 875                 880

Thr Phe Ser Trp

<210> SEQ ID NO 15
<211> LENGTH: 885
<212> TYPE: PRT
<213> ORGANISM: Myceliophthora thermophila

<400> SEQUENCE: 15

Met Gly Ile Gly Asp Tyr Phe Lys Ala Glu Lys Leu Gly Ser Lys Pro
1               5                   10                  15

Thr Pro Thr Pro Ala Ser Pro Pro Arg Glu His Gly Arg His Gln Gln
                20                  25                  30

Gln Pro Ser Ala Ser Glu Asp His Pro Ala Pro Ser Val Gln Pro Ala
            35                  40                  45

Ser Glu Leu Gln Pro Pro Thr Pro Arg Phe Ser Arg Pro Gln Ser
    50                  55                  60

Ile Ser Gly Arg Ser Val Arg Ser Thr Gly Ser Ser Val Leu Asp Glu
65                  70                  75                  80

Ile Lys His Glu Val Met Val Asn Tyr Leu Tyr Gln Gln Gln Cys Ser
                85                  90                  95
```

-continued

His Leu Trp Ile Ser Asp Gly Ser Gly Glu Ile Glu Gly Val Leu Leu
            100                 105                 110

Arg Lys Ala Arg Gly Gln Tyr Met Ala Cys Pro Pro Gln Leu Val Asn
            115                 120                 125

Ser Pro Leu Ala Ala Ala Cys Thr Ala Leu Asn Val Gln Cys Ala Met
130                     135                 140

Thr Val Asn Ser Arg Val Ile Lys Thr Phe Leu Gln Trp Ser Pro Asp
145                 150                 155                 160

Ala Val Asp Val Pro Leu Met Asn Gly Met Arg Val Gln Ile Leu Ala
                165                 170                 175

Thr Ile Asp Asp Leu Pro Arg Ala Arg Lys His Gln Phe Ala Ala Phe
            180                 185                 190

Val Ala Ser Glu Gly Leu Leu Ile Val Trp Asp Asp Ala Leu His
            195                 200                 205

Leu Val Gln Arg Ala Lys Ala Ile Glu Ser Glu Leu Met Glu Leu Val
            210                 215                 220

Trp Lys Val Gly Ala Glu Asp Asn Glu Asp Glu Lys Gly Val Ala Ala
225                 230                 235                 240

Val Glu Glu Pro Glu Val Asp Glu Glu Ser Gly Glu Leu Lys Pro Glu
                245                 250                 255

Lys Arg Pro Val His Leu Leu Asn Ala Tyr Leu Val Ser Leu Ser Leu
                260                 265                 270

Ile Leu Val Thr Val Ser Leu Gly Ala Ala Phe Arg Gln Leu Ala Ile
            275                 280                 285

Glu Val Ser Val Asp Gly Asn Tyr Val Arg Leu Ala Leu Val Ala Leu
            290                 295                 300

Phe Pro Val Gln Met Phe Phe Thr Leu Phe Phe Ala Gln Val Ile Val
305                 310                 315                 320

Gly Cys Leu Ala Gln Ile Phe Gly Pro Ile Arg Gln Leu Thr Val Asn
                325                 330                 335

Ser Lys Phe Tyr Ser Ala Arg Pro Pro Arg Leu Arg Ser Ser Val
                340                 345                 350

Leu Pro His Val Thr Val Gln Cys Pro Val Tyr Lys Glu Gly Leu Asn
            355                 360                 365

Ala Val Ile Ala Pro Thr Val Lys Ser Ile Lys Gln Ala Met Ser Thr
370                 375                 380

Tyr Glu Leu Gln Gly Gly Ser Ala Asn Met Phe Ile Asn Asp Asp Gly
385                 390                 395                 400

Leu Gln Leu Ile Ser Glu Glu Asp Arg Arg Ala Arg Ile Glu Phe Tyr
                405                 410                 415

Ala Asp Asn Ser Ile Gly Trp Val Ala Arg Pro Lys His Gly Glu Asn
            420                 425                 430

Gly Phe Gln Arg Arg Gly Lys Phe Lys Lys Ala Ser Asn Met Asn Phe
            435                 440                 445

Ala Leu Met Ile Ser Cys Lys Val Glu Asp Lys Leu Ala Ala Ile Gln
450                 455                 460

Arg Thr Pro Asp Trp Thr Gln His Asp Glu Ala Leu Ala Tyr Glu Arg
465                 470                 475                 480

Ala Leu Lys Glu Val Leu Glu Glu Asp Gly Arg Ala Trp Ala Asp Gly
                485                 490                 495

Asn Ile Arg Ile Gly Asp Tyr Ile Leu Leu Val Asp Ser Asp Thr Arg
            500                 505                 510

```
Val Pro Ala Asp Cys Leu Leu Asp Ala Val Ser Glu Met Glu Leu Ser
            515                 520                 525

Pro Asp Val Gly Ile Met Gln Phe Ser Ser Gly Val Met Gln Val Val
530                 535                 540

His Thr Tyr Phe Glu Asn Gly Ile Thr Phe Phe Thr Asn Leu Ile Tyr
545                 550                 555                 560

Ser Ala Ile Arg Tyr Thr Val Ser Asn Gly Asp Val Ala Pro Phe Val
                565                 570                 575

Gly His Asn Ala Ile Leu Arg Trp Ser Ala Ile Gln Gln Val Ser Tyr
            580                 585                 590

Glu Asp Glu Asp Gly Tyr Glu Lys Phe Trp Ser Glu Ser His Val Ser
        595                 600                 605

Glu Asp Phe Asp Met Ser Leu Arg Leu Gln Cys Ala Gly Tyr Ile Ile
    610                 615                 620

Arg Leu Ala Ala Trp Ala Gly Asp Gly Phe Lys Glu Gly Val Ser Leu
625                 630                 635                 640

Thr Val Tyr Asp Glu Leu Ala Arg Trp Glu Lys Tyr Ala Tyr Gly Cys
                645                 650                 655

Asn Glu Leu Leu Phe His Pro Ile Arg Lys Trp Ile Tyr Lys Gly Pro
            660                 665                 670

Phe Thr Pro Leu Phe Arg Arg Phe Leu Phe Ser Asn Ile Arg Phe Thr
        675                 680                 685

Ser Lys Val Thr Val Ile Ser Tyr Ile Gly Thr Tyr Tyr Ala Ile Ala
    690                 695                 700

Ala Ala Trp Ile Met Thr Ser Ile Asn Tyr Phe Ile Met Gly Trp Phe
705                 710                 715                 720

Asn Gly Tyr Leu Asp Lys Tyr Tyr Val Asp Ser Trp Gln Val Trp Phe
                725                 730                 735

Ser Ile Ile Leu Val Phe Asn Gly Leu Gly Asn Ile Ala Leu Ala Val
            740                 745                 750

Met Arg Tyr Arg Val Gly Glu Arg Ser Ile Leu Tyr Ala Leu Tyr Glu
        755                 760                 765

Asn Phe Lys Trp Thr Phe Leu Leu Ala Val Phe Leu Gly Gly Leu Ser
    770                 775                 780

Leu His Leu Ser Gln Ala Leu Leu Ala His Met Phe Glu Ile Asp Met
785                 790                 795                 800

Thr Trp Gly Ala Thr Ala Lys Glu Ala Glu Phe Ser Asn Phe Phe Ile
                805                 810                 815

Glu Val Pro Lys Val Leu Lys Lys Phe Lys Ile Ser Met Leu Phe Ala
            820                 825                 830

Thr Ile Phe Ile Ala Gly Met Ile Ile Leu Ala Val Ala Pro Phe Ile
        835                 840                 845

Pro Tyr Ser Trp His Ile Lys Asp Phe Val Ala Ile Leu Pro Met Ala
    850                 855                 860

Thr Val Ala Ala Ser His Leu Leu Leu Pro Leu Val Leu Asn Pro Ala
865                 870                 875                 880

Leu Met Thr Phe Ser
                885

<210> SEQ ID NO 16
<211> LENGTH: 880
<212> TYPE: PRT
<213> ORGANISM: Neurospora crassa
```

```
<400> SEQUENCE: 16

Met Gly Ile Gly Ser Tyr Phe Lys Ala Lys Lys Pro Glu Pro Ala Gly
1               5                   10                  15

Gln Gln His Ala Ala Ser Thr Pro Ser Arg Gly Arg Gln Pro Ser Met
            20                  25                  30

Gly Asn Thr Lys Ala Gly Gln Asp Asp Gly Asp Ile Leu Ala Pro Pro
        35                  40                  45

Gln Ile Arg Tyr Gly Ser Arg Ser Arg Ser Ala Thr Arg Ser Met Met
    50                  55                  60

Ser Ser Thr Ser Ser Val Ile Leu Glu Asp Ile Lys His Glu Val Met
65                  70                  75                  80

Val Asn Tyr Leu Tyr Gln Gln Cys Ser Tyr Leu Trp Val Ala Asn
                85                  90                  95

Gly Ser Gly Glu Ile Glu Gly Val Leu Leu Arg Lys Ser Arg Gly Gln
                100                 105                 110

Tyr Met Ala Cys Pro Pro Ala Leu Gly Asn Ser Pro Phe Ala Met Ala
            115                 120                 125

Cys Ala Ala Leu Asn Val Gln Cys Ala Met Thr Val Asn Ser Arg Val
            130                 135                 140

Ile Lys Thr Phe Leu Gln Trp Ser Pro Asp Ala Val Asp Val Pro Leu
145                 150                 155                 160

Leu Asn Gly Leu Arg Val Gln Ile Leu Pro Thr Ile Glu Asp Leu Pro
                165                 170                 175

Arg Ala Arg Lys His Gln Phe Ala Ala Phe Ile Ala Ser Glu Gly Leu
            180                 185                 190

Leu Val Val Trp Asp Asp Ala Leu His Leu Ile Pro Arg Ala Lys
            195                 200                 205

Glu Ile Glu Ser Glu Leu Met Gln Leu Val Trp Lys Thr Gly Glu Pro
210                 215                 220

Gly Glu Met Asp Glu Lys Ala Asn Pro Ile Val Gly Ala Thr Glu Ile
225                 230                 235                 240

Asp Glu Glu Ser Gly Glu Pro Arg Pro Glu Ala Arg Pro Val His Leu
            245                 250                 255

Leu Asn Thr Tyr Leu Val Ser Ile Thr Met Ala Val Val Thr Val Ser
            260                 265                 270

Leu Gly Ala Ala Trp Arg Gln Leu Ala Ile Glu Val Met Val Asp Gly
            275                 280                 285

Asp Tyr Val Arg Leu Ala Leu Val Ala Leu Ala Pro Val Gln Ile Phe
            290                 295                 300

Phe Thr Leu Phe Phe Ala Gln Val Ile Ile Gly Cys Leu Ala Gln Ile
305                 310                 315                 320

Phe Gly Pro Ile Lys Gln Leu Ser Val Asn Ser Arg Phe Tyr Ser Ala
                325                 330                 335

Lys Pro Pro Arg Leu Gln Thr Ala Val Leu Pro His Val Thr Val
            340                 345                 350

Gln Cys Pro Val Tyr Lys Glu Gly Leu Ser Gly Val Ile Ala Pro Thr
            355                 360                 365

Val Lys Ser Ile Lys His Ala Met Ser Thr Tyr Glu Leu Gln Gly Gly
            370                 375                 380

Ser Ala Asn Met Phe Ile Asn Asp Asp Gly Leu Gln Leu Leu Ser Glu
385                 390                 395                 400

Glu Asp Arg Gln Ala Arg Ile Asp Phe Tyr Ala Asp His Ser Ile Gly
                405                 410                 415
```

```
Trp Val Ala Arg Pro Arg His Gly Glu Asn Gly Phe Gln Arg Arg Gly
            420                 425                 430

Lys Phe Lys Lys Ala Ser Asn Met Asn Tyr Ala Leu Met Ile Ser Cys
            435                 440                 445

Lys Val Glu Glu Lys Leu Ala Gln Val Pro Arg His Ser Glu Trp Ser
            450                 455                 460

Gln His Asp Glu Ala Gln Ala Tyr Glu Arg Ala Leu Lys Asp Val Leu
465                 470                 475                 480

Glu Glu Asn Gly Arg Ala Trp Ala Asp Gly Asn Ile Arg Met Gly Asp
            485                 490                 495

Tyr Ile Leu Leu Ile Asp Ser Asp Thr Arg Val Pro Ser Asp Cys Leu
            500                 505                 510

Leu Asp Ala Val Ser Glu Met Glu Gln Ser Pro Asp Val Gly Ile Met
            515                 520                 525

Gln Phe Ser Ser Gly Val Met Gln Val Val His Thr Tyr Phe Glu Asn
530                 535                 540

Gly Ile Thr Phe Phe Thr Asn Leu Ile Tyr Thr Ala Ile Arg Tyr Thr
545                 550                 555                 560

Val Ser Asn Gly Asp Val Ala Pro Phe Val Gly His Asn Ala Ile Leu
            565                 570                 575

Arg Trp Ser Ala Ile Gln Gln Val Ser Tyr Glu Asp Glu Asp Gly Tyr
            580                 585                 590

Glu Lys Phe Trp Ser Glu Ser His Val Ser Glu Asp Phe Asp Met Ser
            595                 600                 605

Leu Arg Leu Gln Cys Asn Asp Tyr Ile Ile Arg Leu Ala Ala Trp Ala
            610                 615                 620

Gly Asp Gly Phe Lys Glu Gly Val Ser Leu Thr Val Tyr Asp Glu Leu
625                 630                 635                 640

Ala Arg Trp Glu Lys Tyr Ala Tyr Gly Cys Asn Glu Leu Leu Phe Tyr
            645                 650                 655

Pro Ile Arg Lys Trp Ile Trp Lys Gly Pro Phe Thr Pro Leu Phe Arg
            660                 665                 670

Arg Phe Leu Phe Ser Asn Ile Arg Phe Thr Ser Lys Ile Thr Ile Ile
            675                 680                 685

Ser Tyr Ile Gly Thr Tyr Ala Ile Gly Ala Ala Trp Ile Leu Thr
            690                 695                 700

Ser Val Asn Tyr Phe Leu Met Gly Trp Tyr Asn Gly Phe Leu Asp Lys
705                 710                 715                 720

Tyr Tyr Val Asp Ser Trp Gln Val Trp Phe Ser Ile Ile Leu Val Phe
            725                 730                 735

Asn Gly Leu Gly Asn Val Ala Leu Ala Val Met Arg Tyr Arg Val Gly
            740                 745                 750

Glu Arg Ser Ile Leu Gly Ser Ile Leu Glu Asn Phe Lys Trp Thr Leu
            755                 760                 765

Met Leu Ala Ile Phe Leu Gly Leu Ser Leu His Val Ser Gln Ala
            770                 775                 780

Leu Leu Ala His Met Phe Glu Ile Asp Met Thr Trp Gly Ala Thr Ser
785                 790                 795                 800

Lys Glu Ala Glu Phe Ser Asn Phe Phe Ile Glu Val Pro Lys Val Leu
            805                 810                 815

Lys Lys Phe Lys Phe Ser Met Leu Phe Ser Ile Gly Phe Ile Ile Gly
            820                 825                 830
```

```
Met Val Ile Leu Ala Thr Ala Pro Phe Ile Pro His Ser Trp His Ile
835                 840                 845

Thr Asp Phe Val Ala Ile Leu Pro Met Ala Thr Val Ala Ala Ser His
850                 855                 860

Leu Leu Leu Pro Leu Ala Leu Asn Pro Ala Leu Met Thr Phe Ser Trp
865                 870                 875                 880

<210> SEQ ID NO 17
<211> LENGTH: 939
<212> TYPE: PRT
<213> ORGANISM: Candida intermedia

<400> SEQUENCE: 17

Met Gly Ile Thr Asp Tyr Phe Val Ser Lys Gly Ala Thr Glu Ala Lys
1               5                   10                  15

Gln Gly Lys Asn Ser Thr Asp Ile Gln Gln Asn Glu Thr Leu Thr Phe
            20                  25                  30

Pro Glu Met Leu Ala Gly Pro Thr Gly Ala Ser Pro Arg Ala Gln Phe
        35                  40                  45

Thr Ile Gly Glu Thr His Leu Ser Ser Asp Ile Arg Thr Leu Gln Gly
    50                  55                  60

His Asn Glu Met Ile Ser Ala Gly Lys Ser Asp Phe Lys Asp Pro Gln
65                  70                  75                  80

Phe Ile Val Val Asn Tyr Leu His Asp Ile Cys Leu Gly Asn Gly Trp
                85                  90                  95

Leu Lys Leu Val Asp Pro Leu Glu Pro Cys Val Val Lys Met Asn Ser
            100                 105                 110

Lys Lys Gly Asn Glu Ile Gly Tyr Arg Tyr Leu Pro Ala Cys Asp Glu
        115                 120                 125

Ile Ala Pro Tyr Ser Phe Val Asp Cys Ala Ala Arg Phe Leu Arg Ser
    130                 135                 140

Asp Val Cys Val Arg Val Ser Phe Pro Val Ile His Ala Ile Leu Asp
145                 150                 155                 160

Ile Leu Ser Ser Lys Gly Thr Val Ser Leu Asp Ala Asp His Asn Ile
                165                 170                 175

Gln Ile Ile Glu Thr Val Ala Asp Leu Gln Trp Val Arg Lys Ser Gln
            180                 185                 190

Asn Cys Ala Phe Ile Arg Asn Glu Lys Ser Leu Val Cys Trp Ala Asp
        195                 200                 205

Ser Val Gln Glu Val Thr Gly Phe Val Arg Asn Leu Glu Asn Lys Met
    210                 215                 220

Val Asp Tyr Val Trp Lys Lys Gly Asn Ala Val Asp Val Lys Gly Glu
225                 230                 235                 240

Asp Tyr Val Pro Arg Val Thr Phe Ala Ser Val Phe Gln Ser Ser Ser
                245                 250                 255

Glu Ser Asp Val Gly Ser Glu Gly Ala Val Glu Ile Ile Gly Gln Asn
            260                 265                 270

Ala Val Ser Gln Val Ser Ile Ser Glu Lys Ser Ser Asp Ser Ser Thr
        275                 280                 285

His Ser Asp Gly Asn Leu Asn Glu Lys Lys Asn Leu Asp Leu Glu Gln
    290                 295                 300

Gln Ser Ser Glu Arg Pro Val Ile Tyr Ile His Ala Thr Val Ser Ala
305                 310                 315                 320

Phe Ala Ile Thr Leu Val Leu Ala Trp Ala Gly Leu Gln Phe Ala Gln
                325                 330                 335
```

```
Val Thr Lys Glu Ile Arg Ala Glu Gly Asn Tyr Leu Ile Leu Leu Ser
            340                 345                 350

Leu Leu Met Val Leu Pro Tyr Phe Leu Phe Thr Ser Phe Ala Ser
            355                 360                 365

Ser Val Met Ser Thr Leu Leu Tyr Val Phe Gly Pro Ile Ser Gln Met
            370                 375                 380

Asn Lys Asn Ser Tyr Ser Tyr Ser Val His Lys Ala Pro Arg Leu Lys
385                 390                 395                 400

Ala Ala His Gly Ser Leu Pro His Val Thr Ile Gln Cys Pro Val Tyr
                405                 410                 415

Lys Glu Lys Leu Glu Ser Val Ile Lys Pro Thr Ile Lys Ser Leu Gln
            420                 425                 430

Ala Ala Ile Arg Thr Tyr Glu Leu Gln Gly Gly Ser Ala Asn Ile Phe
            435                 440                 445

Ile Asn Asp Asp Gly Leu Gln Leu Ile Asp Arg Lys Glu Ala Leu Glu
450                 455                 460

Arg Ile Glu Tyr Tyr Glu Glu Cys Gly Leu Gly Tyr Val Ala Arg Pro
465                 470                 475                 480

Gly His Gly Val Asn Gly Phe Ile Arg Lys Gly Arg Phe Lys Lys Ala
                485                 490                 495

Ser Asn Met Asn Tyr Cys Leu His Ile Ser Lys Leu Val Asp Thr Arg
            500                 505                 510

Phe His Glu Arg Leu Glu Leu Ile Glu Asn Pro Thr Pro Lys Glu Glu
            515                 520                 525

Ser Gly Leu Tyr Leu Lys Val Leu Glu Glu Val Val Arg Glu Glu Gly
            530                 535                 540

Lys Cys Trp Ala Gly Gly Asp Ile Leu Leu Gly Asp Ile Ile Leu Ile
545                 550                 555                 560

Ile Asp Ser Asp Thr Arg Val Pro Glu Asp Cys Phe Val Asp Ser Val
                565                 570                 575

Ser Glu Met Glu Gln Ser Pro Glu Val Ala Ile Ile Gln His Ala Ser
            580                 585                 590

Gly Val Met Met Val Val Gly Asn Tyr Trp Glu Lys Met Ile Ala Trp
            595                 600                 605

Phe Thr Asn Met Ile Tyr Phe Ser Ile Ser Cys Val Ser Gly Asn Gly
            610                 615                 620

Leu Thr Met Ala Ala Phe Val Gly His Asn Ala Phe Leu Arg Trp Ser
625                 630                 635                 640

Ala Ile Gln Glu Leu Ala Tyr Ile Asp Glu Asp Gly Arg Thr Lys
                645                 650                 655

Tyr Trp Ser Glu Ser His Val Ser Glu Asp Phe Glu Met Thr Leu Lys
            660                 665                 670

Leu Ala Ser Leu Gly Tyr Thr Ile Arg Ile Ala Thr Tyr His Asp Gly
            675                 680                 685

Gly Phe Lys Glu Gly Val Ser Leu Thr Val Tyr Asp Glu Ile Thr Arg
            690                 695                 700

Trp Ser Lys Tyr Ala Phe Gly Cys Ala Glu Ile Met Phe Ser Pro Phe
705                 710                 715                 720

Lys Asp Trp Trp Lys Gly Lys Ile Phe Ala Arg Leu Phe Phe Val Phe
                725                 730                 735

Leu Asn Ser His Ile Ser Leu Pro Cys Lys Phe Ser Ile Leu Gly Tyr
            740                 745                 750
```

```
Met Gly Thr Tyr Tyr Ala Ile Ala Thr Ser Leu Ile Met Leu Val Ala
            755                 760                 765

Asn Tyr Phe Ile Val Gly Tyr Tyr Asp Trp Gly Tyr Ser Arg Val Tyr
    770                 775                 780

Ile Asp Ala Met Lys Val Phe Val Ser Val Met Val Val Phe Gly Cys
785                 790                 795                 800

Ala Thr Gln Val Ala Tyr Ile Ile Gly Arg Tyr Arg Ile Tyr Lys His
            805                 810                 815

Ser Ile Tyr Thr Met Val Leu Glu Phe Arg Tyr Ser Ile Leu Phe Ser
            820                 825                 830

Val Phe Leu Gly Gly Leu Ser Trp His Met Ile Val Ser Ile Gly Ser
            835                 840                 845

Tyr Phe Phe Ser Leu Asn Leu Gln Trp Gly Ala Thr Ala Lys Asp Ile
            850                 855                 860

Asp Asp Ser Asn Phe Phe Lys Glu Leu Pro Lys Ala Ile Lys Asn Tyr
865                 870                 875                 880

Lys Phe Met Tyr Ile Leu Cys Ile Phe Leu Ile Ala Gly Met Ile Val
            885                 890                 895

Leu Ala Phe Phe Val Pro Tyr Ala Phe Gln Ile Arg Leu Leu Thr Cys
            900                 905                 910

Ala Leu Pro Leu Gly Trp Ser Val Ala Ser His Phe Leu Ser Pro Ile
            915                 920                 925

Val Leu Asn Pro Gln Leu Met Thr Phe Ala Trp
            930                 935

<210> SEQ ID NO 18
<211> LENGTH: 395
<212> TYPE: PRT
<213> ORGANISM: Hypocrea jecorina

<400> SEQUENCE: 18

Ala Trp Ala Asp Gly Asn Ile Arg Met Gly Asp Tyr Ile Leu Leu Ile
1               5                   10                  15

Asp Ser Asp Thr Arg Val Pro Ala Asp Cys Leu Leu Asp Ala Val Ser
            20                  25                  30

Glu Met Glu Gln Ser Pro Asp Val Gly Ile Met Gln Phe Ser Ser Gly
        35                  40                  45

Val Met Gln Val Val His Thr Tyr Phe Glu Asn Gly Ile Thr Phe Phe
    50                  55                  60

Thr Asn Leu Ile Tyr Ser Ala Ile Arg Tyr Thr Val Ser Asn Gly Asp
65                  70                  75                  80

Val Ala Pro Phe Val Gly His Asn Ala Ile Leu Arg Trp Ser Ala Ile
            85                  90                  95

Gln Gln Val Ala Tyr Gln Asp Glu Asp Gly Tyr Asp Lys Phe Trp Ser
            100                 105                 110

Glu Ser His Val Ser Glu Asp Phe Asp Met Ser Leu Arg Leu Gln Cys
        115                 120                 125

Asn Gly Tyr Ile Ile Arg Leu Ala Ala Trp Ala Gly Glu Gly Phe Lys
    130                 135                 140

Glu Gly Val Ser Leu Thr Val Tyr Asp Glu Leu Ala Arg Trp Glu Lys
145                 150                 155                 160

Tyr Ala Tyr Gly Cys Asn Glu Leu Leu Phe His Pro Ile Arg Thr Trp
            165                 170                 175

Leu Trp Arg Gly Pro Phe Thr Pro Leu Phe Arg Arg Phe Leu Phe Ser
            180                 185                 190
```

```
Asn Ile Arg Phe Thr Ser Lys Val Thr Val Ile Ser Tyr Ile Gly Thr
            195                 200                 205

Tyr Tyr Ala Ile Gly Ala Ala Trp Ile Leu Thr Ala Val Asn Tyr Phe
    210                 215                 220

Val Met Gly Trp Phe Asn Gly Tyr Leu Asp Lys Tyr Tyr Val Asp Ser
225                 230                 235                 240

Trp Gln Val Trp Phe Ser Ile Ile Val Phe Asn Gly Leu Gly Asn
                245                 250                 255

Ile Ala Leu Ala Val Met Arg Tyr Arg Val Gly Glu Arg Gly Leu Leu
                260                 265                 270

Tyr Ala Leu Phe Glu Asn Phe Met Trp Thr Leu Met Leu Ala Ile Phe
            275                 280                 285

Leu Gly Gly Leu Ser Leu His Val Ser Gln Ala Leu Leu Ala His Met
290                 295                 300

Phe Glu Ile Asn Met Thr Trp Gly Ala Thr Ser Lys Glu Ala Glu Phe
305                 310                 315                 320

Ser Asn Phe Phe Ile Glu Val Pro Lys Val Leu Lys Lys Phe Lys Phe
                325                 330                 335

Ser Met Leu Phe Ser Leu Ile Phe Ile Ala Gly Met Ile Ile Leu Ala
            340                 345                 350

Gln Ala Pro Phe Val Pro Phe Asp Trp Arg Ile Lys Asp Phe Val Ala
            355                 360                 365

Ile Leu Pro Met Ala Thr Val Ala Ser His Phe Leu Leu Pro Leu
            370                 375                 380

Ala Leu Asn Pro Ala Leu Met Thr Phe Ser Trp
385                 390                 395

<210> SEQ ID NO 19
<211> LENGTH: 1343
<212> TYPE: PRT
<213> ORGANISM: Hypocrea jecorina

<400> SEQUENCE: 19

Met Ile Glu Asp Thr Ala Ala Leu Ala Ala Ala Glu Leu Ile Ala
1               5                   10                  15

Ser Leu Ala Cys Asp Pro Ala Ser Ala Ser Ser Ser Leu Val
            20                  25                  30

Ser Val Gly Pro Gly Ser Ser Ile Lys Leu Pro Gly Arg Glu Asn Pro
            35                  40                  45

Ala Lys Arg Thr Leu Glu Ile Glu Leu Glu Lys Leu Val Leu Arg Ile
    50                  55                  60

Ser Gln Leu Glu Ser Arg Ala Ser Ala Ser Asn Ala Ser Val Phe
65                  70                  75                  80

Pro Glu Thr Pro Asn Glu Val Asn Asp Thr Leu Phe Asn Asp Val
                85                  90                  95

Asp Pro Ser Val Asn Gly Arg Pro Val Ala Pro Gln Pro Arg Leu
            100                 105                 110

Ser Gln Ala Gln Gln Gly Ser Leu Asp Ser Pro Ile Phe Val Ser Arg
            115                 120                 125

Gln Leu Thr Lys Glu Ala Leu Gln Gly Leu Arg Asp His Val Asp Asp
    130                 135                 140

Gln Ser Lys Leu Leu Asp Ser Gln Arg Gln Glu Leu Ala Gly Val Asn
145                 150                 155                 160
```

```
Ala Gln Leu Leu Glu Gln Lys Gln Leu Gln Glu Arg Ala Leu Ala Met
                165                 170                 175

Leu Glu Gln Glu Arg Val Ala Thr Leu Glu Arg Glu Leu Trp Lys His
            180                 185                 190

Gln Lys Ala Asn Glu Ala Phe Gln Lys Ala Leu Arg Glu Ile Gly Glu
        195                 200                 205

Ile Val Thr Ala Val Ala Arg Gly Asp Leu Thr Met Lys Val Arg Met
    210                 215                 220

Asn Ser Val Glu Met Asp Pro Glu Ile Thr Thr Phe Lys Arg Thr Ile
225                 230                 235                 240

Asn Ala Met Met Asp Gln Leu Gln Thr Phe Ala Ser Glu Val Ser Arg
                245                 250                 255

Val Ala Arg Glu Val Gly Thr Glu Gly Leu Leu Gly Gly Gln Ala Arg
            260                 265                 270

Ile Gly Gly Val Asp Gly Val Trp Lys Glu Leu Thr Asp Asn Val Asn
        275                 280                 285

Ile Met Ala Gln Asn Leu Thr Asp Gln Val Arg Glu Ile Ala Ser Val
    290                 295                 300

Thr Thr Ala Val Ala His Gly Asp Leu Thr Lys Lys Ile Glu Arg Pro
305                 310                 315                 320

Ala Lys Gly Glu Ile Leu Gln Leu Gln Gln Thr Ile Asn Thr Met Val
                325                 330                 335

Asp Gln Leu Arg Thr Phe Ala Ser Glu Val Thr Arg Val Ala Arg Asp
            340                 345                 350

Val Gly Thr Glu Gly Ile Leu Gly Gly Gln Ala Asp Val Gly Gly Val
        355                 360                 365

Lys Gly Met Trp Asn Asp Leu Thr Val Asn Val Asn Ala Met Ala Asn
    370                 375                 380

Asn Leu Thr Thr Gln Val Arg Asp Ile Ile Lys Val Thr Thr Ala Val
385                 390                 395                 400

Ala Lys Gly Asp Leu Thr Gln Lys Val Gln Ala Glu Cys Arg Gly Glu
                405                 410                 415

Met Phe Lys Leu Lys Ser Thr Ile Asn Ser Met Val Asp Gln Leu Gln
            420                 425                 430

Gln Phe Ala Arg Glu Val Thr Lys Ile Ala Arg Glu Val Gly Thr Glu
        435                 440                 445

Gly Arg Leu Gly Gly Gln Ala Thr Val His Asp Val Glu Gly Thr Trp
    450                 455                 460

Arg Asp Leu Thr Glu Asn Val Asn Gly Met Ala Met Asn Leu Thr Thr
465                 470                 475                 480

Gln Val Arg Glu Ile Ala Lys Val Thr Thr Ala Val Ala Arg Gly Asp
                485                 490                 495

Leu Thr Lys Lys Ile Gly Val Glu Val Lys Gly Glu Ile Leu Glu Leu
            500                 505                 510

Lys Asn Thr Ile Asn Gln Met Val Asp Arg Leu Gly Thr Phe Ala Val
        515                 520                 525

Glu Val Ser Lys Val Ala Arg Glu Val Gly Thr Asp Gly Thr Leu Gly
    530                 535                 540

Gly Gln Ala Gln Val Ala Asn Val Glu Gly Lys Trp Lys Asp Leu Thr
545                 550                 555                 560

Glu Asn Val Asn Thr Met Ala Ser Asn Leu Thr Val Gln Val Arg Ser
                565                 570                 575
```

```
Ile Ser Ala Val Thr Gln Ala Ile Ala Asn Gly Asp Met Ser Gln Thr
            580                 585                 590

Ile Asp Val Glu Ala Asn Gly Glu Ile Gln Val Leu Lys Glu Thr Ile
            595                 600                 605

Asn Asn Met Val Ser Arg Leu Ser Ser Phe Cys Tyr Glu Val Gln Arg
    610                 615                 620

Val Ala Lys Asp Val Gly Val Asp Gly Lys Met Gly Ala Gln Ala Asp
625                 630                 635                 640

Val Ala Gly Leu Asn Gly Arg Trp Lys Glu Ile Thr Thr Asp Val Asn
            645                 650                 655

Thr Met Ala Ser Asn Leu Thr Thr Gln Val Arg Ala Phe Ser Asp Ile
        660                 665                 670

Thr Asn Leu Ala Thr Asp Gly Asp Phe Thr Lys Leu Val Asp Val Glu
        675                 680                 685

Ala Ser Gly Glu Met Asp Glu Leu Lys Lys Lys Ile Asn Gln Met Ile
        690                 695                 700

Ser Asn Leu Arg Asp Ser Ile Gln Arg Asn Thr Gln Ala Arg Glu Ala
705                 710                 715                 720

Ala Glu Leu Ala Asn Lys Thr Lys Ser Glu Phe Leu Ala Asn Met Ser
            725                 730                 735

His Glu Ile Arg Thr Pro Thr Asn Gly Ile Ile Gly Met Thr Gln Leu
            740                 745                 750

Thr Leu Asp Thr Asp Leu Thr Gln Tyr Gln Arg Glu Met Leu Asn Ile
        755                 760                 765

Val Asn Asp Leu Ala Asn Ser Leu Leu Thr Ile Ile Asp Asp Ile Leu
770                 775                 780

Asp Leu Ser Lys Ile Glu Ala Arg Arg Met Val Ile Glu Glu Ile Pro
785                 790                 795                 800

Tyr Thr Leu Arg Gly Thr Val Phe Asn Ala Leu Lys Thr Leu Ala Val
            805                 810                 815

Lys Ala Asn Glu Lys Phe Leu Asp Leu Thr Tyr Lys Val Asp Ser Ser
            820                 825                 830

Val Pro Asp Tyr Val Ile Gly Asp Ser Phe Arg Leu Arg Gln Ile Ile
        835                 840                 845

Leu Asn Leu Val Gly Asn Ala Ile Lys Phe Thr Glu His Gly Glu Val
850                 855                 860

Ser Leu Thr Ile Gln Glu Gln Glu Asp Lys Arg His Val Gly Pro Gly
865                 870                 875                 880

Glu Tyr Ala Ile Glu Phe Ile Val Glu Asp Thr Gly Ile Gly Ile Ala
            885                 890                 895

Lys Asp Lys Leu Asn Leu Ile Phe Asp Thr Phe Gln Gln Ala Asp Gly
            900                 905                 910

Ser Met Thr Arg Lys Phe Gly Gly Thr Gly Leu Gly Leu Ser Ile Ser
        915                 920                 925

Lys Arg Phe Val Asn Leu Met Gly Gly Asp Leu Trp Val Asn Ser Glu
        930                 935                 940

Val Gly Lys Gly Ser Glu Phe His Phe Thr Cys Arg Val Lys Leu Ala
945                 950                 955                 960

Asp Val His Ala Glu Ser Val Gln Gln Leu Lys Pro Tyr Arg Gly
            965                 970                 975

His Gln Val Leu Phe Val Asp Lys Ser Gln Ser Asn Ala Ala Thr His
            980                 985                 990
```

Ile Gly Glu Met Leu Glu Glu Ile Gly Leu His Pro Val Val Val Asn
    995                 1000                1005

Ser Glu Lys Ser Ser Ala Leu Thr Arg Leu Lys Glu Gly Gly Ala
    1010                1015                1020

Leu Pro Tyr Asp Ala Ile Ile Val Asp Ser Ile Asp Thr Ala Arg
    1025                1030                1035

Arg Leu Arg Ala Val Asp Asp Phe Lys Tyr Leu Pro Ile Val Leu
    1040                1045                1050

Leu Ala Pro Val Val His Val Ser Leu Lys Ser Cys Leu Asp Leu
    1055                1060                1065

Gly Ile Thr Ser Tyr Met Thr Met Pro Cys Lys Leu Ile Asp Leu
    1070                1075                1080

Ser Asn Gly Met Ile Pro Ala Leu Glu Asn Arg Ala Thr Pro Ser
    1085                1090                1095

Leu Ala Asp Val Thr Lys Ser Phe Glu Ile Leu Leu Ala Glu Asp
    1100                1105                1110

Asn Thr Val Asn Gln Lys Leu Ala Val Lys Ile Leu Glu Lys Tyr
    1115                1120                1125

His His Val Val Thr Val Val Gly Asn Gly Trp Glu Ala Val Glu
    1130                1135                1140

Ala Val Lys Gln Lys Lys Phe Asp Val Ile Leu Met Asp Val Gln
    1145                1150                1155

Met Pro Ile Met Gly Gly Phe Glu Ala Thr Gly Lys Ile Arg Glu
    1160                1165                1170

Tyr Glu Arg Gly Met Gly Thr His Arg Thr Pro Ile Ile Ala Leu
    1175                1180                1185

Thr Ala His Ala Met Met Gly Asp Arg Glu Lys Cys Ile Gln Ala
    1190                1195                1200

Gln Met Asp Glu Tyr Leu Ser Lys Pro Leu Gln Gln Asn Gln Leu
    1205                1210                1215

Ile Gln Thr Ile Leu Lys Cys Ala Thr Leu Gly Gly Ala Leu Leu
    1220                1225                1230

Glu Lys Asn Arg Glu Arg Glu Leu Ala Leu Gln Ala Glu Ala Lys
    1235                1240                1245

Ala Ser Gly Arg Leu Asp Gly Glu Arg Gly Met Leu Arg Pro Gly
    1250                1255                1260

Leu Glu Gly Arg Ser Phe Thr Thr Arg Glu Pro Met Thr Lys Ser
    1265                1270                1275

Arg Pro Ser Leu Thr Lys Ala Thr Ser Lys Ala Leu Glu Glu Ala
    1280                1285                1290

Arg Asn Ala Ala Ala Ala Asn Ala Gly Leu Arg Phe Ser Glu Leu
    1295                1300                1305

Thr Gly Phe Ser Ala Asp Leu Met Glu Glu Leu Asp Asn Met Glu
    1310                1315                1320

Asp Glu Asp Ser Phe Thr Lys Ala Arg Glu Asp Leu Ala Asp Arg
    1325                1330                1335

Arg Ser Leu Ser Ser
    1340

<210> SEQ ID NO 20
<211> LENGTH: 4067
<212> TYPE: DNA
<213> ORGANISM: Hypocrea jecorina

<400> SEQUENCE: 20

```
atgcagcaac cgccctcctt agttggcgac cgcagcatca ccggcctggg agacgcagcc    60
agccgaccaa atctctcttc atcctcgcct accgtcacca gcgcgccctc ggcaccgaca   120
tcgccaccgc cgcggccgcc aatatcgctg aatccccgt cgcgagagcc tcctggcgtc   180
gagcccgtgc tccgcatcac gccagtcccg cgctccgtct ttgcctctgt ccaccagccg   240
cgcaagtcgt cgctggtcca gacgtcgcac gtcctgccct cgcccaggac cgccgccgca   300
gctcaccatc accatcccgt ctcgcattcc gcctctggca gcagcggcag caacggcagt   360
ggaagcggca gtggcagcgg cagcggcaat ctgctgcgtc aaacgcatcg cgacaccgtg   420
cacccccccg tcaagcggcc atccaccccg tcgtcgcatc ccaccagggg cgccagcacc   480
ggagcatcgc cgcagcaggg cgccagctcc cgaaaccgct cgtcgacgtc gcccgtttcg   540
tccccggcga gtcgcacgcc tccttatgca tctcgtcagg cctcagtttc ccattcccgc   600
cagcagcaca accaccatca tcagcaccaa caccagcatt accactccca caccagctcg   660
actaccagtc gcgccagcat cgaggccgta gtcggtgccg tccccgatcc ctcaggtcac   720
cgagcgccgc cgaaaccccg tcgaccggat cgcaaccact ttggcgcgtc agatcgcagc   780
gcaactccca ccctgtcgca cttcatgagg gcagagtcga gcatgtccat gagacattac   840
gagagcggcc ccttacgctc catgtcgccg aaccctacg gaaccctgc cgccaccacg   900
acgtcgtcca ctgccagaat gccgcacgag cagagccacg atccctacgc cctcgcggc   960
cactctcgcg atcactcggg gaagagcagc agagacatgg gcaagcccg agctcagaag  1020
aatccctcac agaaggcgat gctctcccgt gccctgcaaa aggccaacac cgcagttcag  1080
ctcgacaatg ctcagaactt cgaaggcgct cgagaagcgt acgccgaggc ttgcgacttg  1140
ttgcagcagg tgcttgaccg aacaccggga gatgaggaca gcggaagct cgaagccatt  1200
gtaagtcacg gcggcaaccg gaatgtcgag cccgttgtct gtcattagta gatcacttgg  1260
aactgacaat ttcaatctgt agcaccaaac ttacaccagc cgcatcgatg agctggatca  1320
gttgggccct tggcaggttg agaccgtcaa ggctctgccg gcgcggccag agagcgagga  1380
gtacagcgcg tccatattca tacccccagga ttacgacatg ggccgatgaag ctcccaggat  1440
tgagacggca cgggtggtga gctacatcgc tggagacaac gcgtctccct ttgcagcagc  1500
gcccaaccag tggcagcagt cgggaggtca cacggcatct gaacggctgc agcccaaccg  1560
cggtctggaa ccgggtctgc tacagtcgtc cttctctcgg gccccgaggt cgcccaggcg  1620
gctgcagtcc accgatgatc ttcgcgcaca gcatcaggag ggccagtatg cgcctccccc  1680
actctcgcct cgctcgcagt cgccggtaaa gacgcatgac catgacgacg acatgtttgc  1740
cgaactgcca ccacacgagc cctatcagta ccagcaagag cacgaccatc aagaccacca  1800
tcaagactac catcaacatc accgccatca caaccaccac catcacgaac gacagcccag  1860
cgagactgtc ctatcctcat acgagctcca gggtcatgtg gatggaggaa tccaaaactc  1920
atggctagat ccaattgacg agtcgggagg ctcaacagcg tcgtctgtac actcacgcac  1980
ctcttcgctt ggctaccgtc gacgccatat ccggccgtg agcgggaaca ccgaggccga  2040
gtttgacacg cgcgctggacg ctgctatcga ggctgcctac gacgacgct acgagcccat  2100
ggactctgta gactatggga ccattgatgc tgggggggac aatagcatgg caggcgtatt  2160
gcacaaggtg gagatggcgc gcgaacgagc gagacagacg gagcaggaag cctatgacga  2220
gctggccaac ctccgacagg cgcactcaca gaatccgcag caccagcagg aggaggacag  2280
gtatactgcc gagggattct acgaggacga ctcgtctgaa gaggaggaga gactattgga  2340
```

```
cgagattaca cgcgactttg ccattgagga ctttaccatg gaaaacccga atggcacaca    2400
ggtgtcagct aggcagcagg atgcatggaa cgaggacgag acgaggccgg atttcatctc    2460
gggcgtccga tccttttctg ccctgtcgca gaggccaccc attcctcagg cctacgccgc    2520
caacgcctcg cagccagcag ccccccctcc gacatccgca ttgccagacc tgccaccagg    2580
acgccctggt caaaatccaa agcaactcaa gatcgagacg gcaaacattg tacaaaccca    2640
gaagtcggtc tatgacgacg acgaaatctc cccaagcacg caagagccgc cgcccgagac    2700
gctcgtccgg acggcgagcg cgcagcctgt aaggccaccg ataccgacag aaagcttccc    2760
atccgaactc agtgctcccg catcgccaac cgccaagaag aggcttctgg aaggagagaa    2820
tgtgctgaat gcctcgcctt ctatccacag gctacggaag aacttttcgt cttctagctt    2880
gaggagcatg aagaacagga acatgtccgt ctcacatttg gacgcagct cggatgcttc    2940 ccccggcacc cccctgaatg acccctttcaa caaggcacct gccgtgcccg tgcccgcgct    3000
gccgaccccc ttgctcgcgt cgttcaaaga tcatatggag gcagcggccg gtgttggctt    3060
ccacctgttt gacgacgagt ttcatgcagc ggcggctgcc ggccccccaaa gcccgcagag    3120 tcccagaagt cccgttgttg tctccatgga cgtccctgtg cctctggaac cctgtccaaa    3180
cgacttcatg ctgcgaccgt tttggctgat gcgatgccta taccagacac ttgtgcatcc    3240
caagggtggc tacatcagta cgaagctatt cgtgccgcga cgtctggc gggtcaaagg    3300 tgtcaagatc aagaacgtgg aggacaaaat tgccaactgc gacttttttga ctgcagccct    3360 gctgaagctg tccaaagtgg acactctgga tgcggatgcc gtgctggagg agatgcaagc    3420
cctcgagggc attctggagc agatacagcc ggtcctggcc cgaaagcttg aaacgaagt    3480 gggcgttcaa ggttccggtc tgctgttcaa agacgcctcg atgatggaag agaccccgg    3540 ttcagccgtg ccgcgatcag gaagtgtgtc tggcaaggcg tctgcgtttt cctggcgacg    3600
gcttcggcca agacgtcgg gcgtcgggct gggagggtcg tacagcagcc gcaacgccag    3660
tgctgagacg aaggaggcct caacgctggc aacggtgccc atgacgccga aaccgacaag    3720
ccgttcggcc aagcgagacg tgagccaggt tcagttcatc gggcccaatg cgagctacat    3780
gggctctctc gcgcgcttgt ttgacgctgc gcaggcagtt ggtaagcata ttgcgatacg    3840
cataccggtt acagtgacgg caagctaacg atgatgcaga tcaaattgca aggcaggtcg    3900 acgacccgg tttgcggctt gcggacaaga ctcaggtcgg cttggagctc tgcacccggc    3960
acgccgctga gttctttggc tttttacattt gccgattcgt cttggccgac ctcggcctgt    4020
tgctggacaa gttcctcaaa cgaggaagcg aatgggtcat gacatga              4067
```

<210> SEQ ID NO 21
<211> LENGTH: 1308
<212> TYPE: PRT
<213> ORGANISM: Hypocrea jecorina

<400> SEQUENCE: 21

```
Met Gln Gln Pro Pro Ser Leu Val Gly Asp Arg Ser Ile Thr Gly Leu
1               5                   10                  15

Gly Asp Ala Ala Ser Arg Pro Asn Leu Ser Ser Ser Pro Thr Val
            20                  25                  30

Thr Ser Ala Pro Ser Ala Pro Thr Ser Pro Pro Arg Pro Pro Ile
        35                  40                  45

Ser Leu Asn Pro Pro Ser Arg Glu Pro Pro Gly Val Glu Pro Val Leu
    50                  55                  60
```

```
Arg Ile Thr Pro Val Pro Arg Ser Val Phe Ala Ser Val His Gln Pro
 65                  70                  75                  80

Arg Lys Ser Ser Leu Val Gln Thr Ser His Val Leu Pro Ser Pro Arg
                 85                  90                  95

Thr Ala Ala Ala His His His His Pro Val Ser His Ser Ala Ser
            100                 105                 110

Gly Ser Ser Gly Ser Asn Gly Ser Gly Ser Gly Ser Gly Ser
            115                 120                 125

Gly Asn Leu Leu Arg Gln Thr His Arg Asp Thr Val His Pro Pro Val
130                 135                 140

Lys Arg Pro Ser Thr Pro Ser Ser His Pro Thr Arg Gly Ala Ser Thr
145                 150                 155                 160

Gly Ala Ser Pro Gln Gln Gly Ala Ser Ser Arg Asn Arg Ser Ser Thr
                165                 170                 175

Ser Pro Val Ser Ser Pro Ala Ser Arg Thr Pro Pro Tyr Ala Ser Arg
                180                 185                 190

Gln Ala Ser Val Ser His Ser Arg Gln Gln His Asn His His His Gln
                195                 200                 205

His Gln His Gln His Tyr His Ser His Thr Ser Ser Thr Thr Ser Arg
210                 215                 220

Ala Ser Ile Glu Ala Val Val Gly Ala Val Pro Asp Pro Ser Gly His
225                 230                 235                 240

Arg Ala Pro Pro Lys Pro Arg Arg Pro Asp Arg Asn His Phe Gly Ala
                245                 250                 255

Ser Asp Arg Ser Ala Thr Pro Thr Leu Ser His Phe Met Arg Ala Glu
                260                 265                 270

Ser Ser Met Ser Met Arg His Tyr Glu Ser Gly Pro Leu Arg Ser Met
                275                 280                 285

Ser Pro Asn Pro Tyr Gly Thr Pro Ala Ala Thr Thr Thr Ser Ser Thr
                290                 295                 300

Ala Arg Met Pro His Glu Gln Ser His Asp Pro Tyr Ala Pro Arg Gly
305                 310                 315                 320

His Ser Arg Asp His Ser Gly Lys Ser Ser Arg Asp Met Gly Lys Pro
                325                 330                 335

Arg Ala Gln Lys Asn Pro Ser Gln Lys Ala Met Leu Ser Arg Ala Leu
                340                 345                 350

Gln Lys Ala Asn Thr Ala Val Gln Leu Asp Asn Ala Gln Asn Phe Glu
                355                 360                 365

Gly Ala Arg Glu Ala Tyr Ala Glu Ala Cys Asp Leu Leu Gln Gln Val
370                 375                 380

Leu Asp Arg Thr Pro Gly Asp Glu Asp Lys Arg Lys Leu Glu Ala Ile
385                 390                 395                 400

His Gln Thr Tyr Thr Ser Arg Ile Asp Glu Leu Asp Gln Leu Gly Pro
                405                 410                 415

Trp Gln Val Glu Thr Val Lys Ala Leu Pro Ala Arg Pro Glu Ser Glu
                420                 425                 430

Glu Tyr Ser Ala Ser Ile Phe Ile Pro Gln Asp Tyr Asp Met Gly Asp
                435                 440                 445

Glu Ala Pro Arg Ile Glu Thr Ala Arg Val Val Ser Tyr Ile Ala Gly
                450                 455                 460

Asp Asn Ala Ser Pro Phe Ala Ala Pro Asn Gln Trp Gln Gln Ser
465                 470                 475                 480
```

```
Gly Gly His Thr Ala Ser Glu Arg Leu Gln Pro Asn Arg Gly Leu Glu
                485                 490                 495

Pro Gly Leu Leu Gln Ser Ser Phe Ser Arg Ala Pro Arg Ser Pro Arg
            500                 505                 510

Arg Leu Gln Ser Thr Asp Asp Leu Arg Ala Gln His Gln Glu Gly Gln
        515                 520                 525

Tyr Ala Pro Pro Pro Leu Ser Pro Arg Ser Gln Ser Pro Val Lys Thr
    530                 535                 540

His Asp His Asp Asp Asp Met Phe Ala Glu Leu Pro Pro His Glu Pro
545                 550                 555                 560

Tyr Gln Tyr Gln Gln Glu His Asp His Gln Asp His His Gln Asp Tyr
                565                 570                 575

His Gln His His Arg His His Asn His His His Glu Arg Gln Pro
            580                 585                 590

Ser Glu Thr Val Leu Ser Ser Tyr Glu Leu Gln Gly His Val Asp Gly
        595                 600                 605

Gly Ile Gln Asn Ser Trp Leu Asp Pro Ile Asp Glu Ser Gly Gly Ser
    610                 615                 620

Thr Ala Ser Ser Val His Ser Arg Thr Ser Ser Leu Gly Tyr Arg Arg
625                 630                 635                 640

Arg His Ile Arg Ala Val Ser Gly Asn Thr Glu Ala Glu Phe Asp Thr
                645                 650                 655

Ala Leu Asp Ala Ala Ile Glu Ala Ala Tyr Asp Asp Gly Tyr Glu Pro
            660                 665                 670

Met Asp Ser Val Asp Tyr Gly Thr Ile Asp Ala Gly Gly Asp Asn Ser
        675                 680                 685

Met Ala Gly Val Leu His Lys Val Glu Met Ala Arg Glu Arg Ala Arg
    690                 695                 700

Gln Thr Glu Gln Glu Ala Tyr Asp Glu Leu Ala Asn Leu Arg Gln Ala
705                 710                 715                 720

His Ser Gln Asn Pro Gln His Gln Gln Glu Glu Asp Arg Tyr Thr Ala
                725                 730                 735

Glu Gly Phe Tyr Glu Asp Asp Ser Ser Glu Glu Glu Glu Arg Leu Leu
            740                 745                 750

Asp Glu Ile Thr Arg Asp Phe Ala Ile Glu Asp Phe Thr Met Glu Asn
        755                 760                 765

Pro Asn Gly Thr Gln Val Ser Ala Arg Gln Asp Ala Trp Asn Glu
    770                 775                 780

Asp Glu Thr Arg Pro Asp Phe Ile Ser Gly Val Arg Ser Phe Ser Ala
785                 790                 795                 800

Leu Ser Gln Arg Pro Pro Ile Pro Gln Ala Tyr Ala Ala Asn Ala Ser
                805                 810                 815

Gln Pro Ala Ala Pro Pro Thr Ser Ala Leu Pro Asp Leu Pro Pro
            820                 825                 830

Gly Arg Pro Gly Gln Asn Pro Lys Gln Leu Lys Ile Glu Thr Ala Asn
        835                 840                 845

Ile Val Gln Thr Gln Lys Ser Val Tyr Asp Asp Glu Ile Ser Pro
    850                 855                 860

Ser Thr Gln Glu Pro Pro Glu Thr Leu Val Arg Thr Ala Ser Ala
865                 870                 875                 880

Gln Pro Val Arg Pro Ile Pro Thr Glu Ser Phe Pro Ser Glu Leu
                885                 890                 895
```

```
Ser Ala Pro Ala Ser Pro Thr Ala Lys Lys Arg Leu Leu Glu Gly Glu
            900                 905                 910

Asn Val Leu Asn Ala Ser Pro Ser Ile His Arg Leu Arg Lys Asn Phe
        915                 920                 925

Ser Ser Ser Ser Leu Arg Ser Met Lys Asn Arg Asn Met Ser Val Ser
    930                 935                 940

His Leu Asp Asp Ser Ser Asp Ala Ser Pro Gly Thr Pro Leu Asn Asp
945                 950                 955                 960

Pro Phe Asn Lys Ala Pro Ala Val Pro Val Pro Ala Leu Pro Thr Pro
                965                 970                 975

Leu Leu Ala Ser Phe Lys Asp His Met Glu Ala Ala Ala Gly Val Gly
            980                 985                 990

Phe His Leu Phe Asp Asp Glu Phe His Ala Ala Ala Ala Ala Gly Pro
        995                 1000                1005

Gln Ser Pro Gln Ser Pro Arg Ser Pro Val Val Ser Met Asp
    1010                1015                1020

Val Pro Val Pro Leu Glu Pro Cys Pro Asn Asp Phe Met Leu Arg
    1025                1030                1035

Pro Phe Trp Leu Met Arg Cys Leu Tyr Gln Thr Leu Val His Pro
    1040                1045                1050

Lys Gly Gly Tyr Ile Ser Thr Lys Leu Phe Val Pro Arg Asp Val
    1055                1060                1065

Trp Arg Val Lys Gly Val Lys Ile Lys Asn Val Glu Asp Lys Ile
    1070                1075                1080

Ala Asn Cys Asp Phe Leu Thr Ala Ala Leu Leu Lys Leu Ser Lys
    1085                1090                1095

Val Asp Thr Leu Asp Ala Asp Ala Val Leu Glu Glu Met Gln Ala
    1100                1105                1110

Leu Glu Gly Ile Leu Glu Gln Ile Gln Pro Val Leu Ala Arg Lys
    1115                1120                1125

Leu Gly Asn Glu Val Gly Val Gln Gly Ser Gly Leu Leu Phe Lys
    1130                1135                1140

Asp Ala Ser Met Met Glu Gly Asp Pro Gly Ser Ala Val Pro Arg
    1145                1150                1155

Ser Gly Ser Val Ser Gly Lys Ala Ser Ala Phe Ser Trp Arg Arg
    1160                1165                1170

Leu Arg Pro Lys Thr Ser Gly Val Gly Leu Gly Gly Ser Tyr Ser
    1175                1180                1185

Ser Arg Asn Ala Ser Ala Glu Thr Lys Glu Ala Ser Thr Leu Ala
    1190                1195                1200

Thr Val Pro Met Thr Pro Lys Pro Thr Ser Arg Ser Ala Lys Arg
    1205                1210                1215

Asp Val Ser Gln Val Gln Phe Ile Gly Pro Asn Ala Ser Tyr Met
    1220                1225                1230

Gly Ser Leu Ala Arg Leu Phe Asp Ala Ala Gln Ala Val Asp Gln
    1235                1240                1245

Ile Ala Arg Gln Val Asp Asp Pro Gly Leu Arg Leu Ala Asp Lys
    1250                1255                1260

Thr Gln Val Gly Leu Glu Leu Cys Thr Arg His Ala Ala Glu Phe
    1265                1270                1275

Phe Gly Phe Tyr Ile Cys Arg Phe Val Leu Ala Asp Leu Gly Leu
    1280                1285                1290
```

Leu Leu Asp Lys Phe Leu Lys Arg Gly Ser Glu Trp Val Met Thr
1295            1300            1305

<210> SEQ ID NO 22
<211> LENGTH: 2731
<212> TYPE: DNA
<213> ORGANISM: Hypocrea jecorina

<400> SEQUENCE: 22

| | | | | | |
|---|---|---|---|---|---|
| atgcagcaac | cgccctcctt | agttggcgac | cgcagcatca | ccggcctggg | agacgcagcc | 60 |
| agccgaccaa | atctctcttc | atcctcgcct | accgtcacca | gcgcgccctc | ggcaccgaca | 120 |
| tcgccaccgc | cgcggccgcc | aatatcgctg | aatccccgt | cgcgagagcc | tcctggcgtc | 180 |
| gagcccgtgc | tccgcatcac | gccagtcccg | cgctccgtct | ttgcctctgt | ccaccagccg | 240 |
| cgcaagtcgt | cgctggtcca | gacgtcgcac | gtcctgccct | cgcccaggac | cgccgccgca | 300 |
| gctcaccatc | accatcccgt | ctcgcattcc | gcctctggca | gcagcggcag | caacggcagt | 360 |
| ggaagcggca | gtggcagcgg | cagcggcaat | ctgctgcgtc | aaacgcatcg | cgacaccgtg | 420 |
| caccccccg | tcaagcggcc | atccacccg | tcgtcgcatc | ccaccagggg | cgccagcacc | 480 |
| ggagcatcgc | cgcagcaggg | cgccagctcc | cgaaaccgct | cgtcgacgtc | gcccgtttcg | 540 |
| tccccggcga | gtcgcacgcc | tccttatgca | tctcgtcagg | cctcagtttc | ccattcccgc | 600 |
| cagcagcaca | ccaccatca | tcagcaccaa | caccagcatt | accactccca | caccagctcg | 660 |
| actaccagtc | gcgccagcat | cgaggccgta | gtcggtgccg | tccccgatcc | ctcaggtcac | 720 |
| cgagcgccgc | cgaaaccccg | tcgaccggat | cgcaaccact | ttggcgcgtc | agatcgcagc | 780 |
| gcaactccca | ccctgtcgca | cttcatgagg | gcagagtcga | gcatgtccat | gagacattac | 840 |
| gagagcggcc | ccttacgctc | catgtcgccg | aaccctacg | gaaccctgc | cgccaccacg | 900 |
| acgtcgtcca | ctgccagaat | gccgcacgag | cagagccacg | atccctacgc | ccctcgcggc | 960 |
| cactctcgcg | atcactcggg | gaagagcagc | agagacatgg | gcaagcccg | agctcagaag | 1020 |
| aatccctcac | agaaggcgat | gctctcccgt | gccctgcaaa | aggccaacac | cgcagttcag | 1080 |
| ctcgacaatg | ctcagaactt | cgaaggcgct | cgagaagcgt | acgccgaggc | ttgcgacttg | 1140 |
| ttgcagcagg | tgcttgaccg | aacaccggga | gatgaggaca | gcggaagct | cgaagccatt | 1200 |
| gtaagtcacg | gcggcaaccg | gaatgtcgag | cccgttgtct | gtcattagta | gatcacttgg | 1260 |
| aactgacaat | ttcaatctgt | agcaccaaac | ttacaccagc | cgcatcgatg | agctggatca | 1320 |
| gttgggccct | tggcaggttg | agaccgtcaa | ggctctgccg | cgcgcggcag | agagcgagga | 1380 |
| gtacagcgcg | tccatattca | taccccagga | ttacgacatg | ggcgatgaag | ctcccaggat | 1440 |
| tgagacggca | cgggtggtga | gctacatcgc | tggagacaac | gcgtctccct | ttgcagcagc | 1500 |
| gcccaaccag | tggcagcagt | cgggaggtca | cacggcatct | gaacggctgc | agcccaaccg | 1560 |
| cggtctggaa | ccgggtctgc | tacagtcgtc | cttctctcgg | gccccgaggt | cgcccaggcg | 1620 |
| gctgcagtcc | accgatgatc | ttcgcgcaca | gcatcaggag | ggccagtatg | cgcctccccc | 1680 |
| actctcgcct | cgctcgcagt | cgccggtaaa | gacgcatgac | catgacgacg | acatgtttgc | 1740 |
| cgaactgcca | ccacacgagc | cctatcagta | ccagcaagag | cacgaccatc | aagaccacca | 1800 |
| tcaagactac | catcaacatc | accgccatca | caaccaccac | catcacgaac | gacagcccag | 1860 |
| cgagactgtc | ctatcctcat | acgagctcca | gggtcatgtg | gatggaggaa | tccaaaactc | 1920 |
| atggctagat | ccaattgacg | agtcgggagg | ctcaacagcg | tcgtctgtac | actcacgcac | 1980 |
| ctcttcgctt | ggctaccgtc | gacgccatat | ccgggccgtg | agcgggaaca | ccgaggccga | 2040 |

```
gtttgacacg gcgctggacg ctgctatcga ggctgcctac gacgacggct acgagcccat    2100
ggactctgta gactatggga ccattgatgc tgggggggaca atagcatggc aggcgtattg    2160
cacaaggtgg agatggcgcg cgaacgagcg agacagacgg agcaggaagc ctatgacgag    2220
ctggccaacc tccgacaggc gcactcacag aatccgcagc accagcagga ggaggacagg    2280
tatactgccg agggattcta cgaggacgac tcgtctgaag aggaggagag actattggac    2340
gagattacac gcgactttgc cattgaggac tttaccatgg aaaacccgaa tggcacacag    2400
gtgtcagcta ggcagcagga tgcatggaac gaggacgaga cgaggccgga tttcatctcg    2460
ggcgtccgat cctttctgc cctgtcgcag aggccaccca ttcctcaggc ctacgccgcc    2520
aacgcctcgc agccagcagc ccccctccg acatccgcat tgccagacct gccaccagga    2580
cgccctggtc aaaatccaaa gcaactcaag atcgagacgg caaacattgt acaaacccag    2640
aagtcggtct atgacgacga cgaaatctcc ccaagcacgc aagagccgcc gcccgagacg    2700
ctcgtccgga cggcgagcgc gcagcctgta a                                  2731
```

<210> SEQ ID NO 23
<211> LENGTH: 882
<212> TYPE: PRT
<213> ORGANISM: Hypocrea jecorina

<400> SEQUENCE: 23

```
Met Gln Gln Pro Pro Ser Leu Val Gly Asp Arg Ser Ile Thr Gly Leu
 1               5                  10                  15

Gly Asp Ala Ala Ser Arg Pro Asn Leu Ser Ser Ser Pro Thr Val
            20                  25                  30

Thr Ser Ala Pro Ser Ala Pro Thr Ser Pro Pro Arg Pro Pro Ile
        35                  40                  45

Ser Leu Asn Pro Pro Ser Arg Glu Pro Pro Gly Val Glu Pro Val Leu
 50                  55                  60

Arg Ile Thr Pro Val Pro Arg Ser Val Phe Ala Ser Val His Gln Pro
 65                  70                  75                  80

Arg Lys Ser Ser Leu Val Gln Thr Ser His Val Leu Pro Ser Pro Arg
                85                  90                  95

Thr Ala Ala Ala His His His His Pro Val Ser His Ser Ala Ser
            100                 105                 110

Gly Ser Ser Gly Ser Asn Gly Ser Gly Ser Gly Ser Gly Ser
        115                 120                 125

Gly Asn Leu Leu Arg Gln Thr His Arg Asp Thr Val His Pro Pro Val
130                 135                 140

Lys Arg Pro Ser Thr Pro Ser Ser His Pro Thr Arg Gly Ala Ser Thr
145                 150                 155                 160

Gly Ala Ser Pro Gln Gln Gly Ala Ser Arg Asn Arg Ser Ser Thr
                165                 170                 175

Ser Pro Val Ser Ser Pro Ala Ser Arg Thr Pro Pro Tyr Ala Ser Arg
            180                 185                 190

Gln Ala Ser Val Ser His Ser Arg Gln Gln His Asn His His Gln
        195                 200                 205

His Gln His Gln His Tyr His Ser His Thr Ser Ser Thr Thr Ser Arg
    210                 215                 220

Ala Ser Ile Glu Ala Val Val Gly Ala Val Pro Asp Pro Ser Gly His
225                 230                 235                 240
```

```
Arg Ala Pro Pro Lys Pro Arg Pro Asp Arg Asn His Phe Gly Ala
                245                 250                 255

Ser Asp Arg Ser Ala Thr Pro Thr Leu Ser His Phe Met Arg Ala Glu
            260                 265                 270

Ser Ser Met Ser Met Arg His Tyr Glu Ser Gly Pro Leu Arg Ser Met
        275                 280                 285

Ser Pro Asn Pro Tyr Gly Thr Pro Ala Ala Thr Thr Thr Ser Ser Thr
    290                 295                 300

Ala Arg Met Pro His Glu Gln Ser His Asp Pro Tyr Ala Pro Arg Gly
305                 310                 315                 320

His Ser Arg Asp His Ser Gly Lys Ser Arg Asp Met Gly Lys Pro
                325                 330                 335

Arg Ala Gln Lys Asn Pro Ser Gln Lys Ala Met Leu Ser Arg Ala Leu
                340                 345                 350

Gln Lys Ala Asn Thr Ala Val Gln Leu Asp Asn Ala Gln Asn Phe Glu
            355                 360                 365

Gly Ala Arg Glu Ala Tyr Ala Glu Ala Cys Asp Leu Leu Gln Gln Val
        370                 375                 380

Leu Asp Arg Thr Pro Gly Asp Glu Asp Lys Arg Lys Leu Glu Ala Ile
385                 390                 395                 400

His Gln Thr Tyr Thr Ser Arg Ile Asp Glu Leu Asp Gln Leu Gly Pro
                405                 410                 415

Trp Gln Val Glu Thr Val Lys Ala Leu Pro Ala Arg Pro Glu Ser Glu
                420                 425                 430

Glu Tyr Ser Ala Ser Ile Phe Ile Pro Gln Asp Tyr Asp Met Gly Asp
            435                 440                 445

Glu Ala Pro Arg Ile Glu Thr Ala Arg Val Val Ser Tyr Ile Ala Gly
        450                 455                 460

Asp Asn Ala Ser Pro Phe Ala Ala Pro Asn Gln Trp Gln Ser
465                 470                 475                 480

Gly Gly His Thr Ala Ser Glu Arg Leu Gln Pro Asn Arg Gly Leu Glu
                485                 490                 495

Pro Gly Leu Leu Gln Ser Ser Phe Ser Arg Ala Pro Arg Ser Pro Arg
            500                 505                 510

Arg Leu Gln Ser Thr Asp Asp Leu Arg Ala Gln His Gln Glu Gly Gln
        515                 520                 525

Tyr Ala Pro Pro Pro Leu Ser Pro Arg Ser Gln Ser Pro Val Lys Thr
    530                 535                 540

His Asp His Asp Asp Asp Met Phe Ala Glu Leu Pro Pro His Glu Pro
545                 550                 555                 560

Tyr Gln Tyr Gln Gln Glu His Asp His Gln Asp His Gln Asp Tyr
                565                 570                 575

His Gln His His Arg His His Asn His His His Glu Arg Gln Pro
            580                 585                 590

Ser Glu Thr Val Leu Ser Ser Tyr Glu Leu Gln Gly His Val Asp Gly
        595                 600                 605

Gly Ile Gln Asn Ser Trp Leu Asp Pro Ile Asp Glu Ser Gly Gly Ser
    610                 615                 620

Thr Ala Ser Ser Val His Ser Arg Thr Ser Ser Leu Gly Tyr Arg Arg
625                 630                 635                 640

Arg His Ile Arg Ala Val Ser Gly Asn Thr Glu Ala Glu Phe Asp Thr
                645                 650                 655
```

```
Ala Leu Asp Ala Ala Ile Glu Ala Ala Tyr Asp Asp Gly Tyr Glu Pro
            660                 665                 670

Met Asp Ser Val Asp Tyr Gly Thr Ile Asp Ala Gly Gly Thr Ile Ala
        675                 680                 685

Trp Gln Ala Tyr Cys Thr Arg Trp Arg Trp Arg Ala Asn Glu Arg Asp
690                 695                 700

Arg Arg Ser Arg Lys Pro Met Thr Ser Trp Pro Thr Ser Asp Arg Arg
705                 710                 715                 720

Thr His Arg Ile Arg Ser Thr Ser Arg Arg Thr Gly Ile Leu Pro
            725                 730                 735

Arg Asp Ser Thr Arg Thr Thr Arg Leu Lys Arg Arg Asp Tyr Trp
        740                 745                 750

Thr Arg Leu His Ala Thr Leu Pro Leu Arg Thr Leu Pro Trp Lys Thr
            755                 760                 765

Arg Met Ala His Arg Cys Gln Leu Gly Ser Arg Met His Gly Thr Arg
        770                 775                 780

Thr Arg Arg Gly Arg Ile Ser Ser Arg Ala Ser Asp Pro Phe Leu Pro
785                 790                 795                 800

Cys Arg Arg Gly His Pro Phe Leu Arg Pro Thr Pro Thr Pro Arg
            805                 810                 815

Ser Gln Gln Pro Pro Leu Arg His Pro His Cys Gln Thr Cys His Gln
        820                 825                 830

Asp Ala Leu Val Lys Ile Gln Ser Asn Ser Arg Ser Arg Gln Thr
            835                 840                 845

Leu Tyr Lys Pro Arg Ser Arg Ser Met Thr Thr Lys Ser Pro Gln
        850                 855                 860

Ala Arg Lys Ser Arg Arg Pro Arg Arg Ser Ser Gly Arg Arg Ala Arg
865                 870                 875                 880

Ser Leu

<210> SEQ ID NO 24
<211> LENGTH: 896
<212> TYPE: PRT
<213> ORGANISM: Trichoderma harzianum

<400> SEQUENCE: 24

Met Gly Ile Thr Ser Tyr Phe Lys Ala Ser Thr Lys Lys Ala Glu Gln
1               5                   10                  15

Glu Thr Ala Ala Pro Pro Ala Pro Pro Ala Lys Pro Val Ala Pro Pro
            20                  25                  30

Arg Leu Gln Gln Glu Thr Arg Gln Ser Ile Met Ser Glu Lys Pro Pro
        35                  40                  45

Ser Ser Val Ser Gly Asn Asp Met Asp Leu Gln Pro Pro Thr Pro Arg
    50                  55                  60

Phe His Ser Arg Pro Gln Ser Ser Ser Gly Arg Ser Thr Pro Ser Met
65                  70                  75                  80

Gln Ser Ser Met Phe Leu Asp Asp Ile Lys His Glu Val Met Val Asn
                85                  90                  95

Tyr Leu Tyr Gln Gln Gln Cys Ser Gln Leu Trp Val Ser Asp Gly Ser
            100                 105                 110

Gly Glu Ile Glu Gly Val Leu Leu Arg Lys Ala Arg Gly His Tyr Met
        115                 120                 125

Ala Cys Pro Pro Gln Leu Ala Ser Ser Pro Phe Ala Leu Ala Cys Ala
    130                 135                 140
```

```
Ala Leu Asn Val Gln Cys Ala Met Thr Val Asn Ser Arg Val Ile Lys
145                 150                 155                 160

Thr Phe Leu Gln Trp Ser Pro Asp Ala Val Asp Val Pro Leu Met Asn
            165                 170                 175

Gly Leu Arg Val Gln Ile Leu Pro Thr Ile Asp Asp Leu Pro Arg Ala
            180                 185                 190

Arg Lys Tyr Gln Phe Ala Ala Phe Val Ala Ser Glu Gly Leu Leu Ile
            195                 200                 205

Val Trp Asp Asp Ala Leu His Leu Val Ala Arg Ala Lys Ala Ile
210                 215                 220

Glu Ser Glu Leu Met Glu Leu Val Trp Lys Ala Gly Asn Pro Asp Glu
225                 230                 235                 240

Glu Gly Glu Asp Glu Lys Arg Ala Gln Pro Val Ala Glu Val Glu Ile
            245                 250                 255

Asp Glu Glu Ser Gly Glu Ile Lys Pro Glu Lys Arg Pro Ile His Leu
            260                 265                 270

Gln Asn Thr Val Leu Val Ser Leu Thr Leu Val Leu Val Thr Val Ser
            275                 280                 285

Leu Gly Ala Ala Trp Arg Gln Leu Ala Ile Glu Val Ser Val Asp Asn
290                 295                 300

Thr Tyr Ile Arg Leu Ala Leu Val Ala Leu Ala Pro Val Gln Ile Phe
305                 310                 315                 320

Phe Thr Leu Phe Phe Ala Gln Val Ile Val Gly Cys Leu Ala Gln Ile
            325                 330                 335

Phe Gly Pro Ile Arg Gln Leu Thr Ile Asn Ser Lys Phe Tyr Ser Ala
            340                 345                 350

Arg Pro Pro Pro Arg Leu Gln Ser Ala Ile Leu Pro His Val Thr Ile
            355                 360                 365

Gln Cys Pro Val Tyr Lys Glu Gly Leu Gln Gly Val Ile Met Pro Thr
            370                 375                 380

Val Lys Ser Ile Lys Gln Ala Met Ser Thr Tyr Glu Leu Gln Gly Gly
385                 390                 395                 400

Ser Ala Asn Met Phe Ile Asn Asp Asp Gly Leu Gln Leu Ile Ser Glu
            405                 410                 415

Glu Asp Arg Leu Ala Arg Ile Glu Phe Tyr Ala Asp Asn Ser Ile Gly
            420                 425                 430

Trp Val Ala Arg Pro Lys His Gly Glu Asn Gly Phe Thr Arg Lys Gly
            435                 440                 445

Lys Phe Lys Lys Ala Ser Asn Met Asn Phe Ala Leu Met Ile Ser Cys
450                 455                 460

Lys Val Glu Glu Lys Leu Gln Ala Ile Glu Arg Pro Pro Glu Trp Ser
465                 470                 475                 480

Gln Asn Asp Glu Ala Leu Ala Tyr Glu Ala Leu Lys Glu Val Leu
            485                 490                 495

Glu Ala Asp Gly Arg Ala Trp Ala Asp Gly Asn Ile Arg Met Gly Asp
            500                 505                 510

Tyr Ile Leu Leu Ile Asp Ser Asp Thr Arg Val Pro Ala Asp Cys Leu
            515                 520                 525

Leu Asp Ala Val Ser Glu Met Glu Gln Ser Pro Asp Val Gly Ile Met
530                 535                 540

Gln Phe Ser Ser Gly Val Met Gln Val Val His Thr Tyr Phe Glu Asn
545                 550                 555                 560
```

```
Gly Ile Thr Phe Phe Thr Asn Leu Ile Tyr Ser Ala Ile Arg Tyr Thr
                565                 570                 575

Val Ser Asn Gly Asp Val Ala Pro Phe Val Gly His Asn Ala Ile Leu
            580                 585                 590

Arg Trp Ser Ala Ile Gln Gln Val Ala Tyr Gln Asp Glu Asp Gly Tyr
        595                 600                 605

Asp Lys Phe Trp Ser Glu Ser His Val Ser Glu Asp Phe Asp Met Ser
    610                 615                 620

Leu Arg Leu Gln Val Asn Gly Tyr Ile Ile Arg Leu Ala Ala Trp Ala
625                 630                 635                 640

Gly Glu Gly Phe Lys Glu Gly Val Ser Leu Thr Val Tyr Asp Glu Leu
                645                 650                 655

Ala Arg Trp Glu Lys Tyr Ala Tyr Gly Cys Asn Glu Leu Leu Phe His
                660                 665                 670

Pro Ile Arg Thr Trp Leu Trp Arg Gly Pro Phe Thr Pro Leu Phe Arg
            675                 680                 685

Arg Phe Leu Phe Ser Asn Ile Arg Phe Thr Ser Lys Ile Thr Val Ile
        690                 695                 700

Ser Tyr Ile Gly Thr Tyr Tyr Ala Ile Gly Ala Ala Trp Ile Leu Thr
705                 710                 715                 720

Val Val Asn Tyr Phe Val Met Gly Trp Tyr Asn Gly Tyr Leu Asp Lys
                725                 730                 735

Tyr Tyr Ile Asp Ser Trp Gln Val Trp Phe Ser Ile Ile Ile Val Phe
            740                 745                 750

Asn Gly Leu Gly Asn Ile Ala Leu Ala Val Met Arg Tyr Arg Val Gly
        755                 760                 765

Glu Arg Gly Leu Leu Tyr Ala Leu Phe Glu Asn Phe Met Trp Thr Leu
    770                 775                 780

Met Leu Ala Ile Phe Leu Gly Gly Leu Ser Leu His Val Ser Gln Ala
785                 790                 795                 800

Leu Leu Ala His Met Phe Glu Ile Asn Met Thr Trp Gly Ala Thr Ala
                805                 810                 815

Lys Glu Ala Glu Phe Ser Asn Phe Phe Ile Glu Val Pro Lys Val Leu
                820                 825                 830

Lys Lys Phe Lys Phe Ser Met Ile Phe Ser Leu Ile Phe Ile Ile Gly
            835                 840                 845

Met Ile Leu Leu Ala Gln Ala Pro Phe Val Pro Tyr Asp Trp Gln Ile
    850                 855                 860

Lys Asp Phe Val Ala Ile Leu Pro Met Ala Thr Val Ala Ala Ser His
865                 870                 875                 880

Phe Leu Leu Pro Leu Ala Leu Asn Pro Ala Leu Met Thr Phe Ser Trp
                885                 890                 895
```